United States Patent
Nagamine et al.

(10) Patent No.: US 11,036,131 B2
(45) Date of Patent: Jun. 15, 2021

(54) RESIST COMPOSITION, METHOD OF FORMING RESIST PATTERN, AND COMPOUND

(71) Applicant: TOKYO OHKA KOGYO CO., LTD., Kawasaki (JP)

(72) Inventors: Takashi Nagamine, Kawasaki (JP); Tsuyoshi Nakamura, Incheon (KR); Kazuishi Tanno, Incheon (KR)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 90 days.

(21) Appl. No.: 16/225,290

(22) Filed: Dec. 19, 2018

(65) Prior Publication Data

US 2019/0204739 A1  Jul. 4, 2019

(30) Foreign Application Priority Data

Dec. 28, 2017  (JP) .............................. JP2017-253724

(51) Int. Cl.

| | |
|---|---|
| *G03F 7/004* | (2006.01) |
| *G03F 7/039* | (2006.01) |
| *C07C 309/06* | (2006.01) |
| *C07C 309/12* | (2006.01) |
| *C07C 309/19* | (2006.01) |
| *C07J 9/00* | (2006.01) |
| *G03F 7/20* | (2006.01) |
| *C07J 31/00* | (2006.01) |
| *C07J 19/00* | (2006.01) |
| *C07J 43/00* | (2006.01) |
| *G03F 7/038* | (2006.01) |
| *C08L 33/14* | (2006.01) |
| *C07C 309/04* | (2006.01) |
| *C07C 303/32* | (2006.01) |
| *G03F 7/30* | (2006.01) |
| *C08G 61/04* | (2006.01) |
| *G03F 7/38* | (2006.01) |

(52) U.S. Cl.
CPC .......... *G03F 7/0045* (2013.01); *C07C 303/32* (2013.01); *C07C 309/04* (2013.01); *C07C 309/06* (2013.01); *C07C 309/12* (2013.01); *C07C 309/19* (2013.01); *C07J 19/00* (2013.01); *C07J 31/006* (2013.01); *C07J 43/003* (2013.01); *C08L 33/14* (2013.01); *G03F 7/0046* (2013.01); *G03F 7/0382* (2013.01); *G03F 7/0397* (2013.01); *G03F 7/2041* (2013.01); *G03F 7/30* (2013.01); *C07J 9/005* (2013.01); *C08G 61/04* (2013.01); *G03F 7/38* (2013.01)

(58) Field of Classification Search
CPC .... G03F 7/0045; G03F 7/0397; G03F 7/2041; G03F 7/30; G03F 7/38; C07J 31/006; C07J 19/00; C07J 9/005; C07C 309/04; C07C 309/06; C07C 309/12; C07C 309/19
See application file for complete search history.

(56) References Cited

U.S. PATENT DOCUMENTS

| | | | | |
|---|---|---|---|---|
| 6,180,316 B1 * | 1/2001 | Kajita | ................... | G03F 7/0045 430/270.1 |
| 2009/0061358 A1 | 3/2009 | Ohashi et al. | | |
| 2009/0274978 A1 | 11/2009 | Ohashi et al. | | |
| 2011/0250538 A1 * | 10/2011 | Li | ......................... | G03F 7/0045 430/270.1 |
| 2012/0077121 A1 * | 3/2012 | Hasegawa | ............... | C07C 69/67 430/270.1 |
| 2012/0135350 A1 * | 5/2012 | Kobayashi | ............ | G03F 7/0397 430/285.1 |

FOREIGN PATENT DOCUMENTS

| | | |
|---|---|---|
| JP | 4569786 B | 10/2010 |
| JP | 5019071 B | 9/2012 |

* cited by examiner

*Primary Examiner* — John S Chu

(74) *Attorney, Agent, or Firm* — Knobbe Martens Olson & Bear LLP

(57) ABSTRACT

A resist composition containing a compound (B1) represented by Formula (b1) in which $R^{b1}$ represents a monovalent hydrocarbon group which has a steroid skeleton and 17 to 50 carbon atoms, $Y^{b1}$ and $Y^{b2}$ each independently represent a divalent linking group having a hetero atom, $V^{b1}$ represents a divalent linking group containing a cyclic aliphatic hydrocarbon group, $V^{b2}$ represents an alkylene group, a fluorinated alkylene group, or a single bond, $R^{f1}$ represents a hydrogen atom, a fluorine atom, or a fluorinated alkyl group having 1 to 5 carbon atoms, m represents an integer of 1 or greater, and $M^{m+}$ represents an m-valent organic cation

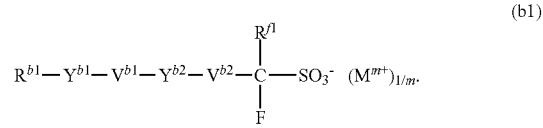

(b1)

10 Claims, No Drawings

RESIST COMPOSITION, METHOD OF FORMING RESIST PATTERN, AND COMPOUND

BACKGROUND OF THE INVENTION

Field of the Invention

The present invention relates to a resist composition, a method of forming a resist pattern, and a compound.

Priority is claimed on Japanese Patent Application No. 2017-253724, filed on Dec. 28, 2017, the content of which is incorporated herein by reference.

Description of Related Art

In lithography techniques, for example, a resist film formed of a resist material is formed on a substrate, and the resist film is subjected to selective exposure, followed by a development treatment, thereby forming a resist pattern having a predetermined shape on the resist film. A resist material in which the exposed portions of the resist film become soluble in a developing solution is called a positive type, and a resist material in which the exposed portions of the resist film become insoluble in a developing solution is called a negative type.

In recent years, in the production of semiconductor elements and liquid crystal display elements, advances in lithography techniques have led to rapid progress in the field of pattern miniaturization. Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are used in mass production. Furthermore, research is also being conducted into lithography techniques that use an exposure light source having a shorter wavelength (higher energy) than these excimer lasers, such as electron beams (EB), extreme ultraviolet radiation (EUV), and X rays.

Resist materials for use with these types of exposure light sources require lithography characteristics such as a high resolution capable of reproducing patterns of minute dimensions, and a high level of sensitivity to these types of exposure light sources.

As a resist material that satisfies these requirements, in the related art, a chemically amplified resist composition which includes a base material component whose solubility in a developing solution is changed due to an action of an acid and an acid-generator component that generates an acid upon exposure has been used.

For example, in a case where the developing solution is an alkali developing solution (alkali developing process), as a positive type chemically amplified resist composition, a composition which contains a resin component (base resin) whose solubility in an alkali developing solution is increased due to an action of an acid and an acid generator component has been typically used. In a case where a resist film formed using such a resist composition is selectively exposed at the time of forming a resist pattern, in exposed portions, an acid is generated from the acid generator component, and the polarity of the base resin increases by the action of the generated acid, thereby making the exposed portions of the resist film soluble in the alkali developing solution. Thus, by conducting alkali development, the unexposed portions of the resist film remain to form a positive type resist pattern.

On the other hand, in a case where such a chemically amplified resist composition is applied to a solvent developing process using a developing solution containing an organic solvent (organic developing solution), since the solubility in an organic developing solution is relatively decreased at the time of an increase in polarity of the base resin, the unexposed portions of the resist film are dissolved and removed by the organic developing solution so that a negative type resist pattern in which the exposed portions of the resist film remain is formed. Such a solvent developing process for forming a negative type resist pattern is also referred to as a "negative type developing process".

A base resin to be used in a chemically amplified resist composition typically has a plurality of constitutional units for improving lithography characteristics.

For example, in a case of a resin component whose solubility in an alkali developing solution is increased due to an action of an acid, a constitutional unit containing an acid decomposable group which is decomposed due to the action of an acid generated from an acid generator or the like so that the polarity is increased is used. In addition, a constitutional unit containing a lactone-containing cyclic group, a constitutional unit containing a polar group such as a hydroxyl group, and the like are used in combination.

Further, in formation of a resist pattern, the behavior of an acid generated from an acid generator component upon exposure is regarded as a factor that greatly affects the lithography characteristics.

As the acid generator to be used in the chemically amplified resist composition, various acid generators have been suggested so far. For example, an onium salt-based acid generator such as an iodonium salt or a sulfonium salt, an oxime sulfonate-based acid generator, a diazomethane-based acid generator, a nitrobenzyl sulfonate-based acid generator, an iminosulfonate-based acid generator, and a disulfone-based acid generator have been known.

As the onium salt-based acid generator, an agent in which a cation moiety has an onium ion such as triphenyl sulfonium has been mainly used. As the anion moiety of the onium salt-based acid generator, an alkyl sulfonic acid ion or a fluorinated alkyl sulfonic acid ion in which some or all hydrogen atoms in the alkyl group have been substituted with fluorine atoms has been typically used.

Further, for the purpose of improving various lithography characteristics in the formation of a resist pattern, as an anion moiety, an onium salt-based acid generator that has an anion having a specific structure with a steroid skeleton has been suggested (for example, see Japanese Patent Nos. 4569786 and 5019071).

SUMMARY OF THE INVENTION

However, in the inventions described in Japanese Patent No. 4569786, there is room for improvement for the purpose of making the lithography characteristics excellent.

The present invention has been made in consideration of the above-described circumstances, and an object thereof is to provide a resist composition with excellent lithography characteristics; a compound useful for the resist composition; and a method of forming a resist pattern obtained by using the resist composition.

According to a first aspect of the present invention, there is provided a resist composition which generates an acid upon exposure and whose solubility in a developing solution is changed due to an action of the acid, the resist composition including: a base material component (A) whose solubility in a developing solution is changed due to the action of an acid; and an acid generator component (B) which generates an acid upon exposure, in which the acid generator component (B) contains a compound (B1) represented by Formula (b1).

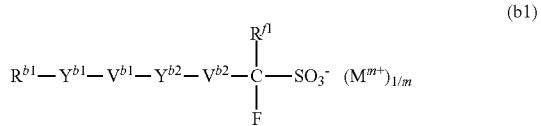

[In the formula, $R^{b1}$ represents a monovalent hydrocarbon group which has a steroid skeleton and 17 to 50 carbon atoms, where the hydrocarbon group may have a hetero atom, $Y^{b1}$ and $Y^{b2}$ each independently represent a divalent linking group having a hetero atom, $V^{b1}$ represents a divalent linking group containing a cyclic aliphatic hydrocarbon group, $V^{b2}$ represents an alkylene group, a fluorinated alkylene group, or a single bond, $R^{f1}$ represents a hydrogen atom, a fluorine atom, or a fluorinated alkyl group having 1 to 5 carbon atoms, m represents an integer of 1 or greater, and $M^{m+}$ represents an m-valent organic cation.]

According to a second aspect of the present invention, there is provided a method of forming a resist pattern, including: a step of forming a resist film on a support using the resist composition according to the first aspect; a step of exposing the resist film; and a step of developing the exposed resist film to form a resist pattern.

According to a third aspect of the present invention, there is provided a compound which is represented by Formula (b1).

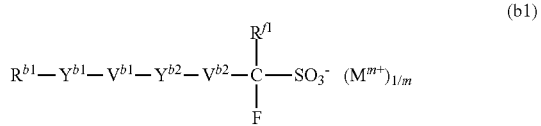

[In the formula, $R^{b1}$ represents a monovalent hydrocarbon group which has a steroid skeleton and 17 to 50 carbon atoms, where the hydrocarbon group may have a hetero atom, $Y^{b1}$ and $Y^{b2}$ each independently represent a divalent linking group having a hetero atom, $V^{b1}$ represents a divalent linking group containing a cyclic aliphatic hydrocarbon group, $V^{b2}$ represents an alkylene group, a fluorinated alkylene group, or a single bond, $R^{f1}$ represents a hydrogen atom, a fluorine atom, or a fluorinated alkyl group having 1 to 5 carbon atoms, m represents an integer of 1 or greater, and $M^{m+}$ represents an m-valent organic cation.]

According to the present invention, it is possible to provide a resist composition with excellent lithography characteristics; a compound useful for the resist composition; and a method of forming a resist pattern obtained by using the resist composition.

DETAILED DESCRIPTION OF THE INVENTION

In the present description and claims, the term "aliphatic" is a relative concept used in relation to the term "aromatic", and defines a group or compound that has no aromaticity.

The term "alkyl group" includes a linear, branched or cyclic, monovalent saturated hydrocarbon, unless otherwise specified. The same applies for the alkyl group in an alkoxy group.

The term "alkylene group" includes a linear, branched or cyclic, divalent saturated hydrocarbon, unless otherwise specified.

A "halogenated alkyl group" is a group in which some or all hydrogen atoms of an alkyl group are substituted with halogen atoms. Examples of the halogen atom include a fluorine atom, a chlorine atom, a bromine atom and an iodine atom.

A "fluorinated alkyl group" or a "fluorinated alkylene group" is a group in which some or all hydrogen atoms of an alkyl group or an alkylene group have been substituted with fluorine atoms.

The term "constitutional unit" indicates a monomer unit that contributes to the formation of a polymeric compound (a resin, a polymer, or a copolymer).

The expression "may have a substituent" refers to a case where a hydrogen atom (—H) is substituted with a monovalent group, or a case where a methylene (—CH$_2$—) group is substituted with a divalent group.

The term "exposure" is used as a general concept that includes irradiation with any form of radiation.

"Constitutional unit derived from an acrylic acid ester" indicates a constitutional unit that is formed by the cleavage of the ethylenic double bond of an acrylic acid ester.

"Acrylic acid ester" indicates a compound in which the terminal hydrogen atom of the carboxy group of acrylic acid (CH$_2$=CH—COOH) has been substituted with an organic group.

The acrylic acid ester may have the hydrogen atom bonded to the carbon atom at the α-position substituted with a substituent. The substituent ($R^{\alpha 0}$) that substitutes the hydrogen atom bonded to the carbon atom at the α-position is an atom other than hydrogen or a group, and examples thereof include an alkyl group having 1 to 5 carbon atoms and a halogenated alkyl group having 1 to 5 carbon atoms. Further, the acrylic acid ester having the hydrogen atom bonded to the carbon atom at the α-position substituted with a substituent ($R^{\alpha 0}$) in which the substituent has been substituted with a substituent containing an ester bond (itaconic acid diester), or acrylic acid having the hydrogen atom bonded to the carbon atom at the α-position substituted with a substituent ($R^{\alpha 0}$) in which the substituent has been substituted with a hydroxyalkyl group or a group in which the hydroxyl group in a hydroxyalkyl group has been modified (α-hydroxyalkyl acrylic acid ester) can be exemplified as the acrylic acid ester having the hydrogen atom bonded to the carbon atom at the α-position substituted with a substituent. A carbon atom at the α-position of the acrylic acid ester indicates the carbon atom bonded to the carbonyl group, unless specified otherwise.

Hereinafter, an acrylic acid ester in which the hydrogen atom bonded to the carbon atom at the α-position is substituted with a substituent is also referred to as an α-substituted acrylic acid ester". Further, an acrylic acid ester and an α-substituted acrylic acid ester are also collectively referred to as an "(α-substituted) acrylic acid ester".

"Constitutional unit derived from acrylamide" indicates a constitutional unit that is formed by the cleavage of the ethylenic double bond of acrylamide.

The acrylamide may have the hydrogen atom bonded to the carbon atom at the α-position substituted with a substituent, and may have either or both terminal hydrogen atoms on the amino group of acrylamide substituted with a substituent. A carbon atom at the α-position of an acrylamide indicates the carbon atom bonded to the carbonyl group, unless specified otherwise.

As the substituent which substitutes the hydrogen atom bonded to the carbon atom at the α-position of acrylamide, the same substituents as those described above for the substituent ($R^{\alpha 0}$) at the α-position of the above-described α-position of the above-described α-substituted acrylic acid ester can be exemplified.

"Constitutional unit derived from hydroxystyrene or a hydroxystyrene derivative" indicates a constitutional unit that is formed by the cleavage of an ethylenic double bond of hydroxystyrene or a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof.

Examples of the derivatives thereof include hydroxystyrene in which the hydrogen atom of the hydroxyl group has been substituted with an organic group and may have the hydrogen atom at the α-position substituted with a substituent; and hydroxystyrene which has a substituent other than a hydroxyl group bonded to the benzene ring and may have the hydrogen atom at the α-position substituted with a substituent. Here, the α-position (carbon atom at the α-position) indicates the carbon atom having the benzene ring bonded thereto, unless specified otherwise.

As the substituent which substitutes the hydrogen atom at the α-position of hydroxystyrene, the same substituents as those described above for the substituent at the α-position of the above-described α-substituted acrylic acid ester can be exemplified.

"Constitutional unit derived from vinylbenzoic acid or a vinylbenzoic acid derivative" indicates a constitutional unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include vinylbenzoic acid in which the hydrogen atom of the carboxy group has been substituted with an organic group and may have the hydrogen atom at the α-position substituted with a substituent; and vinylbenzoic acid which has a substituent other than a hydroxyl group and a carboxy group bonded to the benzene ring and may have the hydrogen atom at the α-position substituted with a substituent. Here, the α-position (carbon atom at the α-position) indicates the carbon atom having the benzene ring bonded thereto, unless specified otherwise.

The term "styrene" is a concept including those obtained by substitution of styrene and a hydrogen atom at the α-position of styrene with other substituents such as an alkyl group and a halogenated alkyl group.

The term "styrene derivative" is a concept including those obtained by substitution of a hydrogen atom at the α-position of styrene with other substituents such as an alkyl group and a halogenated alkyl group; and derivatives thereof. Examples of derivatives thereof include those obtained by bonding a substituent to a benzene ring of styrene in which a hydrogen atom at the α-position may be substituted with a substituent. In addition, the α-position (a carbon atom at the α-position) indicates a carbon atom to which a benzene ring is bonded unless otherwise specified.

The term "constitutional unit derived from styrene" or "constitutional unit derived from a styrene derivative" indicates a constitutional unit formed by cleavage of an ethylenic double bond of styrene or a styrene derivative.

As the alkyl group serving as a substituent at the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated alkyl group serving as the substituent at the α-position include groups in which some or all hydrogen atoms of the above-described "alkyl group serving as the substituent at the α-position" are substituted with halogen atoms. Examples of the halogen atom include a fluorine atom, a chlorine atom, a bromine atom and an iodine atom, and a fluorine atom is particularly preferable.

Specific examples of the hydroxyalkyl group serving as the substituent at the α-position include groups in which some or all hydrogen atoms of the above-described "alkyl group serving as the substituent at the α-position" are substituted with a hydroxyl group. The number of hydroxyl groups in the hydroxyalkyl group is preferably 1 to 5, and most preferably 1.

In the present specification and the scope of the present patent claims, asymmetric carbons may be present or enantiomers or diastereomers may be present depending on the structures of the chemical formulae. In this case, these isomers are represented by one formula. These isomers may be used alone or in the form of a mixture.

(Resist Composition)

The resist composition according to the first aspect of the present invention is a resist composition which generates an acid upon exposure and whose solubility in a developing solution is changed due to an action of the acid.

As an embodiment of such a resist composition, a resist composition including a base material component (A) (hereinafter, also referred to as a "component (A)") whose solubility in a developing solution is changed due to the action of an acid, and an acid generator component (B) (hereinafter, also referred to as a "component (B)") which generates an acid upon exposure is exemplified. In the resist composition of the present embodiment, the component (B) contains a compound (B1) represented by Formula (b1).

In a case where a resist film is formed using the resist composition according to the present embodiment and the formed resist film is subjected to selective exposure, an acid is generated from the component (B) at exposed portions of the resist film, and the generated acid acts on the component (A) to change the solubility of the component (A) in a developing solution, whereas the solubility of the component (A) in a developing solution is not changed at unexposed portions of the resist film, thereby generating a difference in solubility in a developing solution between exposed portions and unexposed portions. Therefore, by subjecting the resist film to development, the exposed portions of the resist film are dissolved and removed to form a positive type resist pattern in a case of a positive type resist, whereas the unexposed portions of the resist film are dissolved and removed to form a negative type resist pattern in a case of a negative type resist.

In the present specification, a resist composition which forms a positive type resist pattern by dissolving and removing the exposed portions of the resist film is called a positive type resist composition, and a resist composition which forms a negative type resist pattern by dissolving and removing the unexposed portions of the resist film is called a negative type resist composition.

The resist composition of the present embodiment may be a positive type resist composition or a negative type resist composition.

Further, in the formation of a resist pattern, the resist composition of the present embodiment can be applied to an alkali developing process using an alkali developing solution in the developing treatment, or a solvent developing process using a developing solution containing an organic solvent (organic developing solution) in the developing treatment.

The resist composition of the present embodiment has a function of generating an acid upon exposure, and the component (A) may generate an acid upon exposure in addition to the component (B).

In a case where the component (A) generates an acid upon exposure, the component (A) becomes a "base material component which generates an acid upon exposure and whose solubility in a developing solution is changed due to the action of the acid".

In a case where the component (A) is a base material component which generates an acid upon exposure and whose solubility in a developing solution is changed due to the action of the acid, it is preferable that the component (A1) described below be a polymer compound which generates an acid upon exposure and whose solubility in a developing solution is changed due to the action of the acid. As such a polymer compound, a resin having a constitutional unit that generates an acid upon exposure is exemplified. As a monomer from which a constitutional unit that generates an acid upon exposure is derived, a known one can be used.

<Component (A)>

The component (A) is a base material component whose solubility in a developing solution is changed due to an action of an acid.

In the present invention, the term "base material component" indicates an organic compound capable of forming a film, and is preferably an organic compound having a molecular weight of 500 or greater. In a case where the organic compound has a molecular weight of 500 or greater, the film-forming ability is improved, and a resist pattern at a nano level can be easily formed.

Organic compound used as the base material component are broadly classified into non-polymers and polymers.

In general, as a non-polymer, any of those which have a molecular weight in the range of 500 to less than 4,000 is used. Hereinafter, "low molecular weight compound" indicates a non-polymer having a molecular weight in the range of 500 to less than 4,000.

As a polymer, any of those which have a molecular weight of 1,000 or greater is generally used. Hereinafter, "resin" or "polymeric compound" indicates a polymer having a molecular weight of 1,000 or greater.

As the molecular weight of the polymer, the weight average molecular weight in terms of the polystyrene equivalent value determined by gel permeation chromatography (GPC) is used.

In a case where the resist composition of the present embodiment is a "negative type resist composition for an alkali developing process" which forms a negative type resist pattern in an alkali developing process or a case where the resist composition is a "positive type resist composition for a solvent developing process" which forms a positive type resist pattern in a solvent developing process, a base material component (A-2) (hereinafter, referred to as a "component (A-2)") which is soluble in an alkali developing solution is preferably used as the component (A), and a crosslinking agent component is further blended with the component. In such a resist composition, for example, in a case where an acid is generated from the component (B) upon exposure, crosslinking occurs between the component (A-2) and the crosslinking agent component due to the action of the acid. As the result, the solubility in an alkali developing solution is decreased (the solubility in an organic developing solution is increased).

Accordingly, in the formation of a resist pattern, in a case where a resist film obtained by coating a support with the resist composition is selectively exposed, since the unexposed portions of the resist film are soluble in an alkali developing solution (sparingly soluble in an organic developing solution) and the state is not changed while the exposed portions of the resist film become sparingly soluble in an alkali developing solution (soluble in an organic developing solution), a negative type resist pattern is formed by performing development using an alkali developing solution. Further, a positive type resist pattern is formed by performing development using an organic developing solution at this time.

As the component (A-2), a resin which is soluble (hereinafter, referred to as an "alkali-soluble resin") in an alkali developing solution is preferably used.

As the alkali-soluble resin, from the viewpoint of forming an excellent resist pattern with less swelling, a resin having a constitutional unit derived from at least one selected from an alkyl ester (preferably an alkyl ester having 1 to 5 carbon atoms) of an α-(hydroxyalkyl)acrylic acid and an alkyl ester of an α-(hydroxyalkyl)acrylic acid, disclosed in Japanese Unexamined Patent Application, First Publication No. 2000-206694; an acrylic resin or a polycycloolefin resin which contains a sulfonamide group and in which a hydrogen atom bonded to the carbon atom at the α-position may be substituted with a substituent, disclosed in U.S. Pat. No. 6,949,325; an acrylic resin which has a fluorinated alcohol and in which a hydrogen atom bonded to the carbon atom at the α-position may be substituted with a substituent, disclosed in U.S. Pat. No. 6,949,325, Japanese Unexamined Patent Application, First Publication No. 2005-336452, and Japanese Unexamined Patent Application, First Publication No. 2006-317803; and a polycycloolefin resin which has a fluorinated alcohol, disclosed in Japanese Unexamined Patent Application, First Publication No. 2006-259582 are preferable.

Further, the α-(hydroxyalkyl)acrylic acid indicates one or both of acrylic acid formed by a hydrogen atom being bonded to the carbon atom at the α-position to which a carboxy group is bonded and α-hydroxyalkylacrylic acid formed by a hydroxyalkyl group (preferably a hydroxyalkyl group having 1 to 5 carbon atoms) being bonded to the carbon atom at the α-position, among acrylic acids in which a hydrogen atom bonded to the carbon atom at the α-position may be substituted with a substituent.

From the viewpoint of easily forming an excellent resist pattern with less swelling, it is preferable that an amino-based crosslinking agent such as glycoluril containing a methylol group or an alkoxymethyl group or a melamine-based crosslinking agent be used as the crosslinking agent component. The amount of the crosslinking agent to be blended is preferably in a range of 1 to 50 parts by mass with respect to 100 parts by mass of the alkali-soluble resin.

In a case where the resist composition of the present embodiment is a "positive type resist composition for an alkali developing process" which forms a positive type resist pattern in an alkali developing process or a case where the resist composition is a "negative type resist composition for a solvent developing process" which forms a negative type resist pattern in a solvent developing process, a base material component (A-1) (hereinafter, referred to as a "component (A-1)") whose polarity is increased due to the action of an acid is preferably used as the component (A). In the alkali developing process and the solvent developing process, since the polarity of the base material component before and after the exposure is changed by using the component (A-1), an excellent development contrast between exposed portions and unexposed portions can be obtained.

In a case of applying an alkali developing process, the component (A-1) is substantially insoluble in an alkali developing solution prior to exposure, but in a case where an acid is generated from the component (B) upon exposure, the action of this acid causes an increase in the polarity of the base material component, thereby increasing the solubility of the component (A) in an alkali developing solution. Therefore, in the formation of a resist pattern, by conducting selective exposure of a resist film formed by applying the resist composition to a substrate, the exposed portions of the resist film change from an insoluble state to a soluble state in an alkali developing solution, whereas the unexposed portions of the resist film remain insoluble in an alkali developing solution, and hence, a positive type resist pattern is formed by alkali developing.

Meanwhile, in a case of a solvent developing process, the component (A-1) exhibits high solubility in an organic developing solution prior to exposure, and in a case where an acid is generated from the component (B) upon exposure, the polarity of the component (A) is increased by the action of the generated acid, thereby decreasing the solubility of the component (A) in an organic developing solution. Therefore, in the formation of a resist pattern, by conducting selective exposure of a resist film formed by applying the resist composition to a substrate, the exposed portions of the resist film change from an soluble state to an insoluble state in an organic developing solution, whereas the unexposed portions of the resist film remain soluble in an organic developing solution. As a result, by conducting development using an organic developing solution, a contrast between the exposed portions and the unexposed portions can be made, and a negative type resist pattern can be formed.

In the resist composition of the present embodiment, it is preferable that the component (A) be the component (A-1). In other words, it is preferable that the resist composition of the present embodiment be a "positive type resist composition for an alkali developing process" which forms a positive type resist pattern in an alkali developing process or a "negative type resist composition for a solvent developing process" which forms a negative type resist pattern in a solvent developing process.

A polymer compound and/or a low molecular weight compound is used as the compound (A).

In a case where the component (A) is a compound (A-1), it is preferable that, as the component (A-1), the resist composition contain preferably a polymer compound and more preferably a polymer compound (A1) (hereinafter, also referred to as a "component (A1)") having a constitutional unit which contains an acid decomposable group whose polarity is increased due to the action of an acid.

It is preferable that a polymer compound that has a constitutional unit (a2) containing a lactone-containing cyclic group, a —SO2-containing cyclic group, or a carbonate-containing cyclic group in addition to the constitutional unit (a1) be used as the component (A1).

Further, it is preferable that a polymer compound that has a constitutional unit (a3) (here, a constitutional unit corresponding to the constitutional unit (a1) or the constitutional unit (a2) is excluded) containing a polar group-containing aliphatic hydrocarbon group in addition to the constitutional unit (a1) or in addition to the constitutional unit (a1) and the constitutional unit (a2) be used as the component (A1).

In addition, as the component (A1), a constitutional unit (a4) that contains an acid undissociable aliphatic cyclic group or a constitutional unit that generates an acid upon exposure other than the constitutional units (a1) to (a3) may also be used.

<<Constitutional Unit (a1)>>

The constitutional unit (a1) is a constitutional unit that contains an acid decomposable group whose polarity is increased due to the action of an acid.

The term "acid decomposable group" indicates a group in which at least a part of a bond in the structure of the acid decomposable group can be cleaved due to the action of an acid.

Examples of the acid decomposable group whose polarity is increased due to the action of an acid include groups which are decomposed due to the action of an acid to generate a polar group.

Examples of the polar group include a carboxy group, a hydroxyl group, an amino group, and a sulfo group (—$SO_3H$). Among these, a polar group containing —OH in the structure thereof (hereinafter, also referred to as an "OH-containing polar group") is preferable, a carboxy group or a hydroxyl group is more preferable, and a carboxy group is particularly preferable.

More specific examples of the acid decomposable group include a group in which the above-described polar group has been protected with an acid dissociable group (such as a group in which a hydrogen atom of the OH-containing polar group has been protected with an acid dissociable group).

Here, the "acid dissociable group" indicates both (i) a group in which a bond between the acid dissociable group and an atom adjacent to the acid dissociable group can be cleaved due to the action of an acid; and (ii) a group in which some bonds are cleaved due to the action of an acid, and then a decarboxylation reaction occurs, thereby cleaving the bond between the acid dissociable group and the atom adjacent to the acid dissociable group.

It is necessary for the acid dissociable group that constitutes the acid decomposable group to be a group which exhibits a lower polarity than the polar group generated by the dissociation of the acid dissociable group. Thus, in a case where the acid dissociable group is dissociated by the action of an acid, a polar group exhibiting a polarity higher than that of the acid dissociable group is generated, thereby increasing the polarity. As a result, the polarity of the entire component (A1) is increased. By the increase in the polarity, the relative solubility in a developing solution changes, and the solubility in an alkali developing solution is increased, whereas the relative solubility in an organic developing solution is decreased.

Examples of the acid dissociable group are the same as those which have been proposed as acid dissociable groups for the base resin for a chemically amplified resist composition.

Specific examples of acid dissociable groups of the base resin for a conventional chemically amplified resist composition include an "acetal type acid dissociable group", a "tertiary alkyl ester type acid dissociable group", and a "tertiary alkyloxycarbonyl acid dissociable group" described below.

Acetal Type Acid Dissociable Group:

Examples of the acid dissociable group for protecting a carboxy group or a hydroxyl group serving as a polar group include the acid dissociable group represented by Formula (a1-r-1) shown below (hereinafter, also referred to as an "acetal type acid dissociable group").

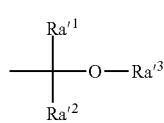
(a1-r-1)

[In the formula, $Ra'^1$ and $Ra'^2$ represent a hydrogen atom or an alkyl group, and $Ra'^3$ represents a hydrocarbon group, provided that $Ra'^3$ may be bonded to $Ra'^1$ or $Ra'^2$.]

In Formula (a1-r-1), it is preferable that at least one of $Ra'^1$ and $Ra'^2$ represent a hydrogen atom and more preferable that both of $Ra'^1$ and $Ra'^2$ represent a hydrogen atom.

In a case where $Ra'^1$ or $Ra'^2$ represents an alkyl group, examples of the alkyl group include the same alkyl groups exemplified as the substituent which may be bonded to the carbon atom at the α-position in the description of the α-substituted acrylic acid ester. Among these, an alkyl group having 1 to 5 carbon atoms is preferable. Specific examples thereof include linear or branched alkyl groups. Specific examples of the alkyl group include a methyl group, an ethyl group, a propyl group, an isopropyl group, an n-butyl group, an isobutyl group, a tert-butyl group, a pentyl group, an isopentyl group, and a neopentyl group. Among these, a methyl group or an ethyl group is preferable, and a methyl group is particularly preferable.

In Formula (a1-r-1), examples of the hydrocarbon group of $Ra'^3$ include a linear or branched alkyl group and a cyclic hydrocarbon group.

The linear alkyl group preferably has 1 to 5 carbon atoms, more preferably 1 to 4, and still more preferably 1 or 2. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl group preferably has 3 to 10 carbon atoms and more preferably 3 to 5 carbon atoms. Specific examples thereof include an isopropyl group, an isobutyl group, a tert-butyl group, an isopentyl group, a neopentyl group a 1,1-diethylpropyl group, and a 2,2-dimethylbutyl group. Among these, an isopropyl group is preferable.

In a case where $Ra'^3$ represents a cyclic hydrocarbon group, the cyclic hydrocarbon group may be an aliphatic hydrocarbon group or an aromatic hydrocarbon group, and may be polycyclic or monocyclic.

As the aliphatic hydrocarbon group which is a monocyclic group, a group in which one hydrogen atom has been removed from a monocycloalkane is preferable. The monocycloalkane preferably has 3 to 6 carbon atoms, and specific examples thereof include cyclopentane and cyclohexane.

As the aliphatic hydrocarbon group which is a polycyclic group, a group in which one hydrogen atom has been removed from a polycycloalkane is preferable. As the polycycloalkane, a group having 7 to 12 carbon atoms is preferable, and specific examples of the polycycloalkane include adamantane, norbornane, isobornane, tricyclodecane, and tetracyclododecane.

In a case where the cyclic hydrocarbon group of $Ra'^3$ becomes an aromatic hydrocarbon group, the aromatic hydrocarbon group is a hydrocarbon group having at least one aromatic ring.

The aromatic ring is not particularly limited as long as it is a cyclic conjugated system having $(4n+2)\pi$ electrons, and may be monocyclic or polycyclic. The aromatic ring preferably has 5 to 30 carbon atoms, more preferably 5 to 20 carbon atoms, still more preferably 6 to 15 carbon atoms, and most preferably 6 to 12 carbon atoms. Here, the number of carbon atoms in a substituent is not included in the number of carbon atoms. Specific examples of the aromatic ring include aromatic hydrocarbon rings such as benzene, naphthalene, anthracene, and phenanthrene; and aromatic hetero rings in which some carbon atoms constituting the above-described aromatic hydrocarbon rings have been substituted with hetero atoms. Examples of the hetero atom in the aromatic hetero rings include an oxygen atom, a sulfur atom, and a nitrogen atom. Specific examples of the aromatic hetero ring include a pyridine ring and a thiophene ring.

Specific examples of the aromatic hydrocarbon group of $Ra'^3$ include a group in which one hydrogen atom has been removed from the above-described aromatic hydrocarbon ring or aromatic hetero ring (an aryl group or a heteroaryl group); a group in which one hydrogen atom has been removed from an aromatic compound having two or more aromatic rings (biphenyl, fluorene or the like); and a group in which one hydrogen atom of the above-described aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group which is bonded to the above-described aromatic hydrocarbon ring or aromatic hetero ring preferably has 1 to 4 carbon atoms, more preferably 1 or 2 carbon atoms, and particularly preferably 1 carbon atom.

In a case where $Ra'^3$ is bonded to $Ra'^1$ or $Ra'^2$ to form a ring, the cyclic group is preferably a 4- to 7-membered ring, and more preferably a 4- to 6-membered ring. Specific examples of the cyclic group include a tetrahydropyranyl group and a tetrahydrofuranyl group.

Tertiary Alkyl Ester Type Acid Dissociable Group:

Examples of the acid dissociable group for protecting the carboxy group serving as a polar group include the acid dissociable group represented by Formula (a1-r-2) shown below. Among the acid dissociable groups represented by Formula (a1-r-2), for convenience, a group which is constituted of alkyl groups is referred to as a "tertiary alkyl ester type acid dissociable group".

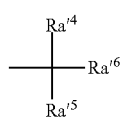
(a1-r-2)

[In the formula, $Ra'^4$ to $Ra'^6$ each independently represent a hydrocarbon group, provided that $Ra'^5$ and $Ra'^6$ may be mutually bonded to form a ring.]

Examples of the hydrocarbon group of $Ra'^4$ to $Ra'^6$ are the same as those exemplified as $Ra'^3$.

It is preferable that $Ra'^4$ represent an alkyl group having 1 to 5 carbon atoms. In a case where $Ra'^5$ and $Ra'^6$ are bonded to each other to form a ring, a group represented by Formula (a1-r2-1) shown below can be exemplified. On the other hand, in a case where Ra'⁴ to Ra'⁶ are not bonded to each other and independently represent a hydrocarbon group, a group represented by Formula (a1-r2-2) shown below can be exemplified.

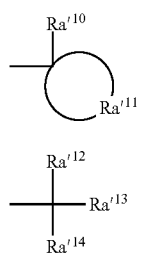

(a1-r2-1)

(a1-r2-2)

[In the formulae, Ra'¹⁰ represents an alkyl group having 1 to 10 carbon atoms, Ra'¹¹ represents a group that forms an aliphatic cyclic group together with a carbon atom to which Ra'¹⁰ is bonded, and Ra'¹² to Ra'¹⁴ each independently represent a hydrocarbon group.]

In Formula (a1-r2-1), as the alkyl group having 1 to 10 carbon atoms of Ra'¹⁰, the same groups as described above for the linear or branched alkyl group of Ra'³ in Formula (a1-r-1) are preferable. In Formula (a1-r2-1), as the aliphatic cyclic group that is formed by Ra'¹¹ together with the carbon atom to which Ra'¹⁰ is bonded, the same groups as those described above for the monocyclic or polycyclic aliphatic hydrocarbon group of Ra'³ in Formula (a1-r-1) are preferable.

In Formula (a1-r2-2), it is preferable that Ra'¹² and Ra'¹⁴ each independently represent an alkyl group having 1 to 10 carbon atoms, and it is more preferable that the alkyl group be the same group as described above for the linear or branched alkyl group of Ra'³ in Formula (a1-r-1), it is still more preferable that the alkyl group be a linear alkyl group having 1 to 5 carbon atoms, and it is particularly preferable that the alkyl group be a methyl group or an ethyl group.

In Formula (a1-r2-2), it is preferable that Ra'¹³ be the same group as described above for the linear or branched alkyl group or monocyclic or polycyclic alicyclic hydrocarbon group of Ra'³ in Formula (a1-r-1). Among these examples, a group exemplified as the aliphatic hydrocarbon group which is a monocyclic group or a polycyclic group of Ra'³ is more preferable.

Specific examples of the group represented by Formula (a1-r2-1) are shown below. The symbol "*" represents a bonding site (in the present specification, the same applies hereinafter).

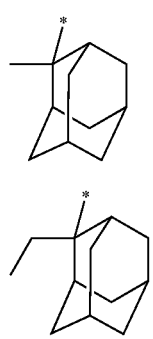

(r-pm-m1)

(r-pm-m2)

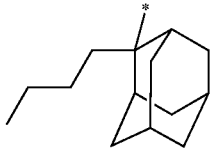

(r-pm-m3)

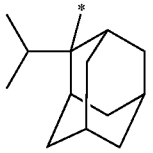

(r-pm-m4)

(r-pm-m5)

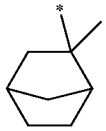

(r-pm-m6)

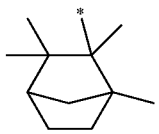

(r-pm-m7)

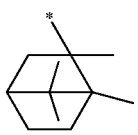

(r-pm-m8)

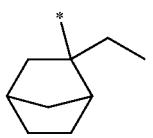

(r-pm-m9)

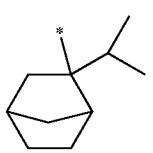

(r-pm-m10)

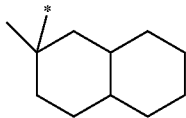

(r-pm-m11)

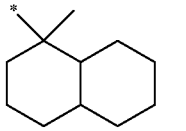

(r-pm-m12)

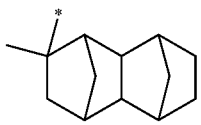

(r-pm-m13)

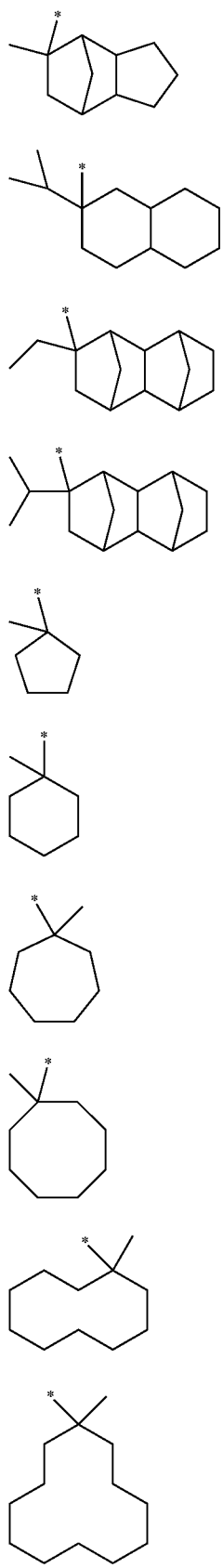
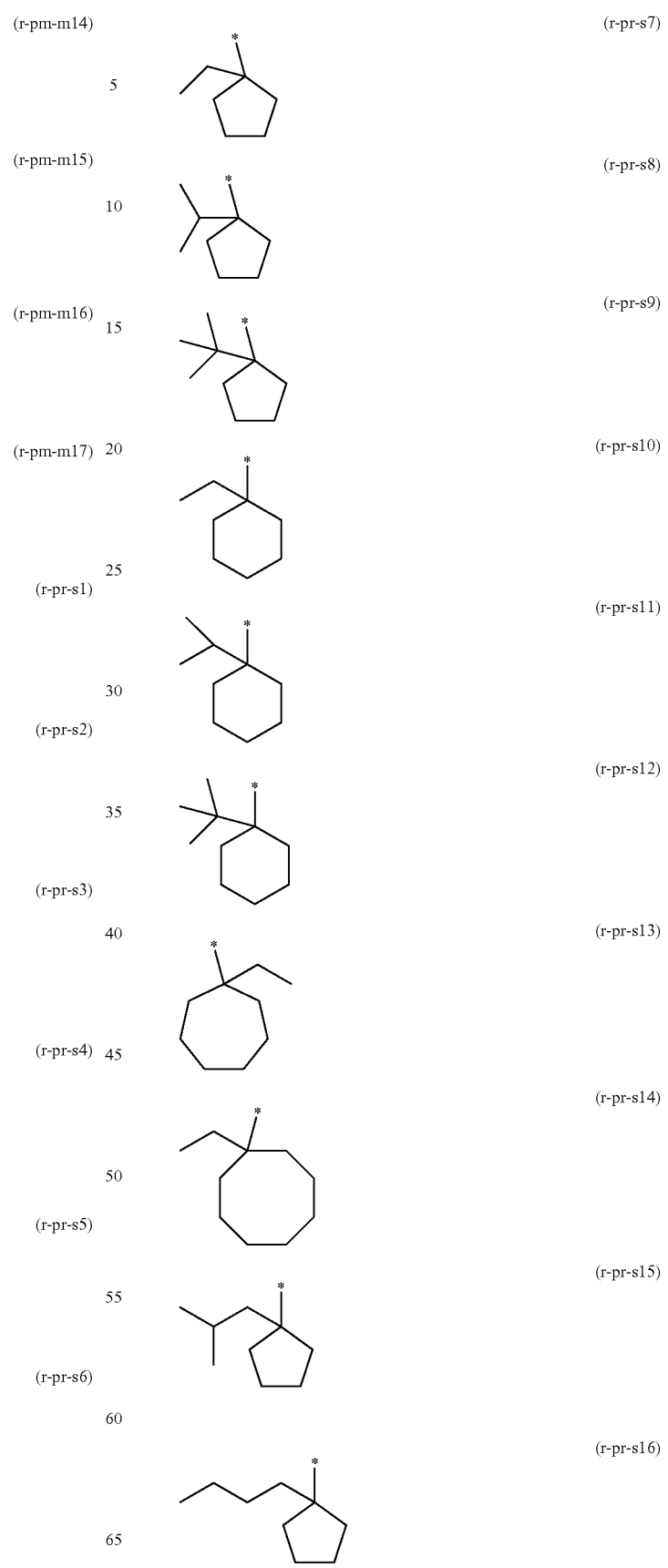

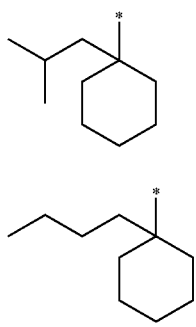
Specific examples of the group represented by Formula (a1-r2-2) are shown below.
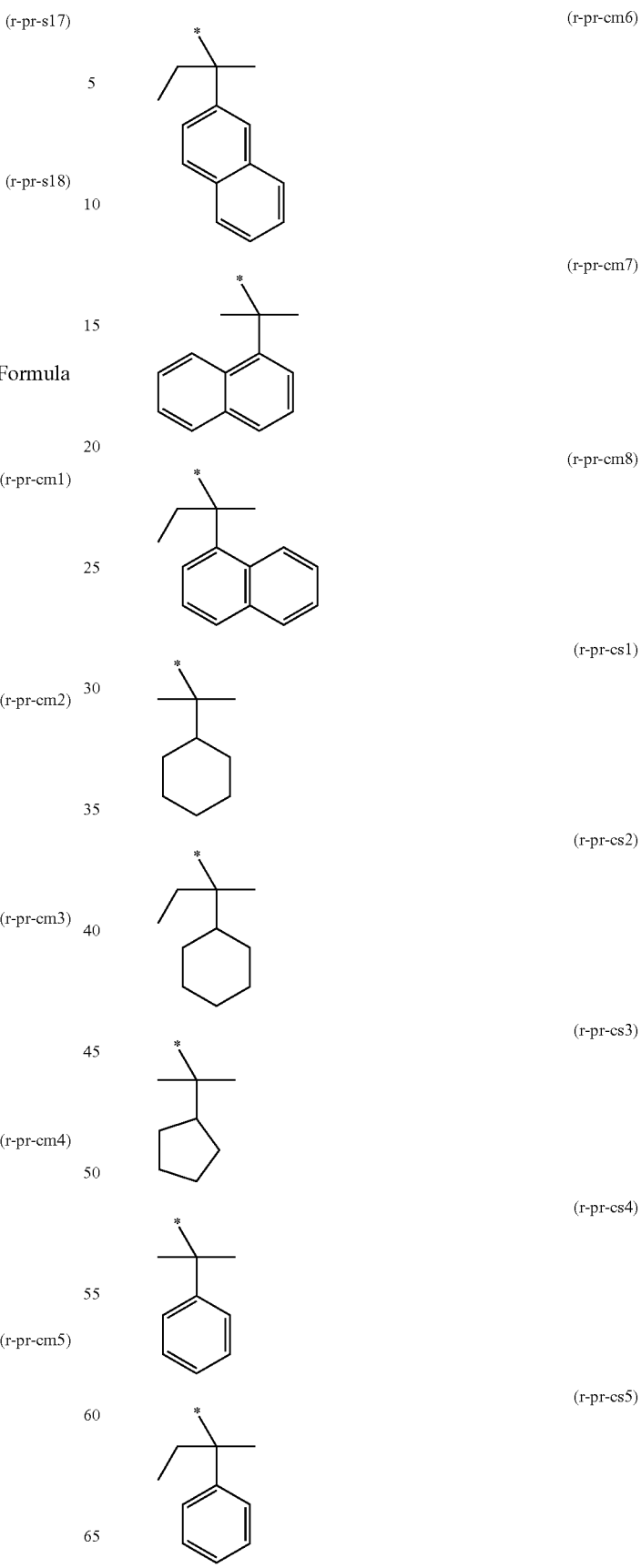

(r-pr-c1)

(r-pr-c2)

(r-pr-c3)

Tertiary Alkyloxycarbonyl Acid Dissociable Group

Examples of the acid dissociable group for protecting a hydroxyl group serving as a polar group include an acid dissociable group (hereinafter, for convenience, also referred to as a "tertiary alkyloxycarbonyl type acid dissociable group") represented by Formula (a1-r-3) shown below.

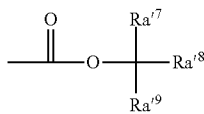

(a1-r-3)

[In the formula, $Ra'^7$ to $Ra'^9$ each independently represent an alkyl group.]

In Formula (a1-r-3), $Ra'^7$ to $Ra'^9$ preferably each independently represent an alkyl group having 1 to 5 carbon atoms and more preferably an alkyl group having 1 to 3 carbon atoms.

Further, the total number of carbon atoms in each alkyl group is preferably in a range of 3 to 7, more preferably in a range of 3 to 5, and most preferably 3 or 4.

Examples of the constitutional unit (a1) include a constitutional unit derived from an acrylic acid ester in which the hydrogen atom bonded to the carbon atom at the α-position may be substituted with a substituent; a constitutional unit derived from acrylamide; a constitutional unit in which at least some hydrogen atoms in a hydroxyl group of a constitutional unit derived from hydroxystyrene or a hydroxystyrene derivative are protected by an acid decomposable group; and a constitutional unit in which some hydrogen atoms in —C(=O)—OH of a constitutional unit derived from vinylbenzoic acid or a vinylbenzoic acid derivative are protected by an acid decomposable group.

Among the examples, as the constitutional unit (a1), a constitutional unit derived from an acrylic acid ester in which the hydrogen atom bonded to the carbon atom at the α-position may be substituted with a substituent is preferable.

Specific preferred examples of such a constitutional unit (a1) include constitutional units represented by Formula (a1-1) or (a1-2) shown below.

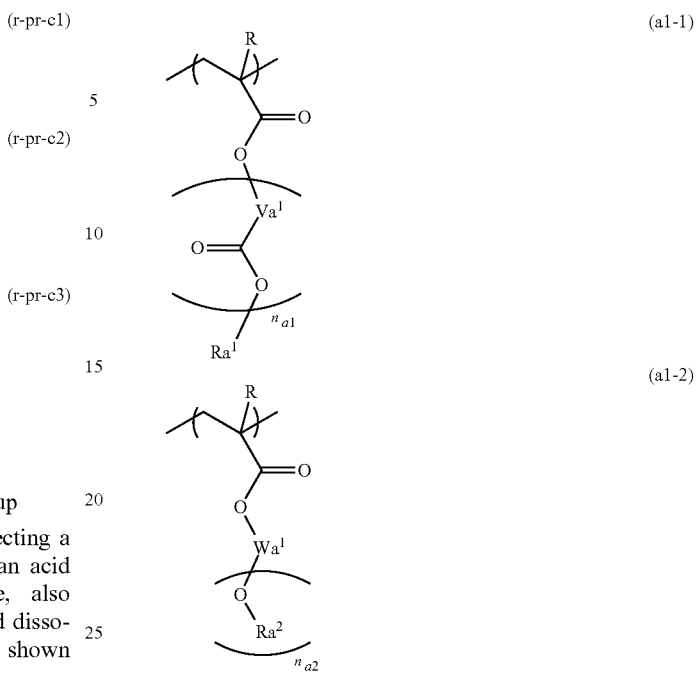

[In the formulae, R represents a hydrogen atom, an alkyl group having 1 to 5 carbon atoms, or a halogenated alkyl group having 1 to 5 carbon atoms, $Va^1$ represents a divalent hydrocarbon group which may contain an ether bond, $n_{a1}$ represents an integer of 0 to 2, and $Ra^1$ represents an acid dissociable group represented by Formula (a1-r-1) or (a1-r-2). $Wa^1$ represents a $(n_{a2}+1)$-valent hydrocarbon group, $n_{a2}$ represents an integer of 1 to 3, and $Ra^2$ represents an acid dissociable group represented by Formula (a1-r-1) or (a1-r-3)].

In Formula (a1-1), as the alkyl group having 1 to 5 carbon atoms of R, a linear or branched alkyl group having 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group in which some or all hydrogen atoms of the above-described alkyl group having 1 to 5 carbon atoms have been substituted with halogen atoms. Examples of the halogen atom include a fluorine atom, a chlorine atom, a bromine atom, and an iodine atom, and a fluorine atom is particularly preferable. As R, a hydrogen atom, an alkyl group having 1 to 5 carbon atoms, or a fluorinated alkyl group having 1 to 5 carbon atoms is preferable, and a hydrogen atom or a methyl group is most preferable in terms of industrial availability.

In Formula (a1-1), the divalent hydrocarbon group of $Va^1$ may be an aliphatic hydrocarbon group or an aromatic hydrocarbon group.

The aliphatic hydrocarbon group serving as the divalent hydrocarbon group represented by $Va^1$ may be saturated or unsaturated. In general, the aliphatic hydrocarbon group is preferably saturated.

Specific examples of the aliphatic hydrocarbon group include a linear or branched aliphatic hydrocarbon group, and an aliphatic hydrocarbon group containing a ring in the structure thereof.

The linear or branched aliphatic hydrocarbon group preferably has 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

As the branched aliphatic hydrocarbon group, a branched alkylene group is preferred, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$— and —$CH_2CH(CH_3)CH_2$—; and alkyltetramethylene groups such as —$CH(CH_3)CH_2CH_2CH_2$— and —$CH_2CH(CH_3)CH_2CH_2$—. As the alkyl group in the alkylalkylene group, a linear alkyl group having 1 to 5 carbon atoms is preferable.

Examples of the aliphatic hydrocarbon group containing a ring in the structure thereof include an alicyclic hydrocarbon group (a group in which two hydrogen atoms have been removed from an aliphatic hydrocarbon ring), a group in which the alicyclic hydrocarbon group is bonded to the terminal of the above-described linear or branched aliphatic hydrocarbon group, and a group in which the alicyclic hydrocarbon group is interposed in the above-described linear or branched aliphatic hydrocarbon group. The linear or branched aliphatic hydrocarbon group is the same as defined for the above-described linear aliphatic hydrocarbon group or the above-described branched aliphatic hydrocarbon group.

The alicyclic hydrocarbon group preferably has 3 to 20 carbon atoms and more preferably 3 to 12 carbon atoms.

The alicyclic hydrocarbon group may be monocyclic or polycyclic. As the monocyclic alicyclic hydrocarbon group, a group in which two hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which two hydrogen atoms have been removed from a polycycloalkane is preferable. As the polycycloalkane, a group having 7 to 12 carbon atoms is preferable. Specific examples of the polycycloalkane include adamantane, norbornane, isobornane, tricyclodecane, and tetracyclododecane.

The aromatic hydrocarbon group serving as the divalent hydrocarbon group represented by $Va^1$ is a hydrocarbon group having an aromatic ring.

The aromatic hydrocarbon group preferably has 3 to 30 carbon atoms, more preferably 5 to 30 carbon atoms, still more preferably 5 to 20 carbon atoms, particularly preferably 6 to 15 carbon atoms, and most preferably 6 to 10 carbon atoms. Here, the number of carbon atoms in a substituent is not included in the number of carbon atoms.

Specific examples of the aromatic ring contained in the aromatic hydrocarbon group include aromatic hydrocarbon rings such as benzene, biphenyl, fluorene, naphthalene, anthracene, and phenanthrene; and aromatic hetero rings in which some carbon atoms constituting the above-described aromatic hydrocarbon rings have been substituted with hetero atoms. Examples of the hetero atom in the aromatic hetero rings include an oxygen atom, a sulfur atom, and a nitrogen atom.

Specific examples of the aromatic hydrocarbon group include a group in which two hydrogen atoms have been removed from the above-described aromatic hydrocarbon ring (an arylene group); and a group in which one hydrogen atom of a group (an aryl group) formed by removing one hydrogen atom from the aromatic hydrocarbon ring has been substituted with an alkylene group (a group formed by removing one more hydrogen atom from an aryl group in an arylalkyl group such as a benzyl group, a phenethyl group, a 1-naphthylmethyl group, a 2-naphthylmethyl group, a 1-naphthylethyl group, or a 2-naphthylethyl group). The alkylene group (an alkyl chain in the arylalkyl group) preferably has 1 to 4 carbon atoms, more preferably 1 or 2 carbon atoms, and particularly preferably 1 carbon atom.

In Formula (a1-2), the ($n_{a2}$+1)-valent hydrocarbon group of $Wa^1$ may be an aliphatic hydrocarbon group or an aromatic hydrocarbon group. The aliphatic hydrocarbon group indicates a hydrocarbon group that has no aromaticity, and may be saturated or unsaturated, but is preferably saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $n_{a2}$+1 is preferably divalent, trivalent or tetravalent, and divalent or trivalent is more preferable.

Specific examples of the constitutional unit represented by Formula (a1-1) are shown below.

In the formulae shown below, $R^\alpha$ represents a hydrogen atom, a methyl group, or a trifluoromethyl group.

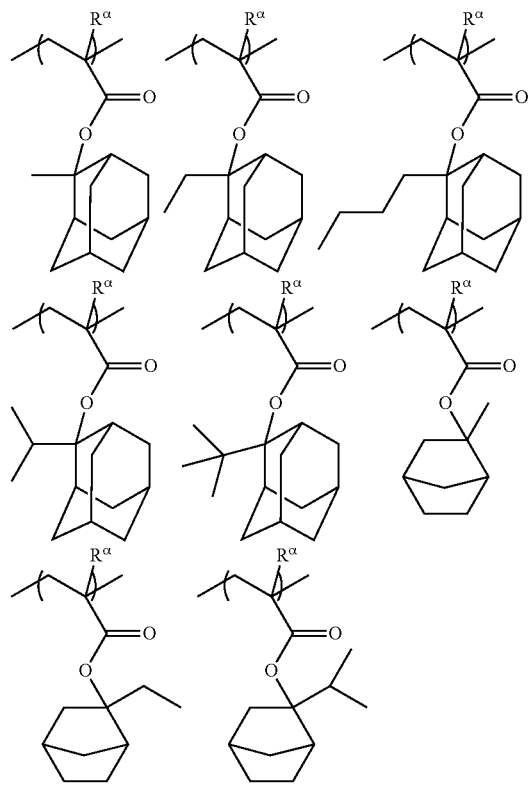

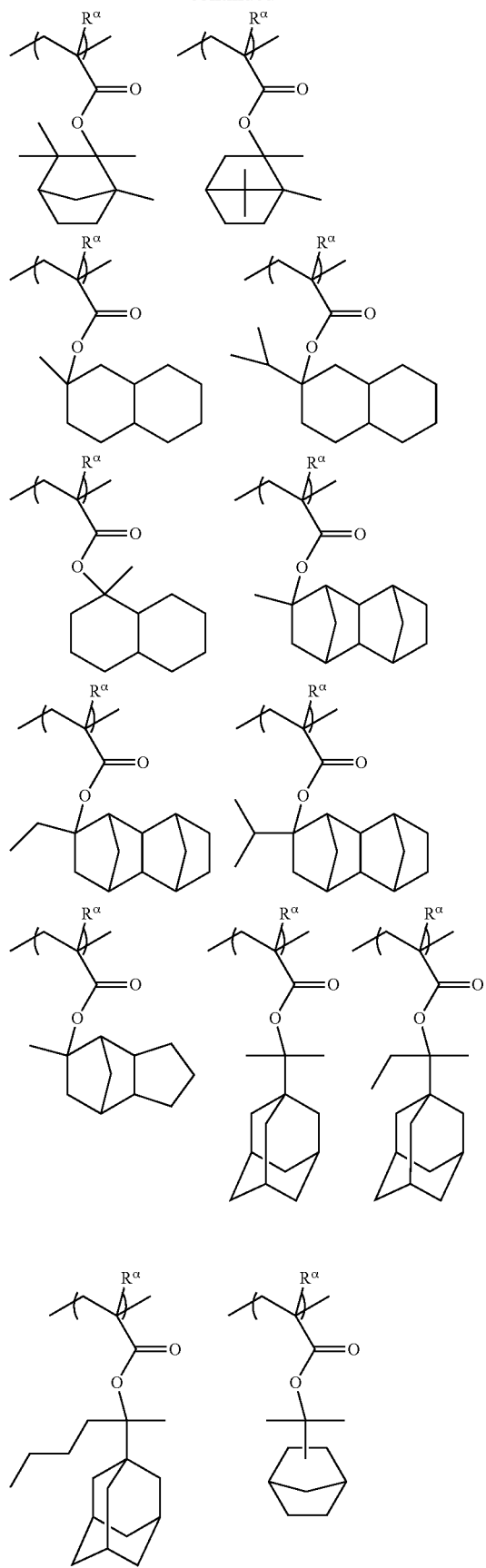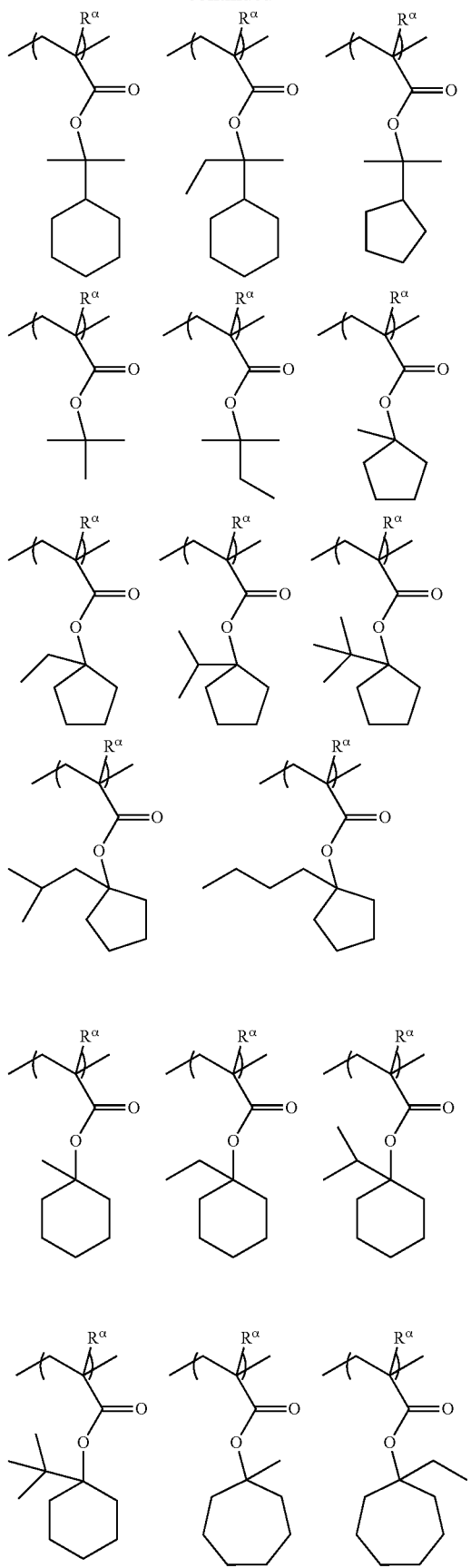

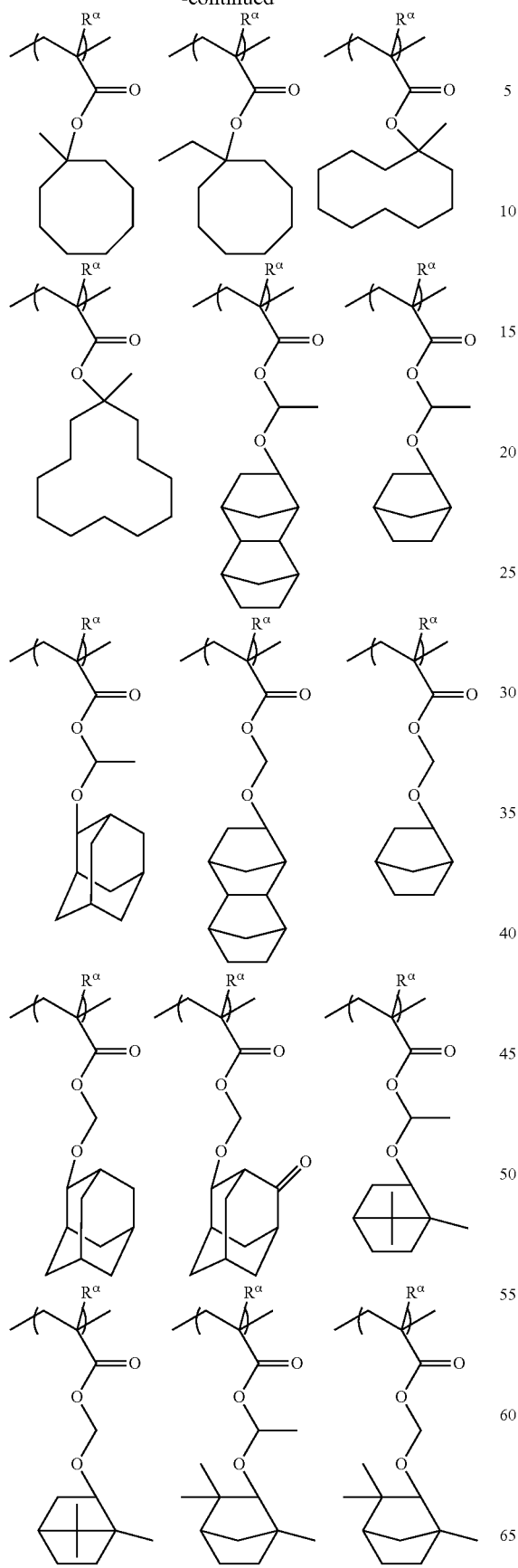
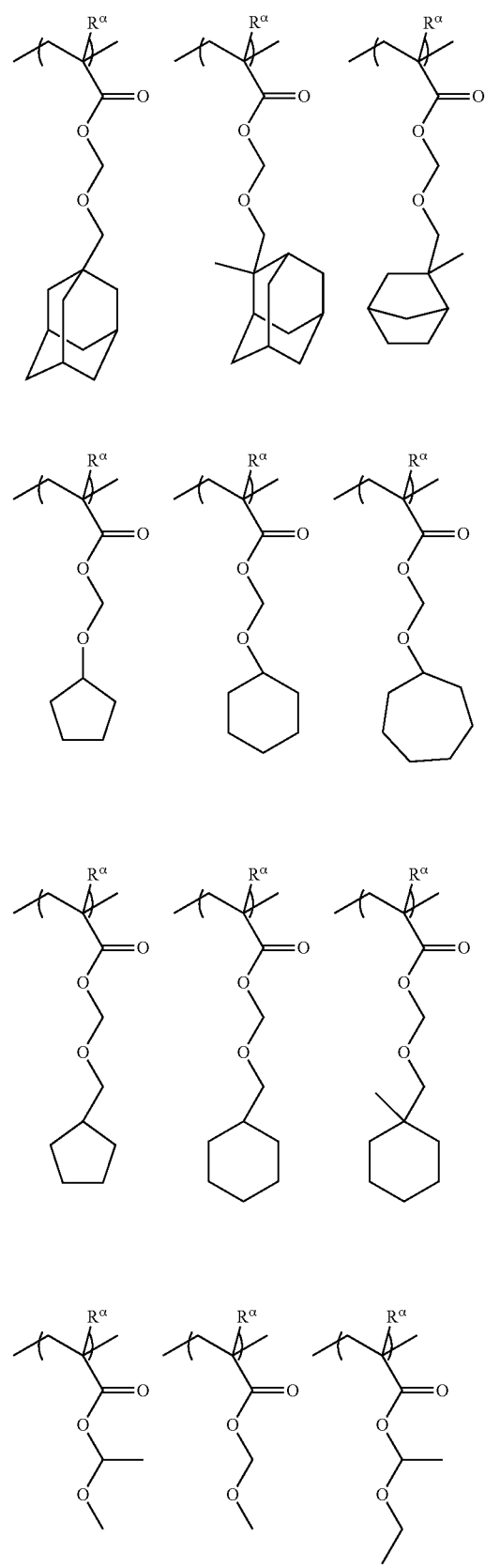

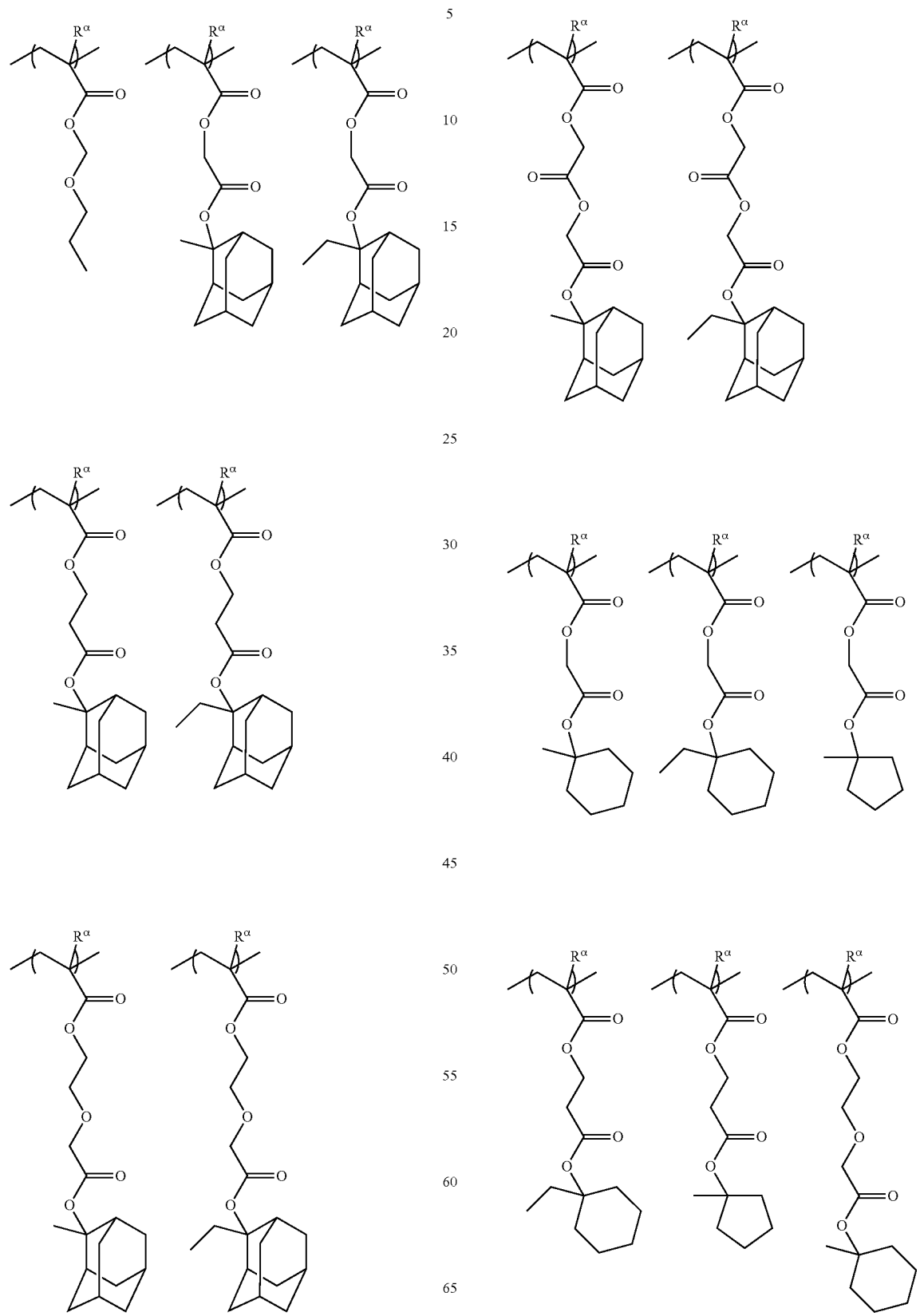

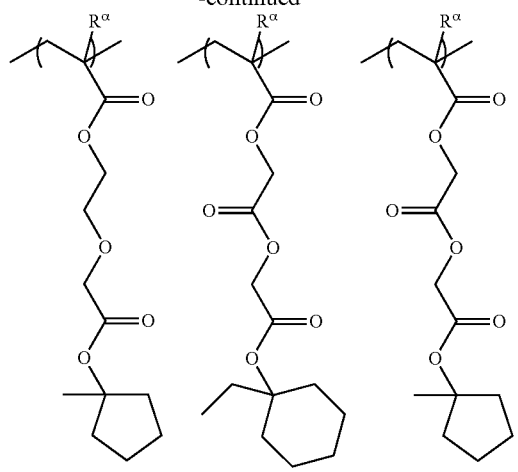

Specific examples of the constitutional unit represented by Formula (a1-2) are shown below.

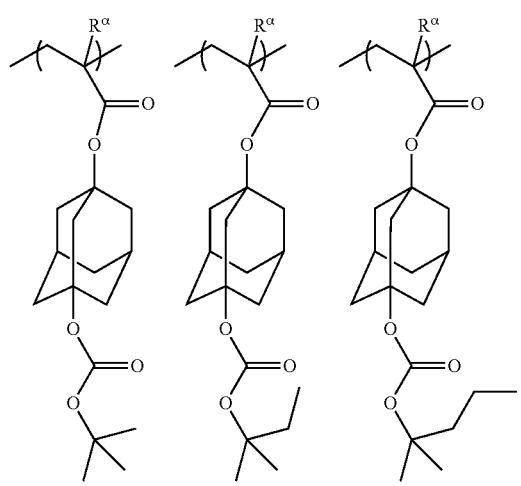

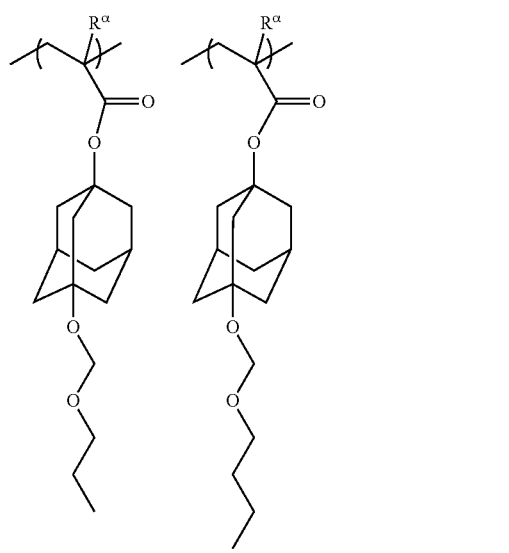

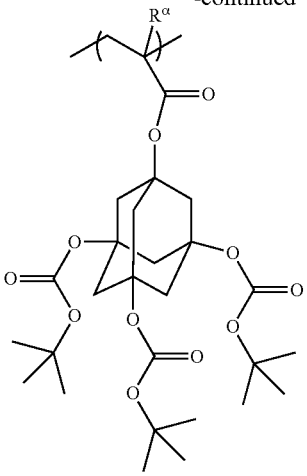

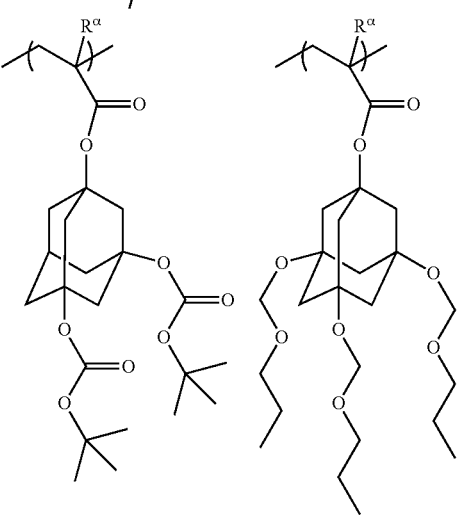

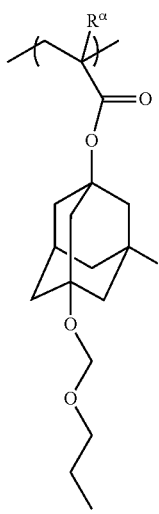

The constitutional unit (a1) included in the component (A1) may be used alone or two or more kinds thereof may be used.

The proportion of the constitutional unit (a1) in the component (A1) is preferably in a range of 5% to 60% by mole, more preferably in a range of 10% to 55% by mole, and still more preferably in a range of 20% to 50% by mole with respect to the total amount of all constitutional units constituting the component (A1).

By setting the proportion of the constitutional unit (a1) to be greater than or equal to the lower limit, a resist pattern can be easily obtained, and lithography characteristics of enhancing the sensitivity, the resolution, and the roughness, and the EL margin are improved. Further, by setting the proportion of the constitutional unit (a1) to be lower than or equal to the upper limit, the constitutional unit (a1) and other constitutional units can be balanced.

<<Constitutional Unit (a2)>>

The constitutional unit (a2) is a constitutional unit (here, a constitutional unit corresponding to the constitutional unit (a1) is excluded) containing a lactone-containing cyclic group, a —SO$_2$-containing cyclic group, or a carbonate-containing cyclic group.

In a case where the component (A1) is used for forming a resist film, the lactone-containing cyclic group, the —SO$_2$-containing cyclic group, or the carbonate-containing cyclic group in the constitutional unit (a2) is effective for improving the adhesiveness of the resist film to the substrate. Further, by virtue of including the constitutional unit (a2), in an alkali developing process, during development, the solubility of the resist film in an alkali developing solution is enhanced.

The term "lactone-containing cyclic group" indicates a cyclic group that contains a ring (lactone ring) containing a —O—C(=O)— in the ring structure. In a case where the lactone ring is counted as the first ring and the group contains only the lactone ring, the group is referred to as a monocyclic group. Further, in a case where the group has other ring structures, the group is referred to as a polycyclic group regardless of the structures. The lactone-containing cyclic group may be a monocyclic group or a polycyclic group.

The lactone-containing cyclic group for the constitutional unit (a2) is not particularly limited, and an optional constitutional unit may be used. Specific examples thereof include groups represented by Formulae (a2-r-1) to (a2-r-7) shown below.

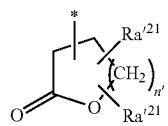
(a2-r-1)

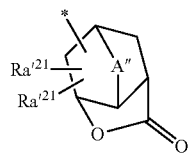
(a2-r-2)

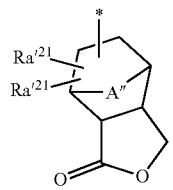
(a2-r-3)

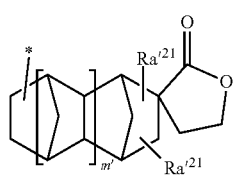
(a2-r-4)

-continued

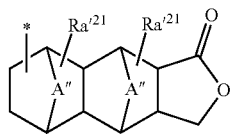
(a2-r-5)

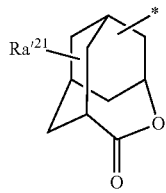
(a2-r-6)

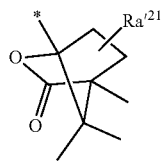
(a2-r-7)

[In the formulae, each Ra'$^{21}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; and R" represents a hydrogen atom, an alkyl group, a lactone-containing cyclic group, a carbonate-containing cyclic group, or a —SO$_2$-containing cyclic group; A" represents an oxygen atom (—O—), a sulfur atom (—S—) or an alkylene group having 1 to 5 carbon atoms which may contain an oxygen atom or a sulfur atom; n' represents an integer of 0 to 2; and m' represents 0 or 1.]

In Formulae (a2-r-1) to (a2-r-7), the alkyl group of Ra'$^{21}$ is preferably an alkyl group having 1 to 6 carbon atoms. Further, the alkyl group is preferably a linear alkyl group or a branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Among these, a methyl group or ethyl group is preferable, and a methyl group is particularly preferable.

The alkoxy group of Ra'$^{21}$ is preferably an alkoxy group having 1 to 6 carbon atoms.

Further, the alkoxy group is preferably a linear or branched alkoxy group.

Specific examples of the alkoxy groups include a group formed by linking the above-described alkyl group of Ra'$^{21}$ to an oxygen atom (—O—).

Examples of the halogen atom of Ra'$^{21}$ include a fluorine atom, a chlorine atom, a bromine atom, and an iodine atom. Among these, a fluorine atom is preferable.

Examples of the halogenated alkyl group of Ra'$^{21}$ include groups in which some or all hydrogen atoms in the above-described alkyl group of Ra'$^{21}$ have been substituted with the above-described halogen atoms. As the halogenated alkyl group, a fluorinated alkyl group is preferable, and a perfluoroalkyl group is particularly preferable.

In —COOR" and —OC(=O)R" of Ra'$^{21}$, R" represents a hydrogen atom, an alkyl group, a lactone-containing cyclic group, a carbonate-containing cyclic group, or a —SO$_2$-containing cyclic group.

The alkyl group of R" may be linear, branched, or cyclic, and preferably has 1 to 15 carbon atoms.

In a case where R" represents a linear or branched alkyl group, it is preferably an alkyl group having 1 to 10 carbon atoms, more preferably an alkyl group having 1 to 5 carbon atoms, and most preferably a methyl group or an ethyl group.

In a case where R" represents a cyclic alkyl group, the number of carbon atoms thereof is preferably in a range of 3 to 15, more preferably in a range of 4 to 12, and most preferably in a range of 5 to 10. Specific examples thereof include groups in which one or more hydrogen atoms have been removed from a monocycloalkane, which may or may not be substituted with a fluorine atom or a fluorinated alkyl group; and groups in which one or more hydrogen atoms have been removed from a polycycloalkane such as a bicycloalkane, a tricycloalkane, or a tetracycloalkane. More specific examples thereof include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane, or tetracyclododecane.

Examples of the lactone-containing cyclic group of R" include those exemplified as the groups represented by Formulae (a2-r-1) to (a2-r-7).

The carbonate-containing cyclic group of R" has the same definition as that for the carbonate-containing cyclic group described below. Specific examples of the carbonate-containing cyclic group include groups represented by Formulae (ax3-r-1) to (ax3-r-3).

The —SO$_2$-containing cyclic group of R" has the same definition as that for the —SO$_2$-containing cyclic group described below. Specific examples of the —SO$_2$-containing cyclic group include groups represented by Formulae (a5-r-1) to (a5-r-4).

The hydroxyalkyl group of Ra'$^{21}$ preferably has 1 to 6 carbon atoms, and specific examples thereof include a group in which at least one hydrogen atom in the alkyl group of Ra'$^{21}$ has been substituted with a hydroxyl group.

In Formulae (a2-r-2), (a2-r-3) and (a2-r-5), as the alkylene group having 1 to 5 carbon atoms of A", a linear or branched alkylene group is preferable, and examples thereof include a methylene group, an ethylene group, an n-propylene group, and an isopropylene group. Examples of alkylene groups that contain an oxygen atom or a sulfur atom include groups in which —O— or —S— is interposed in the terminal of the alkylene group or between the carbon atoms of the alkylene group, and examples thereof include —O—CH$_2$—, —CH$_2$—O—CH$_2$—, —S—CH$_2$—, and —CH$_2$—S—CH$_2$—. As A", an alkylene group having 1 to 5 carbon atoms or —O— is preferable, an alkylene group having 1 to 5 carbon atoms is more preferable, and a methylene group is most preferable.

Specific examples of the groups represented by Formulae (a2-r-1) to (a2-r-7) are shown below.

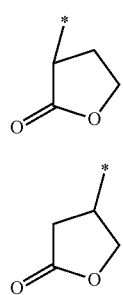

(r-lc-1-1)

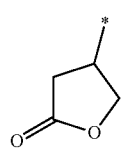

(r-lc-1-2)

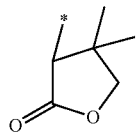

(r-lc-1-3)

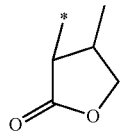

(r-lc-1-4)

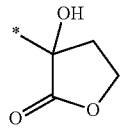

(r-lc-1-5)

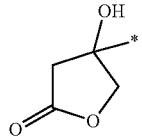

(r-lc-1-6)

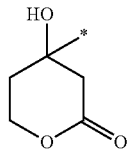

(r-lc-1-7)

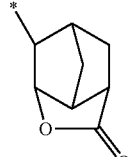

(r-lc-2-1)

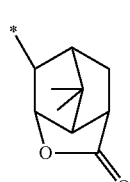

(r-lc-2-2)

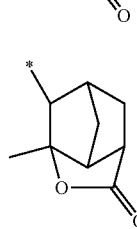

(r-lc-2-3)

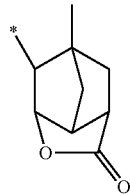

(r-lc-2-4)

(r-lc-2-5)
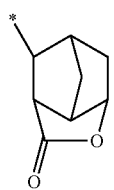
(r-lc-2-6)
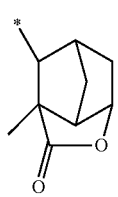
(r-lc-2-7)
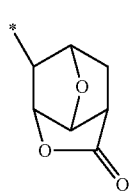
(r-lc-2-8)
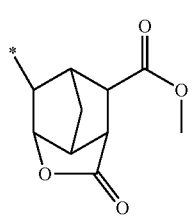
(r-lc-2-9)
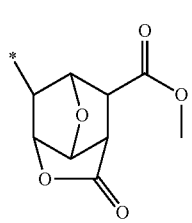
(r-lc-2-10)
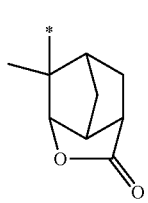
(r-lc-2-11)
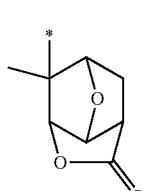
(r-lc-2-12)
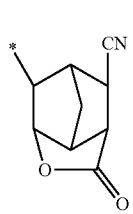
(r-lc-2-13)
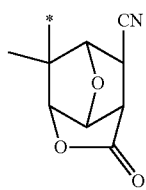
(r-lc-2-14)
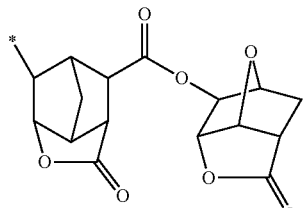
(r-lc-2-15)
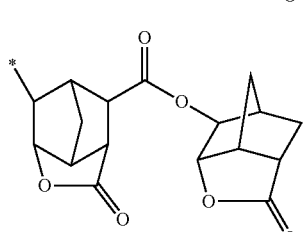
(r-lc-2-16)
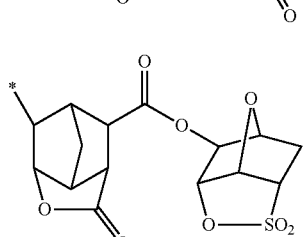
(r-lc-2-17)
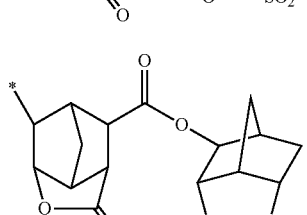
(r-lc-2-18)
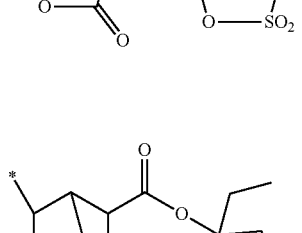
(r-lc-3-1)
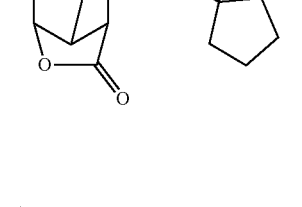
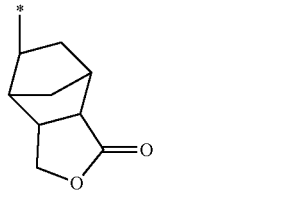

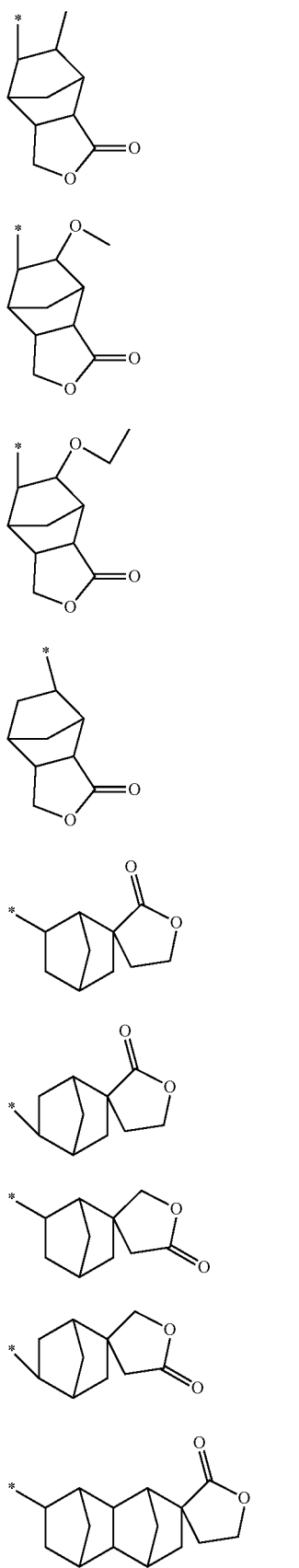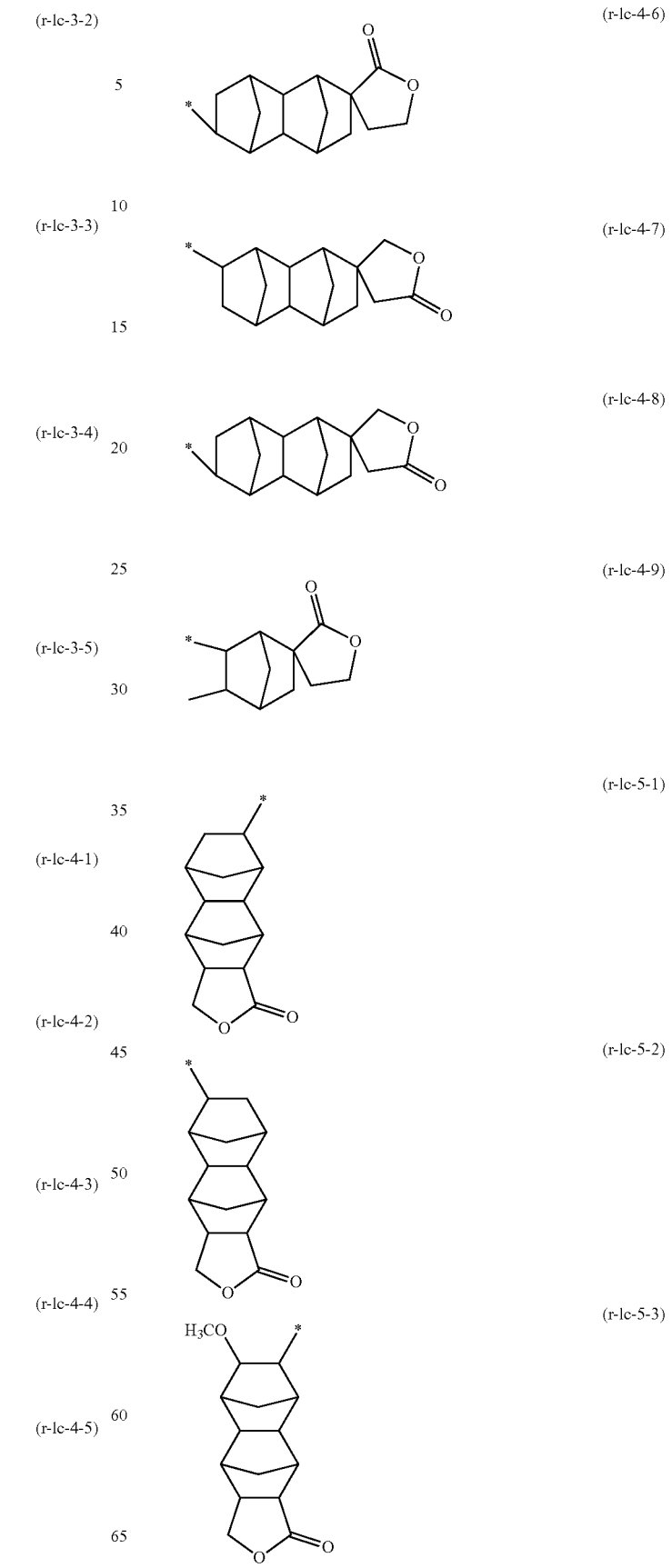

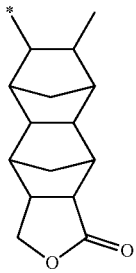
(r-lc-5-4)

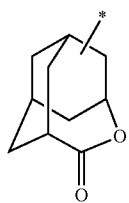
(r-lc-6-1)

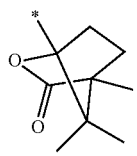
(r-lc-7-1)

The "—SO$_2$-containing cyclic group" indicates a cyclic group having a ring containing —SO$_2$— in the ring structure thereof. Specifically, the —SO$_2$-containing cyclic group is a cyclic group in which the sulfur atom (S) in —SO$_2$— forms a part of the ring skeleton of the cyclic group. In a case where the ring containing —SO$_2$— in the ring skeleton thereof is counted as the first ring and the group contains only the ring, the group is referred to as a monocyclic group. Further, in a case where the group has other ring structures, the group is referred to as a polycyclic group regardless of the structures. The —SO$_2$-containing cyclic group may be a monocyclic group or a polycyclic group.

As the —SO$_2$-containing cyclic group, a cyclic group containing —O—SO$_2$— in the ring skeleton thereof, in other words, a cyclic group containing a sultone ring in which —O—S— in the —O—SO$_2$— group forms a part of the ring skeleton thereof is particularly preferable.

More specific examples of the —SO$_2$-containing cyclic group include groups represented by Formulae (a5-r-1) to (a5-r-4) shown below.

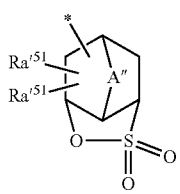
(a5-r-1)

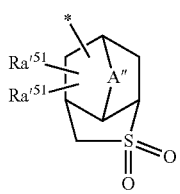
(a5-r-2)

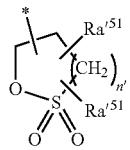
(a5-r-3)

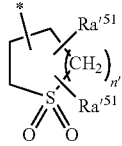
(a5-r-4)

[In the formulae, each $Ra'^{51}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group. R" represents a hydrogen atom, an alkyl group, a lactone-containing cyclic group, a carbonate-containing cyclic group, or a —SO$_2$-containing cyclic group. A" represents an oxygen atom, a sulfur atom or an alkylene group having 1 to 5 carbon atoms which may contain an oxygen atom or a sulfur atom. n' represents an integer of 0 to 2.]

In Formulae (a5-r-1) and (a5-r-2), A" has the same definition as that for A" in Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group of $Ra'^{51}$ include the same groups as those described above in the explanation of $Ra'^{21}$ in Formulae (a2-r-1) to (a2-r-7).

Specific examples of the groups represented by Formulae (a5-r-1) to (a5-r-4) are shown below. In the formulae shown below, "Ac" represents an acetyl group.

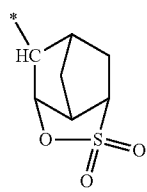
(r-s1-1-1)

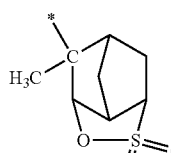
(r-s1-1-2)

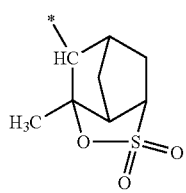
(r-s1-1-3)

-continued
(r-s1-1-4)
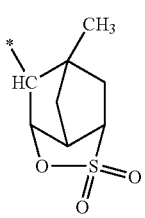
(r-s1-1-5)
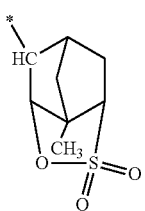
(r-s1-1-6)
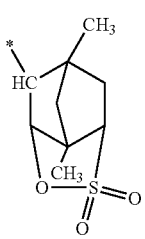
(r-s1-1-7)
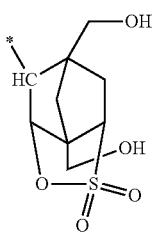
(r-s1-1-8)
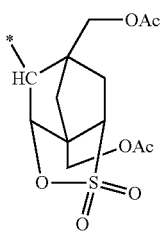
(r-s1-1-9)
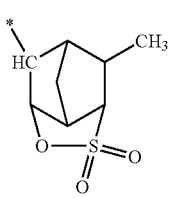
(r-s1-1-10)
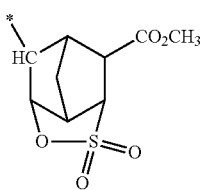
-continued
(r-s1-1-11)
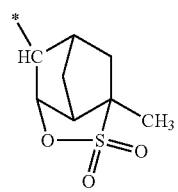
(r-s1-1-12)
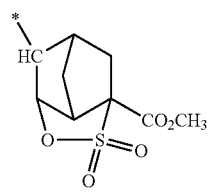
(r-s1-1-13)
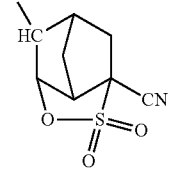
(r-s1-1-14)
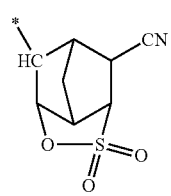
(r-s1-1-15)
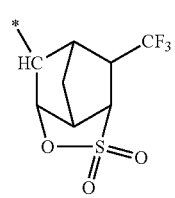
(r-s1-1-16)
(r-s1-1-17)
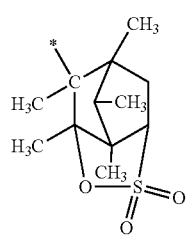
(r-s1-1-18)
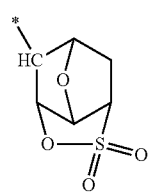

(r-s1-1-19)
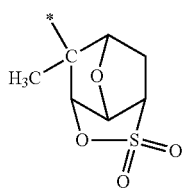
(r-s1-1-20)
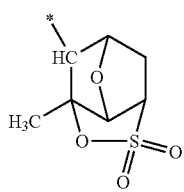
(r-s1-1-21)
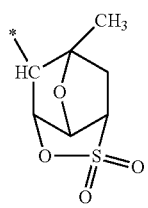
(r-s1-1-22)
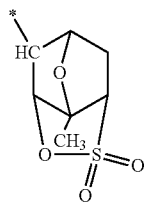
(r-s1-1-23)
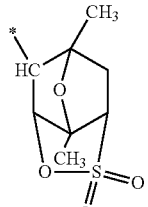
(r-s1-1-24)
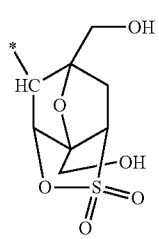
(r-s1-1-25)
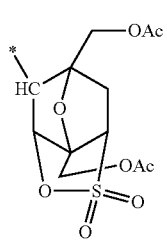
(r-s1-1-26)
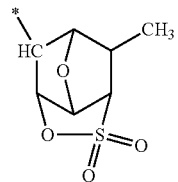
(r-s1-1-27)
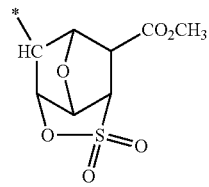
(r-s1-1-28)
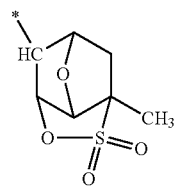
(r-s1-1-29)
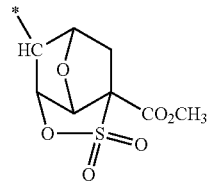
(r-s1-1-30)
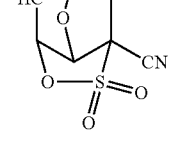
(r-s1-1-31)
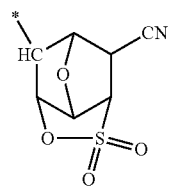
(r-s1-1-32)
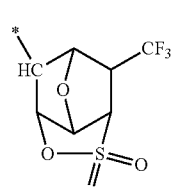
(r-s1-1-33)
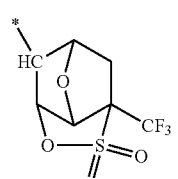

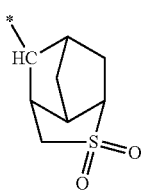
(r-s1-2-1)

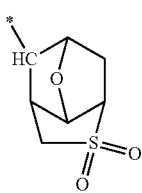
(r-s1-2-2)

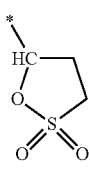
(r-s1-3-1)

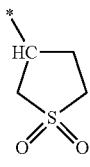
(r-s1-4-1)

The "carbonate-containing cyclic group" indicates a cyclic group having a ring (a carbonate ring) containing —O—C(=O)—O— in the ring structure thereof. In a case where the carbonate ring is counted as the first ring and the group contains only the carbonate ring, the group is referred to as a monocyclic group. Further, in a case where the group has other ring structures, the group is referred to as a polycyclic group regardless of the structures. The carbonate-containing cyclic group may be a monocyclic group or a polycyclic group.

The carbonate ring-containing cyclic group is not particularly limited, and an optional group may be used. Specific examples thereof include groups represented by Formulae (ax3-r-1) to (ax3-r-3) shown below.

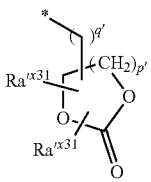
(ax3-r-1)

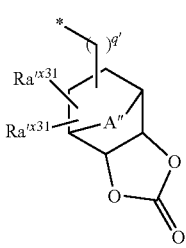
(ax3-r-2)

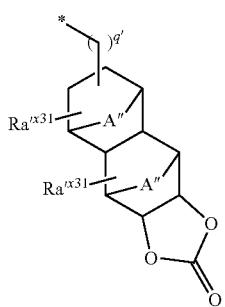
(ax3-r-3)

[In the formulae, each $Ra'^{x31}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group. R" represents a hydrogen atom, an alkyl group, a lactone-containing cyclic group, a carbonate-containing cyclic group, or a —SO₂-containing cyclic group. A" represents an oxygen atom, a sulfur atom or an alkylene group having 1 to 5 carbon atoms which may contain an oxygen atom or a sulfur atom. p' represents an integer of 0 to 3, and q' represents 0 or 1.]

In Formulae (ax3-r-2) and (ax3-r-3), A" has the same definition as that for A" in Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group of $Ra'^{x31}$ include the same groups as those described above in the explanation of $Ra'^{21}$ in Formulae (a2-r-1) to (a2-r-7).

Specific examples of the groups represented by Formulae (ax3-r-1) to (ax3-r-3) are shown below.

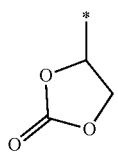
(r-cr-1-1)

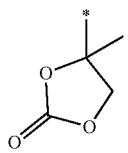
(r-cr-1-2)

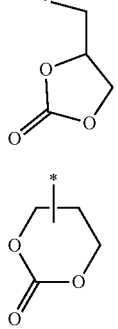
(r-cr-1-3)

(r-cr-1-4)

(r-cr-1-5)
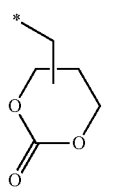
(r-cr-1-6)
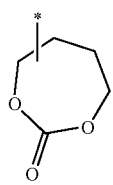
(r-cr-1-7)
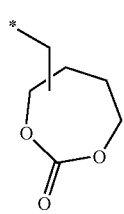
(r-cr-2-1)
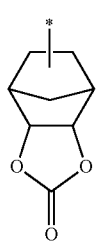
(r-cr-2-2)
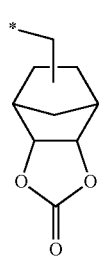
(r-cr-2-3)
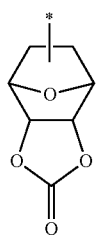
(r-cr-2-4)
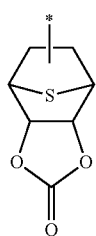
(r-cr-3-1)
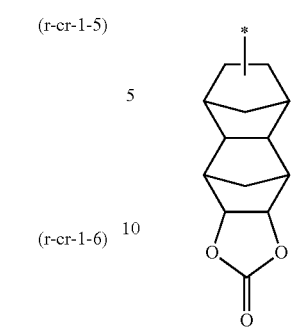
(r-cr-3-2)
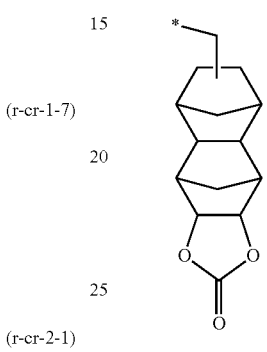
(r-cr-3-3)
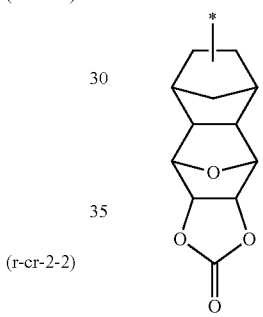
(r-cr-3-4)
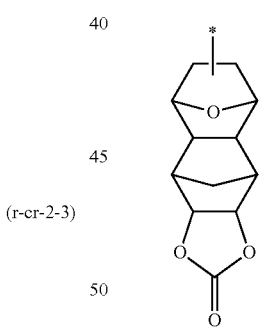
(r-cr-3-5)
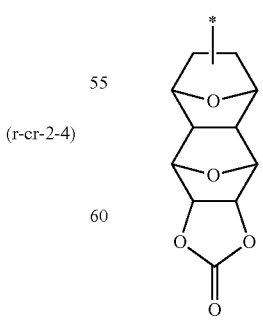
As the constitutional unit (a2), a constitutional unit derived from an acrylic acid ester in which the hydrogen atom bonded to the carbon atom at the α-position may be substituted with a substituent is preferable.

It is preferable that such a constitutional unit (a2) is a constitutional unit represented by Formula (a2-1).

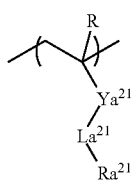

(a2-1)

In the formula, R represents a hydrogen atom, an alkyl group having 1 to 5 carbon atoms, or a halogenated alkyl group having 1 to 5 carbon atoms. $Ya^{21}$ represents a single bond or a divalent linking group. $La^{21}$ represents —O—, —COO—, —CON(R')—, —OCO—, —CONHCO— or —CONHCS—. R' represents a hydrogen atom or a methyl group; provided that, in a case where $La^{21}$ represents —O—, $Ya^{21}$ does not represents —CO—. $Ra^{21}$ represents a lactone-containing cyclic group, a carbonate-containing cyclic group, or a —$SO_2$-containing cyclic group.]

In Formula (a2-1), R has the same definition as described above.

The divalent linking group of $Ya^{21}$ is not particularly limited, and suitable examples thereof include a divalent hydrocarbon group which may have a substituent and a divalent linking group having hetero atoms.

Divalent Hydrocarbon Group which May have Substituent:

In a case where $Ya^{21}$ represents a divalent hydrocarbon group which may have a substituent, the hydrocarbon group may be an aliphatic hydrocarbon group or an aromatic hydrocarbon group.

Aliphatic Hydrocarbon Group of $Ya^{21}$

The aliphatic hydrocarbon group indicates a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof.

Linear or Branched Aliphatic Hydrocarbon Group

The linear or branched aliphatic hydrocarbon group preferably has 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$-] and a pentamethylene group [—$(CH_2)_5$—].

As the branched aliphatic hydrocarbon group, a branched alkylene group is preferred, and specific examples thereof include alkylalkylene groups, for example, alkylmethylene groups such as —CH($CH_3$)—, —CH($CH_2CH_3$)—, —C($CH_3)_2$—, —C($CH_3$)($CH_2CH_3$)—, —C($CH_3$)($CH_2CH_2CH_3$)—, and —C($CH_2CH_3)_2$—; alkylethylene groups such as —CH($CH_3$)$CH_2$—, —CH($CH_3$)CH($CH_3$)—, —C($CH_3)_2CH_2$—, —C($CH_3$)($CH_2CH_3$)$CH_2$—, and —C($CH_2CH_3)_2$—$CH_2$—; alkyltrimethylene groups such as —CH($CH_3$)$CH_2CH_2$— and —$CH_2$CH($CH_3$)$CH_2$—; and alkyltetramethylene groups such as —CH($CH_3$)$CH_2CH_2CH_2$— and —$CH_2$CH($CH_3$)$CH_2CH_2$—. As the alkyl group in the alkylalkylene group, a linear alkyl group having 1 to 5 carbon atoms is preferable.

The linear or branched aliphatic hydrocarbon group may or may not have a substituent. Examples of the substituent include a fluorine atom, a fluorinated alkyl group having 1 to 5 carbon atoms which has been substituted with a fluorine atom, and a carbonyl group.

Aliphatic Hydrocarbon Group Containing Ring in Structure Thereof

Examples of the aliphatic hydrocarbon group containing a ring in the structure thereof include a cyclic aliphatic hydrocarbon group which may have a substituent containing a hetero atom in the ring structure thereof (a group in which two hydrogen atoms have been removed from an aliphatic hydrocarbon ring), a group in which the cyclic aliphatic hydrocarbon group is bonded to the terminal of a linear or branched aliphatic hydrocarbon group, and a group in which the cyclic aliphatic hydrocarbon group is interposed in a linear or branched aliphatic hydrocarbon group. As the linear or branched aliphatic hydrocarbon group, the same groups as those described above can be used.

The cyclic aliphatic hydrocarbon group preferably has 3 to 20 carbon atoms and more preferably 3 to 12 carbon atoms.

The cyclic aliphatic hydrocarbon group may be a polycyclic group or a monocyclic group. As the monocyclic alicyclic hydrocarbon group, a group in which two hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which two hydrogen atoms have been removed from a polycycloalkane is preferable. As the polycycloalkane, a group having 7 to 12 carbon atoms is preferable. Examples of the polycycloalkane include adamantane, norbornane, isobornane, tricyclodecane, and tetracyclododecane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group serving as the substituent is preferably an alkyl group having 1 to 5 carbon atoms, and a methyl group, an ethyl group, a propyl group, an n-butyl group, or a tert-butyl group are particularly preferable.

The alkoxy group serving as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom serving as the substituent include a fluorine atom, a chlorine atom, a bromine atom, and an iodine atom, and a fluorine atom is preferable.

Examples of the halogenated alkyl group serving as the substituent include groups in which some or all hydrogen atoms in the above-described alkyl groups have been substituted with the above-described halogen atoms.

In the cyclic aliphatic hydrocarbon group, some carbon atoms constituting the ring structure thereof may be substituted with a substituent containing a hetero atom. As the substituent containing a hetero atom, —O—, —C(=O)—O—, —S—, —S(=O)$_2$—, or —S(=O)$_2$—O— is preferable.

Aromatic Hydrocarbon Group of $Ya^{21}$

The aromatic hydrocarbon group is a hydrocarbon group having at least one aromatic ring.

The aromatic ring is not particularly limited as long as it is a cyclic conjugated system having (4n+2)π electrons, and may be monocyclic or polycyclic. The aromatic ring preferably has 5 to 30 carbon atoms, more preferably 5 to 20 carbon atoms, still more preferably 6 to 15 carbon atoms, and most preferably 6 to 12 carbon atoms. Here, the number of carbon atoms in a substituent is not included in the number of carbon atoms. Specific examples of the aromatic ring include aromatic hydrocarbon rings such as benzene, naphthalene, anthracene, and phenanthrene; and aromatic hetero rings in which some carbon atoms constituting the above-described aromatic hydrocarbon rings have been substituted with hetero atoms. Examples of the hetero atom in the aromatic hetero rings include an oxygen atom, a sulfur atom, and a nitrogen atom. Specific examples of the aromatic hetero ring include a pyridine ring and a thiophene ring.

Specific examples of the aromatic hydrocarbon group include a group in which two hydrogen atoms have been removed from the above-described aromatic hydrocarbon ring or aromatic hetero ring (an arylene group or a heteroarylene group); a group in which two hydrogen atoms have been removed from an aromatic compound having two or more aromatic rings (biphenyl, fluorene or the like); and a group in which one hydrogen atom of a group formed by removing one hydrogen atom from the above-described aromatic hydrocarbon ring or aromatic hetero ring has been substituted with an alkylene group (a group in which one hydrogen atom has been removed from the aryl group in the above-described arylalkyl group such as a benzyl group, a phenethyl group, a 1-naphthylmethyl group, a 2-naphthylmethyl group, a 1-naphthylethyl group, or a 2-naphthylethyl group). The alkylene group which is bonded to the above-described aryl group or heteroaryl group preferably has 1 to 4 carbon atoms, more preferably 1 or 2 carbon atoms, and particularly preferably 1 carbon atom.

With respect to the aromatic hydrocarbon group, the hydrogen atom in the aromatic hydrocarbon group may be substituted with a substituent. For example, the hydrogen atom bonded to the aromatic ring in the aromatic hydrocarbon group may be substituted with a substituent. Examples of substituents include an alkyl group, an alkoxy group, a halogen atom, a halogenated alkyl group, and a hydroxyl group.

The alkyl group serving as the substituent is preferably an alkyl group having 1 to 5 carbon atoms, and a methyl group, an ethyl group, a propyl group, an n-butyl group, or a tert-butyl group is more preferable.

As the alkoxy group, the halogen atom, and the halogenated alkyl group serving as the substituents, the same groups as the above-described substituent groups for substituting a hydrogen atom in the cyclic aliphatic hydrocarbon group can be exemplified.

Divalent Linking Group Containing Hetero Atom

In a case where $Ya^{21}$ represents a divalent linking group containing a hetero atom, preferred examples of the linking group include —O—, —C(=O)—O—, —C(=O)—, —O—C(=O)—O—, —C(=O)—NH—, —NH—, —NH—C(=NH)— (H may be substituted with a substituent such as an alkyl group, an acyl group, or the like), —S—, —S(=O)$_2$—, —S(=O)$_2$—O—, and a group represented by Formula: —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$— [in the formulae, $Y^{21}$ and $Y^{22}$ each independently represent a divalent hydrocarbon group which may have a substituent, O represents an oxygen atom, and m" represents an integer of 0 to 3].

In a case where the divalent linking group containing a hetero atom is —C(=O)—NH—, —C(=O)—NH—C(=O)—, —NH— or —NH—C(=NH)—, H may be substituted with a substituent such as an alkyl group, an acyl group, or the like. The substituent (an alkyl group, an acyl group, or the like) preferably has 1 to 10 carbon atoms, more preferably 1 to 8 carbon atoms, and most preferably 1 to 5 carbon atoms.

In Formulae —$Y^{21}$—O—$Y^{22}$—, —$Y^{21}$—O—, —$Y^{21}$—C(=O)—O—, —C(=O)—O—$Y^{21}$—, —[$Y^{21}$—C(=O)—O]$_{m''}$—$Y^{22}$—, —$Y^{21}$—O—C(=O)—$Y^{22}$— or —$Y^{21}$—S(=O)$_2$—O—$Y^{22}$—, $Y^{21}$ and $Y^{22}$ each independently represent a divalent hydrocarbon group which may have a substituent. Examples of the divalent hydrocarbon group include the same groups as those described above as the "divalent hydrocarbon group which may have a substituent" in the explanation of the above-described divalent linking group.

As $Y^{21}$, a linear aliphatic hydrocarbon group is preferable, a linear alkylene group is more preferable, a linear alkylene group having 1 to 5 carbon atoms is still more preferable, and a methylene group or an ethylene group is particularly preferable.

As $Y^{22}$, a linear or branched aliphatic hydrocarbon group is preferable, and a methylene group, an ethylene group, or an alkylmethylene group is more preferable. The alkyl group in the alkylmethylene group is preferably a linear alkyl group having 1 to 5 carbon atoms, more preferably a linear alkyl group having 1 to 3 carbon atoms, and most preferably a methyl group.

In the group represented by Formula —[$Y^{21}$—C(=O)—O]$_{m''}$—$Y^{22}$—, m" represents an integer of 0 to 3, preferably an integer of 0 to 2, more preferably 0 or 1, and particularly preferably 1. In other words, it is particularly preferable that the group represented by Formula —[$Y^{21}$—C(=O)—O]$_{m''}$—$Y^{22}$— be a group represented by Formula —$Y^{21}$—C(=O)—O—$Y^{22}$—. Among these, a group represented by Formula —(CH$_2$)$_{a'}$—C(=O)—O—(CH$_2$)$_{b'}$— is preferable. In the formula, a' represents an integer of 1 to 10, preferably an integer of 1 to 8, more preferably an integer of 1 to 5, still more preferably 1 or 2, and most preferably 1. b' represents an integer of 1 to 10, preferably an integer of 1 to 8, more preferably an integer of 1 to 5, still more preferably 1 or 2, and most preferably 1.

As $Ya^{21}$, a single bond, an ester bond [—C(=O)—O—], an ether bond (—O—), a linear or branched alkylene group, or a combination of these is preferable.

In Formula (a2-1), $Ra^{21}$ represents a lactone-containing cyclic group, a —SO$_2$-containing cyclic group, or a carbonate-containing cyclic group.

Preferred examples of the lactone-containing cyclic group, the —SO$_2$-containing cyclic group, and the carbonate-containing cyclic group of $Ra^{21}$ include groups represented by Formulae (a2-r-1) to (a2-r-7), groups represented by Formulae (a5-r-1) to (a5-r-4), and groups represented by Formulae (ax3-r-1) to (ax3-r-3).

Among the examples, $Ra^{21}$ preferably represents a lactone-containing cyclic group or a —SO$_2$-containing cyclic group and more preferably a group represented by Formula (a2-r-1), (a2-r-2), (a2-r-6) or (a5-r-1). Specifically, a group represented by any of chemical Formulae (r-lc-1-1) to (r-lc-1-7), (r-lc-2-1) to (r-lc-2-18), (r-lc-6-1), (r-sl-1-1), and (r-sl-1-18) is still more preferable.

The constitutional unit (a2) included in the component (A1) may be used alone or two or more kinds thereof may be used.

In a case where the component (A1) has the constitutional unit (a2), the proportion of the constitutional unit (a2) in the component (A1) is preferably in a range of 1% to 80% by mole, more preferably in a range of 10% to 70% by mole, still more preferably in a range of 10% to 65% by mole, and even more preferably in a range of 10% to 60% by mole with respect to the total amount of all constitutional units constituting the component (A1).

In a case where the proportion of the constitutional unit (a2) is greater than or equal to the lower limit of the above preferable range, the effect obtained by allowing the component (A1) to contain the constitutional unit (a2) can be satisfactorily achieved. On the other hand, in a case where the proportion of the constitutional unit (a2) is less than or equal to the upper limit of the above preferable range, the constitutional unit (a2) and other constitutional units can be balanced, and various lithography characteristics and the pattern shape can be improved.

<<Constitutional Unit (a3)>>

The component (a3) is a constitutional unit (here, a constitutional unit corresponding to the above-described constitutional unit (a1) or (a2) is excluded) containing a polar group-containing resin hydrocarbon group.

In a case where the component (A1) includes the constitutional unit (a3), the hydrophilicity of the component (A1) is enhanced, and this contributes to improvement of the resolution.

Examples of the polar group include a hydroxyl group, a cyano group, a carboxyl group, or a hydroxyalkyl group in which some hydrogen atoms of the alkyl group have been substituted with fluorine atoms. Among these, a hydroxyl group is particularly preferable.

Examples of the aliphatic hydrocarbon group include linear or branched hydrocarbon groups (preferably alkylene groups) having 1 to 10 carbon atoms, and cyclic aliphatic hydrocarbon groups (cyclic groups). The cyclic group may be a monocyclic group or a polycyclic group. For example, these cyclic groups can be selected appropriately from the multitude of groups that have been proposed for the resins of resist compositions for ArF excimer lasers. The cyclic group is preferably a polycyclic group and more preferably a polycyclic group having 7 to 30 carbon atoms.

Among the examples, constitutional units derived from an acrylic acid ester that include an aliphatic polycyclic group containing a hydroxyl group, a cyano group, a carboxyl group, or a hydroxyalkyl group in which some hydrogen atoms of the alkyl group have been substituted with fluorine atoms are particularly preferable. Examples of the polycyclic group include groups in which two or more hydrogen atoms have been removed from a bicycloalkane, tricycloalkane, tetracycloalkane or the like. Specific examples thereof include groups in which two or more hydrogen atoms have been removed from a polycycloalkane such as adamantane, norbornane, isobornane, tricyclodecane or tetracyclododecane. Among these polycyclic groups, groups in which two or more hydrogen atoms have been removed from adamantane, groups in which two or more hydrogen atoms have been removed from norbornane or groups in which two or more hydrogen atoms have been removed from tetracyclododecane are preferred industrially.

The constitutional unit (a3) is not particularly limited as long as the constitutional unit contains a polar group-containing aliphatic hydrocarbon group, and an optional constitutional unit may be used.

The constitutional unit (a3) is a constitutional unit derived from an acrylic acid ester in which the hydrogen atom bonded to the carbon atom at the α-position may be substituted with a substituent, and a constitutional unit containing a polar group-containing aliphatic hydrocarbon group is preferable.

In a case where the hydrocarbon group in the polar group-containing aliphatic hydrocarbon group is a linear or branched hydrocarbon group having 1 to 10 carbon atoms, the constitutional unit (a3) is preferably a constitutional unit derived from a hydroxyethyl ester of acrylic acid. On the other hand, in a case where the hydrocarbon group is a polycyclic group, a constitutional unit represented by Formula (a3-1), a constitutional unit represented by Formula (a3-2), and a constitutional unit represented by Formula (a3-3) shown below are preferable.

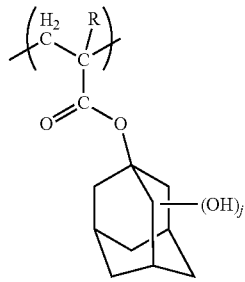

(a3-1)

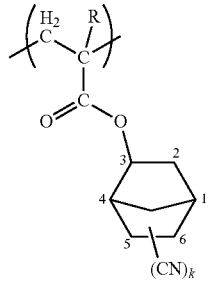

(a3-2)

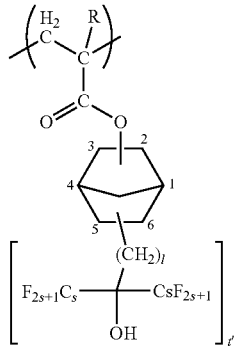

(a3-3)

[In the formulae, R has the same definition as described above, j represents an integer of 1 to 3, k represents an integer of 1 to 3, t' represents an integer of 1 to 3, l represents an integer of 1 to 5, and s represents an integer of 1 to 3.]

In Formula (a3-1), j preferably represents 1 or 2 and more preferably 1. In a case where j represents 2, it is preferable that the hydroxyl groups be bonded to the 3rd and 5th positions of the adamantyl group. In a case where j represents 1, it is preferable that the hydroxyl group be bonded to the 3rd position of the adamantyl group.

j preferably represents 1, and it is particularly preferable that the hydroxyl group be bonded to the 3rd position of the adamantyl group.

In Formula (a3-2), k preferably represents 1. The cyano group is preferably bonded to the 5th or 6th position of the norbornyl group.

In Formula (a3-3), t' preferably represents 1. 1 preferably represents 1. s preferably represents 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

The constitutional unit (a3) included in the component (A1) may be used alone or two or more kinds thereof may be used.

In a case where the component (A1) has the constitutional unit (a3), the proportion of the constitutional unit (a3) is preferably in a range of 5% to 50% by mole, more preferably in a range of 5% to 40% by mole, and still more preferably in a range of 5% to 35% by mole with respect to the total amount of all constitutional units constituting the component (A1).

By setting the proportion of the constitutional unit (a3) to be greater than or equal to the lower limit of the above-described preferable range, the effects obtained by allowing the constitutional unit (a3) to be contained in the component (A1) can be sufficiently obtained. Further, by setting the proportion of the constitutional unit (a3) to be lower than or equal to the upper limit of the above-described preferable range, the constitutional unit (a3) and other constitutional units can be balanced.

<<Constitutional Unit (a4)>>

The constitutional unit (a4) is a constitutional unit containing an acid undissociable aliphatic cyclic group.

In a case where the component (A1) includes the constitutional unit (a4), the dry etching resistance of the resist pattern to be formed is improved. Further, the hydrophobicity of the component (A1) is improved. An increase in the hydrophobicity is considered to contribute to improvement of the resolution, the shape of the resist pattern, and the like particularly in a case of a solvent developing process.

The "acid undissociable aliphatic cyclic group" in the constitutional unit (a4) indicates a cyclic group which remains in the constitutional unit without being dissociated even at the time of an action of an acid in a case where an acid is generated in the resist composition upon exposure (for example, an acid is generated from the component (B) described below).

As the constitutional unit (a4), a constitutional unit which contains an acid undissociable aliphatic cyclic group and is also derived from an acrylic acid ester is preferable. As the cyclic group, any of the multitude of conventional polycyclic groups used in the resin component of resist compositions for ArF excimer lasers or KrF excimer lasers (preferably for ArF excimer lasers) can be used.

From the viewpoint of the industrial availability and the like, at least one polycyclic group selected from among a tricyclodecyl group, an adamantyl group, a tetracyclododecyl group, an isobornyl group, and a norbornyl group is particularly preferable. These polycyclic groups may include a linear or branched alkyl group having 1 to 5 carbon atoms as a substituent.

Specific examples of the constitutional unit (a4) include constitutional units represented by Formulae (a4-1) to (a4-7) shown below.

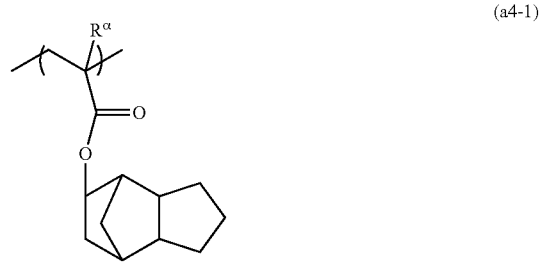

(a4-1)

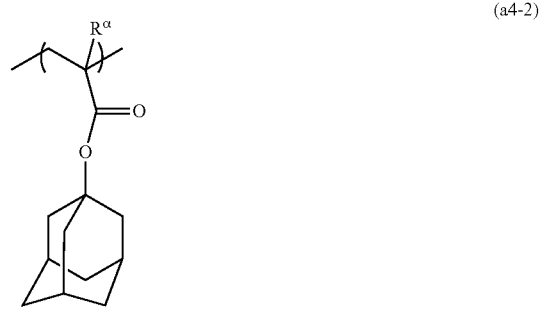

(a4-2)

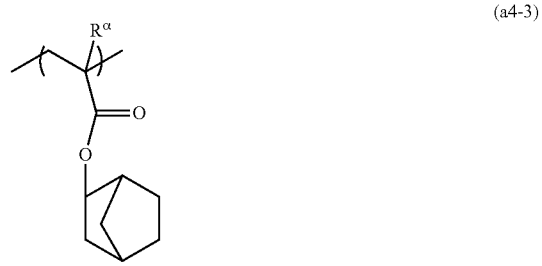

(a4-3)

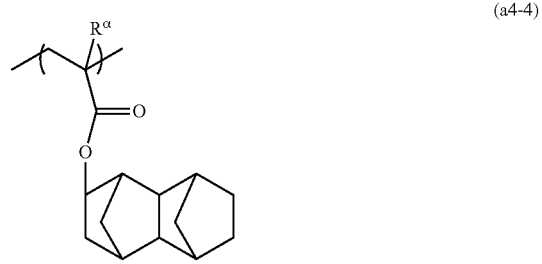

(a4-4)

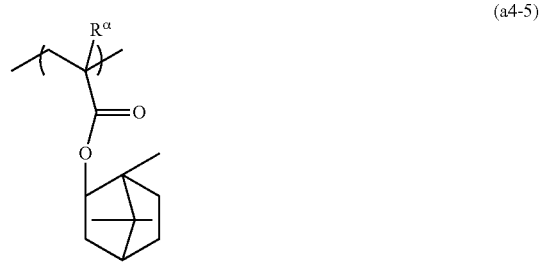

(a4-5)

-continued (a4-6)

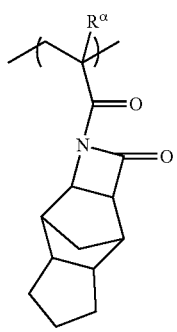

(a4-7)

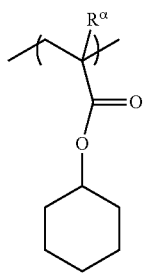

[In the formulae, $R^\alpha$ has the same definition as described above.]

The constitutional unit (a4) included in the component (A1) may be used alone or two or more kinds thereof may be used.

In a case where the component (A1) has the constitutional unit (a4), the proportion of the constitutional unit (a4) is preferably in a range of 1% to 30% by mole and more preferably in a range of 3% to 20% by mole with respect to the total amount (100% by mole) of all constitutional units constituting the component (A1).

By setting the proportion of the constitutional unit (a4) to be greater than or equal to the lower limit of the above-described preferable range, the effects obtained by allowing the constitutional unit (a4) to be contained in the component (A1) can be sufficiently obtained. Further, by setting the proportion of the constitutional unit (a4) to be lower than or equal to the upper limit of the above-described preferable range, the constitutional unit (a4) and other constitutional units can be balanced.

In the resist composition of the present embodiment, it is preferable that the component (A) contain a polymer compound (A1) having the constitutional unit (a1).

Specific preferred examples of the component (A1) include a polymer compound formed of repeating structures of the constitutional unit (a1) and the constitutional unit (a2), a polymer compound formed of repeating structures of the constitutional unit (a1) and the constitutional unit (a3), and a polymer compound formed of repeating structures of the constitutional unit (a1), the constitutional unit (a2), and the constitutional unit (a3).

The weight average molecular weight (Mw) (in terms of polystyrene determined by gel permeation chromatography (GPC)) of the component (A1) is not particularly limited, but is preferably in a range of 1,000 to 500,000 and more preferably in a range of 3,000 to 50,000. In a case where the Mw of the component (A1) is less than or equal to the upper limit of the above-described preferable range, the resist composition exhibits a satisfactory solubility in a solvent for a resist to be used as a resist. Meanwhile, in a case where the weight average molecular weight is greater than or equal to the lower limit of the above-described preferable range, dry etching resistance and the cross-sectional shape of the resist pattern become excellent.

The dispersity (Mw/Mn) of the component (A1) is not particularly limited, but is preferably in a range of 1.0 to 4.0, more preferably in a range of 1.0 to 3.0, and particularly preferably in a range of 1.0 to 2.5. Further, Mn indicates the number average molecular weight.

The component (A1) may be used alone or in a combination of two or more kinds thereof.

The proportion of the component (A1) in the component (A) is preferably 25% by mass or greater, more preferably 50% by mass or greater, still more preferably 75% by mass or greater, or may be 100% by mass with respect to the total mass of the component (A). In a case where the proportion thereof is 25% by mass or greater, a resist pattern with excellent lithography characteristics of enhanced sensitivity, dimension uniformity, and the like is easily formed.

Method of Producing Component (A1):

The component (A1) can be produced by dissolving a monomer, from which each constitutional unit is derived, in a polymerization solvent and adding a radical polymerization initiator such as azobisisobutylonitrile (AIBN) or dimethyl 2,2'-azobisisobutyrate (for example, V-601) to the solution so that the polymerization is carried out. Further, a —C(CF$_3$)$_2$—OH group may be introduced into the terminal of the component (A1) during the polymerization using a chain transfer agent such as HS—CH$_2$—CH$_2$—CH$_2$—C(CF$_3$)$_2$—OH together. As described above, a copolymer into which a hydroxyalkyl group, formed by substitution of some hydrogen atoms in the alkyl group with fluorine atoms, has been introduced is effective for reducing development defects and reducing line edge roughness (LER: uneven irregularities of a line side wall).

In the resist composition of the present embodiment, the component (A) may be used alone or in a combination of two or more kinds thereof.

In the resist composition of the present embodiment, the content of the component (A) may be adjusted according to the film thickness of a resist intended to be formed.

<Acid Generator Component; Component (B)>

In the present embodiment, the acid generator component (B) contains an acid generator (B1) (hereinafter, also referred to as a "component (B1)") formed of a compound represented by Formula (b1).

(b1)

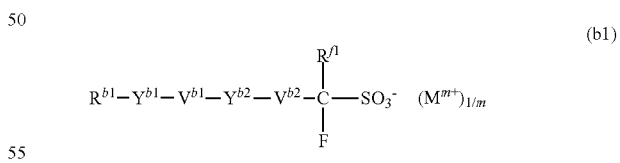

[In the formula, $R^{b1}$ represents a monovalent hydrocarbon group which has a steroid skeleton and 17 to 50 carbon atoms, where the hydrocarbon group may have a hetero atom. $Y^{b1}$ and $Y^{b2}$ each independently represent a divalent linking group having a hetero atom. $V^{b1}$ represents a divalent linking group containing a cyclic aliphatic hydrocarbon group. $V^{b2}$ represents an alkylene group, a fluorinated alkylene group, or a single bond. $R^{f1}$ represents a hydrogen atom, a fluorine atom, or a fluorinated alkyl group having 1 to 5 carbon atoms. m represents an integer of 1 or greater, and $M^{m+}$ represents an m-valent organic cation.]

[Anion Moiety ($R^{b1}$—$Y^{b1}$—$V^{b1}$—$Y^{b2}$—$V^{b2}$—$CFR^{f1}$—$SO_3$—)]

In Formula (b1), $R^{b1}$ represents a monovalent hydrocarbon group which has a steroid skeleton and 17 to 50 carbon atoms. Here, the hydrocarbon group may have a hetero atom.

Here, "steroid skeleton" indicates a skeleton having a ring structure represented by Chemical Formula (St), in which three 6-membered rings and one 5-membered ring are fused.

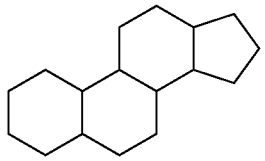

(St)

Examples of the hetero atom contained in the monovalent hydrocarbon group of $R^{b1}$ include an oxygen atom, a nitrogen atom, and a sulfur atom. Among these, an oxygen atom is preferable.

The steroid skeleton contained in the monovalent hydrocarbon group of $R^{b1}$ may have a hetero atom. For example, an alkyl group (preferably an alkyl group having 1 to 5 carbon atoms and particularly preferably a methyl group), a hydroxy group, a carboxy group, an oxo group (=O), an alkoxy group, an alkylcarbonyloxy group (preferably an acetoxy group), a formyloxy group (HC(=O)—O—), or a lactone-containing cyclic group may be bonded to the ring structure represented by Chemical Formula (St). The lactone-containing cyclic group may contain one or more double bonds in the ring structure. The number of double bonds is not particularly limited, and is preferably 1.

The number of carbon atoms of $R^{b1}$ is in a range of 17 to 50, preferably in a range of 17 to 40, more preferably in a range of 17 to 30, and particularly preferably in a range of 17 to 20.

Here, the number of carbon atoms of $R^{b1}$ includes the number of carbon atoms constituting the steroid skeleton and the number of carbon atoms in the substituent bonded to the steroid skeleton.

In Formula (b1), $R^{f1}$ represents a hydrogen atom, a fluorine atom, or a fluorinated alkyl group having 1 to 5 carbon atoms.

The fluorinated alkyl group having 1 to 5 carbon atoms of $R^{f1}$ may be linear or branched. Examples of the fluorinated alkylene group of $R^{f1}$ include a group in which some or all hydrogen atoms in the alkylene group have been substituted with fluorine atoms. Among these, as the fluorinated alkyl group, a perfluoroalkyl group in which all hydrogen atoms in the alkylene group have been substituted with fluorine atoms is preferable, and a perfluoroalkyl group having 1 to 3 carbon atoms is more preferable.

Among the examples, $R^{f1}$ preferably represents a fluorine atom or a perfluoroalkyl group having 1 to 3 carbon atoms, more preferably a fluorine atom or a perfluoroalkyl group having 1 or 2 carbon atoms, still more preferably a fluorine atom or a trifluoromethylene group, and particularly preferably a fluorine atom.

In Formula (b1), $Y^{b1}$ represents a divalent linking group having a hetero atom.

Examples of the divalent linking group having a hetero atom of $Y^{b1}$ are the same as those exemplified as the divalent linking group having a hetero atom represented by $Ya^1$ in Formula (a2-1).

As the hetero atom in the divalent linking group having a hetero atom, the divalent linking group preferably has an oxygen atom and may have a hetero atom other than an oxygen atom. Examples of the hetero atom other than an oxygen atom include a nitrogen atom and a sulfur atom. It is preferable that the divalent linking group having a hetero atom of $Y^{b1}$ be a divalent linking group containing at least one functional group selected from the group consisting of a carboxylic acid ester group, an ether group, a carbonic acid ester group, a carbonyl group, and an amide group.

Examples of the divalent linking group containing a functional group include a carboxylic acid ester group [—C(=O)—O— or —O—C(=O)—], an ether group (—O—), a carbonic acid ester group [—O—C(=O)—O—], a carbonyl group [—C(=O)—], an amide group [—NH—C(=O)— or —C(=O)—NH—], and a combination of an alkylene group and at least one functional group of these. A sulfonyl group (—$SO_2$—) may be further linked to the combination.

In the combination of such a functional group and an alkylene group, an alkylene group having 1 to 30 carbon atoms is preferable, an alkylene group having 1 to 10 carbon atoms is more preferable, and an alkylene group having 1 to 5 carbon atoms is still more preferable as the alkylene group. Further, the alkylene group here may be a linear or branched alkylene group.

Specific examples of the alkylene group include a methylene group [—$CH_2$—]; an alkylmethylene group such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, or —C($CH_2CH_3$)$_2$—; an ethylene group [—$CH_2CH_2$—]; an alkylethylene group such as —CH($CH_3$)$CH_2$—, —CH($CH_3$)CH($CH_3$)—, —C($CH_3$)$_2CH_2$—, or —CH($CH_2CH_3$)$CH_2$—; a trimethylene group (n-propylene group) [—$CH_2CH_2CH_2$—]; an alkyltrimethylene group such as —CH($CH_3$)$CH_2CH_2$— or —$CH_2$CH($CH_3$)$CH_2$—; a tetramethylene group [—$CH_2CH_2CH_2CH_2$—]; an alkyltetramethylene group such as —CH($CH_3$)$CH_2CH_2CH_2$—, —$CH_2$CH($CH_3$)$CH_2CH_2$—; and a pentamethylene group [—$CH_2CH_2CH_2CH_2CH_2$—].

$Y^{b1}$ preferably represents a divalent linking group containing a carboxylic acid ester group or a divalent linking group containing an ether bond, more preferably a divalent linking group containing a carboxylic acid ester group, and still more preferably a combination of a carboxylic acid ester group and an alkylene group.

Preferred examples of $R^{b1}$—$Y^{b1}$ include linking groups represented by $R^{b1}$—$Y^{b101}$—C(=O)—O— or $R^{b1}$—$Y^{b101}$—O—C(=O)— ($Y^{b101}$ represents an alkylene group having 1 to 5 carbon atoms). Among these, a group represented by $R^{b1}$—$Y^{b101}$—C(=O)—O— is particularly preferable. Examples of the alkylene group of Yb101 are the same as those exemplified in the specific examples above.

In Formula (b1), $V^{b1}$ represents a divalent linking group containing a cyclic aliphatic hydrocarbon group.

Examples of the divalent hydrocarbon group containing a cyclic aliphatic hydrocarbon group include an alicyclic hydrocarbon group (a group in which two hydrogen atoms have been removed from an aliphatic hydrocarbon ring), a group in which the alicyclic hydrocarbon group is bonded to the terminal of the above-described chain-like aliphatic hydrocarbon group, and a group in which the alicyclic group is interposed in the above-described linear or branched aliphatic hydrocarbon group. The linear or branched aliphatic hydrocarbon group is the same as defined for the above-described linear aliphatic hydrocarbon group or the above-described branched aliphatic hydrocarbon group.

The cyclic hydrocarbon group preferably has 3 to 20 carbon atoms and more preferably 3 to 12 carbon atoms.

The alicyclic hydrocarbon group may be a monocyclic group or a polycyclic group. As the monocyclic alicyclic hydrocarbon group, a group in which two hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which two hydrogen atoms have been removed from a polycycloalkane is preferable. As the polycycloalkane, a group having 7 to 12 carbon atoms is preferable. Specific examples of the polycycloalkane include adamantane, norbornane, isobornane, tricyclodecane, tetracyclododecane, and bicyclooctane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group serving as the substituent is preferably an alkyl group having 1 to 5 carbon atoms, and a methyl group, an ethyl group, a propyl group, an n-butyl group, or a tert-butyl group is particularly preferable.

The alkoxy group serving as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom serving as the substituent include a fluorine atom, a chlorine atom, a bromine atom, and an iodine atom, and a fluorine atom is preferable.

Examples of the halogenated alkyl group serving as the substituent include groups in which some or all hydrogen atoms in the above-described alkyl groups have been substituted with the above-described halogen atoms.

In the cyclic aliphatic hydrocarbon group, some carbon atoms constituting the ring structure thereof may be substituted with a substituent containing a hetero atom. As the substituent containing a hetero atom, —O—, —C(=O)—O—, —S—, —S(=O)$_2$—, or —S(=O)$_2$—O— is preferable. Examples of the cyclic aliphatic hydrocarbon group having a hetero atom in the ring structure include the lactone-containing cyclic groups and —SO$_2$-containing cyclic groups described above. Among these, a lactone-containing cyclic group is preferable as the cyclic aliphatic hydrocarbon group having a hetero atom in the ring structure. Examples of the lactone-containing cyclic group include groups formed by removing one hydrogen atom from a group represented by any of Formulae (a2-r-1) to (a2-r-7). As the lactone-containing cyclic group, a group formed by removing one hydrogen atom from a group represented by any of Formulae (a2-r-1), (a2-r-2), and (a2-r-6) is preferable, and a group formed by removing one hydrogen atom from a group represented by any of Chemical Formulae (r-lc-1-1) to (r-lc-1-7), (r-lc-2-1) to (r-lc-2-7), and (r-lc-6-1) is more preferable.

Among the examples, as the cyclic aliphatic hydrocarbon group represented by $V^{b1}$, a polycyclic group is preferable and an unsubstituted polycyclic group is more preferable. Particularly preferred examples thereof include a group formed by removing two hydrogen atoms from adamantane, a group formed by removing two hydrogen atoms from norbornane, and a group formed by removing two hydrogen atoms from bicyclooctane. Among these, a group formed by removing two hydrogen atoms from adamantane (such as a 1,5-adamantylene group or a 2,6-adamantylene group) is most preferable.

In Formula (b1), $Y^{b2}$ represents a divalent linking group having a hetero atom.

Examples of the divalent linking group having a hetero atom of $Y^{b2}$ are the same as those exemplified as $Y^{b1}$. Preferred examples of $V^{b1}$—$Y^{b1}$ include linking groups represented by any of $V^{b1}$—C(=O)—O—$Y^{b21}$— and $V^{b1}$—O—C(=O)—$Y^{b201}$— ($Y^{b201}$ represents an alkylene group having 1 to 5 carbon atoms). Among these, a group represented by $V^{b1}$—C(=O)—O—$Y^{b201}$— is particularly preferable. Examples of the alkylene group of $Y^{b201}$ are the same as the specific examples of the alkylene group described in the section of $Y^{b1}$. Among the examples, an ethylene group or a methylene group is particularly preferable.

In Formula (b1), $V^{b2}$ represents an alkylene group, a fluorinated alkylene group, or a single bond.

The alkylene group or fluorinated alkylene group of $V^{b2}$ may be linear or branched, but is preferably linear. The number of carbon atoms of the alkylene group or fluorinated alkylene group of $V^{b2}$ is preferably in a range of 1 to 4 and more preferably in a range of 1 to 3.

Examples of the fluorinated alkylene group of $V^{b2}$ include groups in which some or all hydrogen atoms in an alkylene group have been substituted with fluorine atoms. It is preferable that the fluorinated alkylene group of $V^{b2}$ be formed such that a carbon atom adjacent to the carbon atom to which $R^{f1}$ is bonded contains a fluorinated alkylene group having at least one fluorine atom or 1 to 3 carbon atoms.

Particularly preferred examples of $V^{b2}$ include an alkylene group having 1 to 3 carbon atoms and a fluorinated alkylene group having 1 to 3 carbon atoms. In the fluorinated alkylene group having 1 to 3 carbon atoms, it is preferable that $Y^{b2}$—$V^{b2}$ be represented by $Y^{b2}$—(CH$_2$)$_n$—CHF— or $Y^{b2}$—(CH$_2$)$_n$—CF$_2$— (n represents an integer of 0 to 2).

Preferred examples of the anion moiety in the component (B1) include an anion moiety represented by Formula (b1-an1).

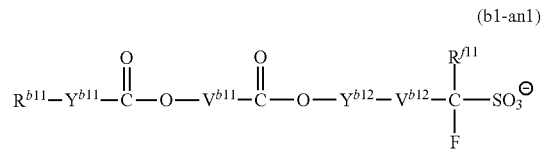

(b1-an1)

[In the formula, $R^{b11}$ represents a monovalent hydrocarbon group which has a steroid skeleton and 17 to 50 carbon atoms. Here, the hydrocarbon group may have a hetero atom. $Y^{b11}$ and $Y^{b12}$ each independently represent an alkylene group or a single bond. $V^{b11}$ represents a divalent linking group containing a cyclic aliphatic hydrocarbon group. $V^{b12}$ represents a fluorinated alkylene group or a single bond. $R^{f11}$ represents a hydrogen atom, a fluorine atom, or a fluorinated alkyl group having 1 to 5 carbon atoms.]

In Formula (b1-an1), $R^{b11}$ represents a monovalent hydrocarbon group having a steroid skeleton and 17 to 50 carbon atoms. $R^{b11}$ has the same definition as that for $R^{b1}$ in Formula (b1).

In Formula (b1-an1), $Y^{b11}$ represents an alkylene group or a single bond. The alkylene group of $Y^{b11}$ may be linear or branched. As the alkylene group represented by $Y^{b11}$ an alkylene group having 1 to 10 carbon atoms is preferable, and an alkylene group having 1 to 5 carbon atoms is more preferable. Specific examples of such an alkylene group are those exemplified as the alkylene group represented by $Y^{b1}$ in Formula (b1).

$Y^{b11}$ preferably represents an alkylene group and more preferably an alkylene group having 1 to 5 carbon atoms.

In Formula (b1-an1), $V^{b11}$ represents a divalent linking group containing a cyclic aliphatic hydrocarbon group. $V^{b11}$ has the same definition as that for $V^{b1}$ in Formula (b1).

In Formula (b1-an1), $Y^{b12}$ represents an alkylene group or a single bond.

The alkylene group of $Y^{b12}$ may be linear or branched. As the alkylene group represented by $Y^{b12}$, an alkylene group having 1 to 10 carbon atoms is preferable, an alkylene group having 1 to 5 carbon atoms is more preferable, and an alkylene group having 1 to 3 carbon atoms is still more preferable. Specific examples of such an alkylene group are those exemplified as the alkylene group represented by $Y^{b1}$ in Formula (b1).

$Y^{b12}$ preferably represents an alkylene group, more preferably an alkylene group having 1 to 5 carbon atoms, and particularly preferably an ethylene group or a methylene group.

In Formula (b1-an1), $V^{b12}$ represents a fluorinated alkyl group or a single bond. The fluorinated alkylene group of $V^{b12}$ may be linear or branched. The number of carbon atoms of the fluorinated alkylene group is preferably in a range of 1 to 4, more preferably in a range of 1 to 3, still more preferably 1 or 2, and particularly preferably 1.

Among these, $V^{b12}$ preferably represents a single bond, —CHF—, or —CF$_2$— and more preferably —CHF— or —CF$_2$—.

In Formula (b1-an1), $R^{f11}$ represents a hydrogen atom, a fluorine atom, or a fluorinated alkyl group having 1 to 5 carbon atoms. $R^{f11}$ has the same definition as that for $R^{f1}$ in Formula (b1).

Specific examples of the anion moiety represented by Formula (b1-an1) include those exemplified as the anion moiety represented by Formula (b1-an2) or (b1-an3).

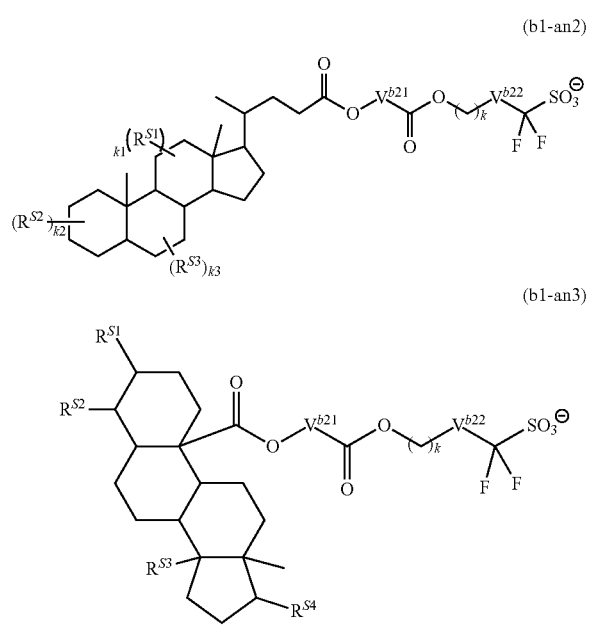

[In the formulae, $R^{S1}$, $R^{S2}$, and $R^{S3}$ each independently represent a substituent having a hetero atom. $R^{S4}$ represents a lactone-containing cyclic group. $V^{b21}$ represents a cyclic aliphatic hydrocarbon group. $V^{b22}$ represents a single bond, —CHF—, or —CF$_2$—. k1, k2, and k3 each independently represent 0 or 1. k represents an integer of 0 to 5.]

In Formulae (b1-an2) and (b1-an3), $R^{S1}$, $R^{S2}$, and $R^{S3}$ each independently represent a substituent having a hetero atom. Examples of the substituent having a hetero atom of $R^{S1}$ to $R^{S3}$ include a hydroxy group, a carboxy group, an oxo group (=O), an alkoxy group, an alkylcarbonyloxy group, and a formyloxy group (HC(=O)—O—). Among these, a hydroxy group, an oxo group, an alkylcarbonyloxy group (preferably an acetoxy group), or a formyloxy group is preferable, and an oxo group or a hydroxy group is particularly preferable.

In Formulae (b1-an2) and (b1-an3), k1 to k3 each independently represent 0 or 1 and preferably 1.

In Formulae (b1-an2) and (b1-an3), $V^{b21}$ represents a cyclic aliphatic hydrocarbon group. Examples of the cyclic aliphatic hydrocarbon group of $V^{b21}$ are those exemplified as the cyclic aliphatic hydrocarbon group of $V^{b1}$ in Formula (b1).

In a case where $V^{b21}$ represents a monocyclic group, examples of the monocyclic group include groups formed by removing two hydrogen atoms from a monocycloalkane. As the monocycloalkane, cyclopentane or cyclohexane is preferable, and a cyclohexane is more preferable.

In a case where $V^{b21}$ represents a polycyclic group, examples of the polycyclic group include groups formed by removing two hydrogen atoms from a polycycloalkane. Examples of the polycycloalkane include adamantane, norbornane, isobornane, tricyclodecane, and tetracyclododecane. Among these, adamantane or norbornane is preferable, and adamantane is more preferable.

Among the examples, $V^{b21}$ preferably represents a polycyclic group and particularly preferably a group formed by removing two hydrogen atoms from adamantane (such as a 1,5-adamantylene group or a 2,6-adamantylene group).

In Formulae (b1-an2) and (b1-an3), k represents an integer of 0 to 5. k preferably represents an integer of 1 to 3, more preferably 1 or 2, and still more preferably 2.

In Formulae (b1-an2) and (b1-an3), $V^{b22}$ represents a single bond, —CHF—, or —CF$_2$—. $V^{b22}$ preferably represents —CHF— or —CF$_2$— and more preferably —CHF—.

In Formula (b1-an3), $R^{S4}$ represents a lactone-containing cyclic group. The lactone-containing cyclic group may be a group having one or more double bonds in the ring structure. Examples of the lactone-containing cyclic group include those having one or more double bonds in the ring structure represented by Formula (a2-r-1). The number of double bonds is preferably 1.

Specific examples of the anion moiety in the compound (B1) are shown below. In the formula, $R^{S1}$, $R^{S2}$, and $R^{S3}$ each independently represent a substituent having a hetero atom, and k1, k2, and k3 each independently represent 0 or 1. Further, the anion moiety in the component (B1) is not limited to these specific examples.

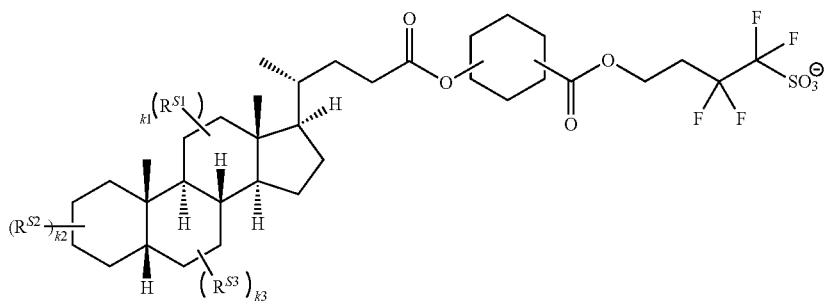
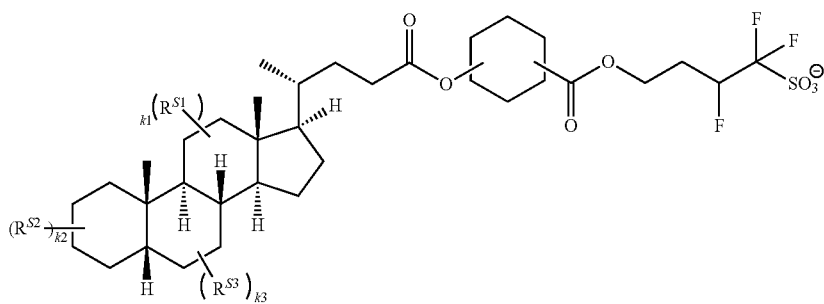
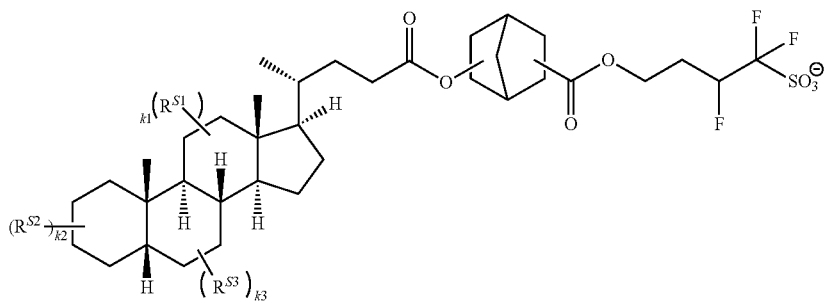
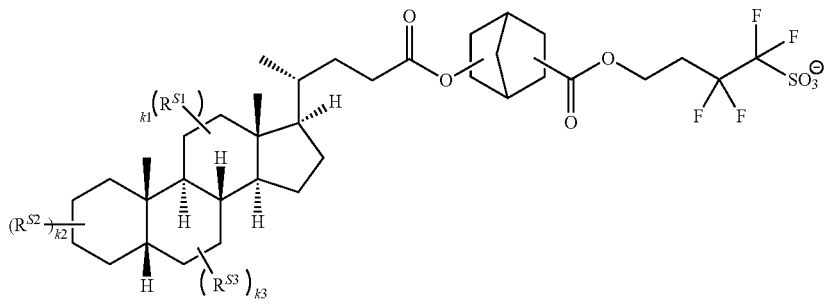
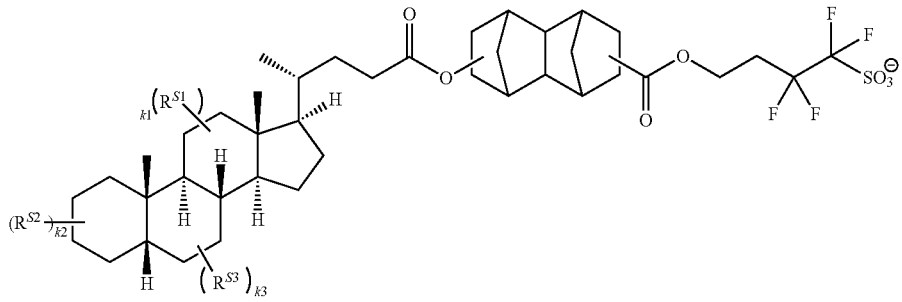

-continued
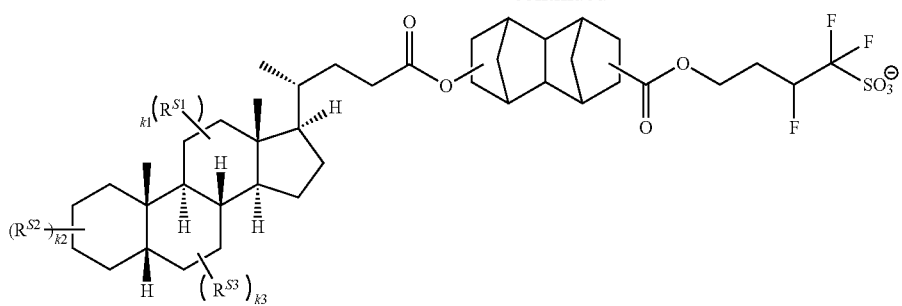
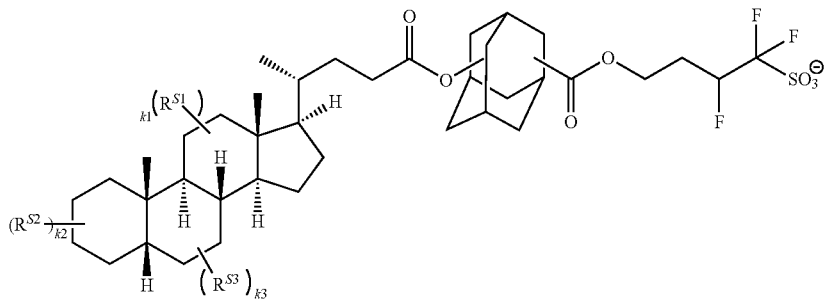
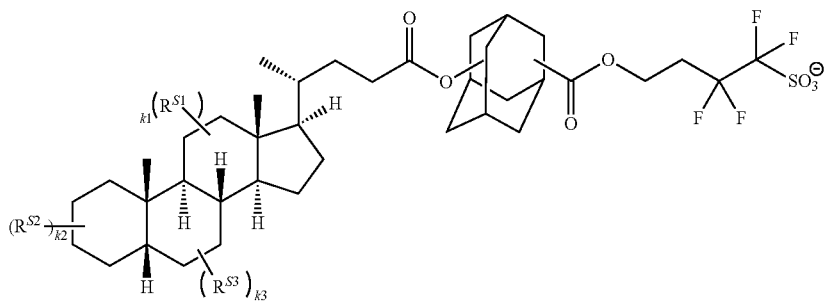
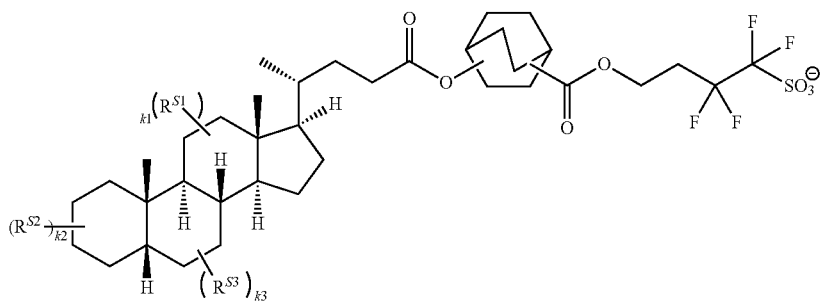
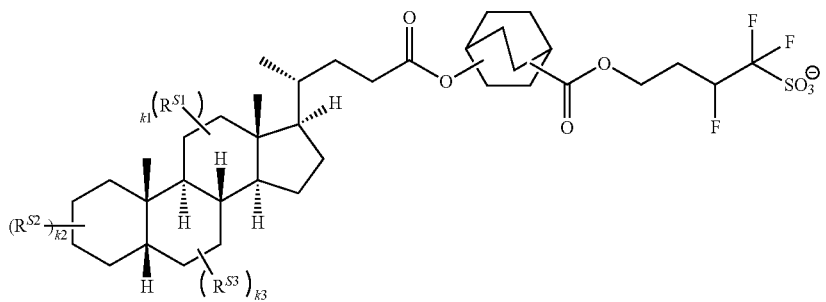

-continued
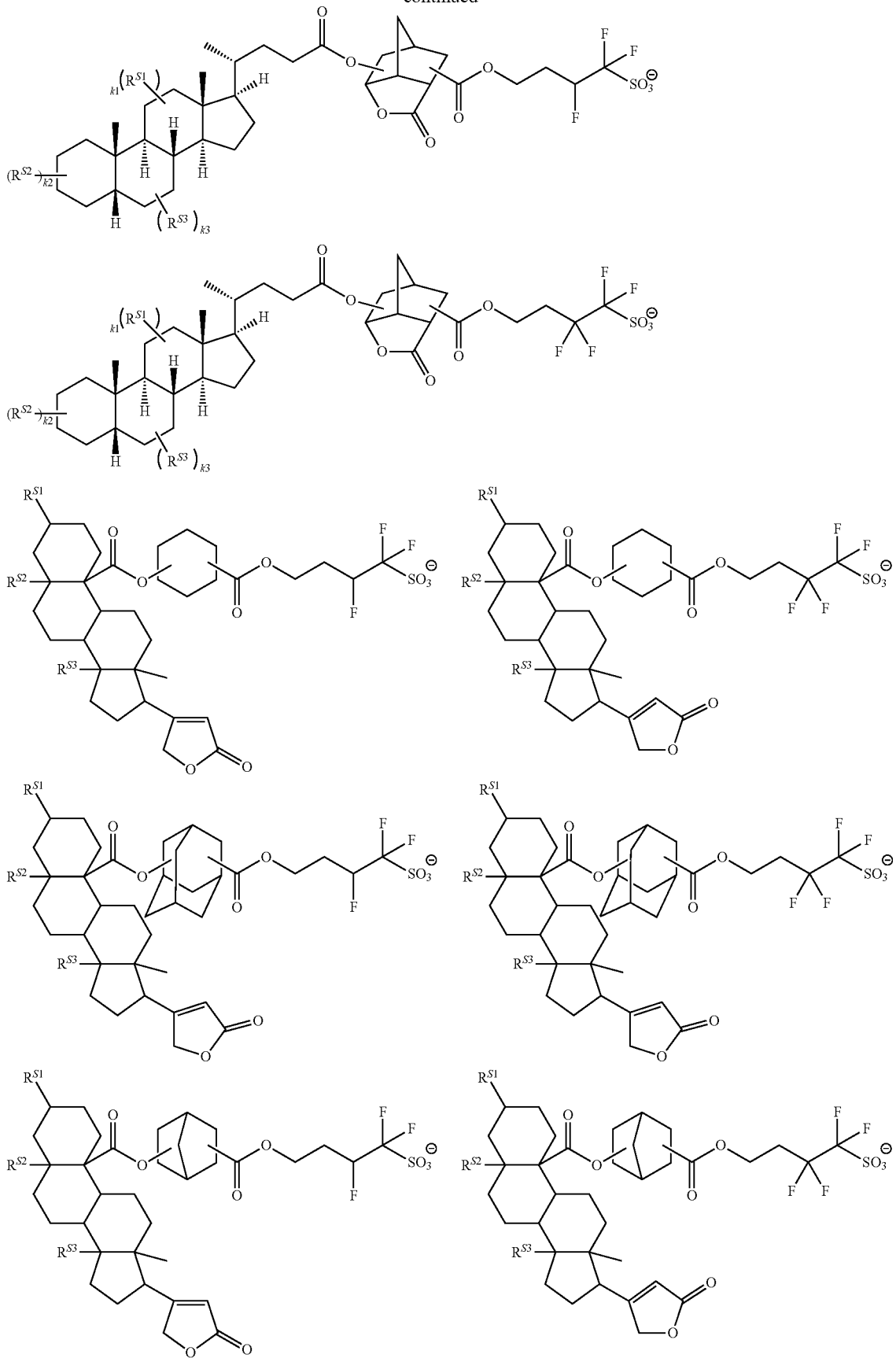

-continued

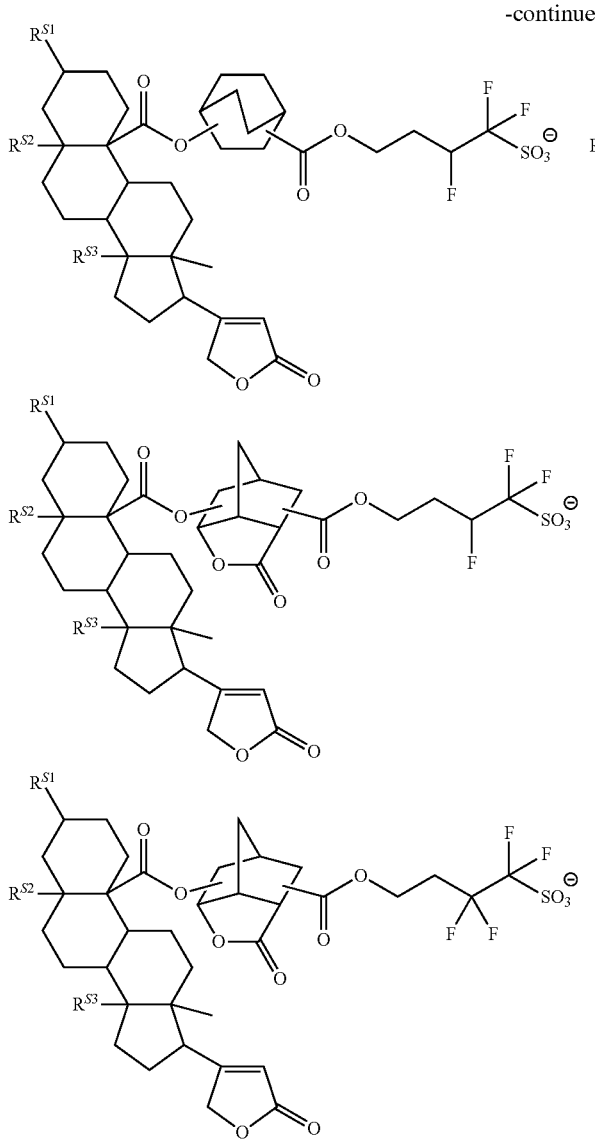

[Cation moiety: $(M^{m+})_{1/m}$]

In Formula (b1), $M^{m+}$ represents an m-valent organic cation.

As the organic cation represented by $M^{m+}$, an onium cation is preferable, and a sulfonium cation or an iodonium cation is more preferable. m represents an integer of 1 or greater.

Preferred examples of the cation moiety $((M^{m+})_{1/m})$ include organic cations represented by Formulae (ca-1) to (ca-5).

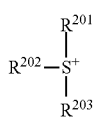

(ca-1)

(ca-2)

-continued

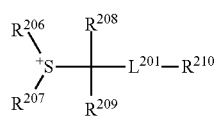

(ca-3)

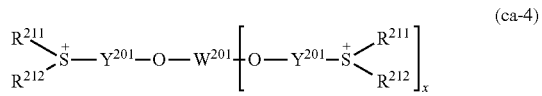

(ca-4)

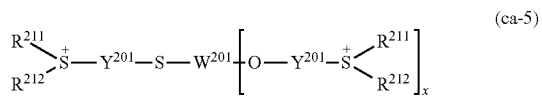

(ca-5)

[In the formulae, $R^{201}$ to $R^{207}$, $R^{211}$, and $R^{212}$ each independently represent an aryl group, an alkyl group, or an alkenyl group which may have a substituent, provided that $R^{201}$ to $R^{203}$, $R^{206}$ and $R^{207}$, and $R^{211}$ and $R^{212}$ may be mutually bonded to form a ring with the sulfur atom in the formula; $R^{208}$ and $R^{209}$ each independently represent a hydrogen atom or an alkyl group having 1 to 5 carbon atoms;

$R^{210}$ represents an aryl group which may have a substituent, an alkyl group which may have a substituent, an alkenyl group which may have a substituent, or a —$SO_2$-containing cyclic group which may have a substituent; $L^{201}$ represents —C(=O)— or —C(=O)—O—; $Y^{201}$ each independently represent an arylene group, an alkylene group, or an alkenylene group; x represents 1 or 2; and $W^{201}$ represents an (x+1)-valent linking group.]

Examples of the aryl group of $R^{201}$ to $R^{207}$, $R^{211}$, and $R^{212}$ include an unsubstituted aryl group having 6 to 20 carbon atoms, and a phenyl group or a naphthyl group is preferable.

The alkyl group of $R^{201}$ to $R^{207}$, $R^{211}$, and $R^{212}$ is a chain-like or cyclic alkyl group, and the number of carbon atoms thereof is preferably in a range of 1 to 30.

The alkenyl group of $R^{201}$ to $R^{207}$, $R^{211}$, and $R^{212}$ preferably has 2 to 10 carbon atoms.

Examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, and groups represented by Formulae (ca-r-1) to (ca-r-7) shown below.

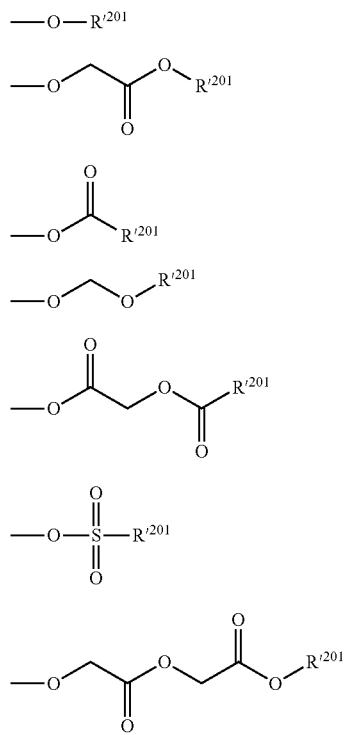

[In the formulae, each $R'^{201}$ independently represents a hydrogen atom, a cyclic group which may have a substituent, a chain-like alkyl group which may have a substituent, or a chain-like alkenyl group which may have a substituent.]

In Formulae (ca-r-1) to (ca-r-7), $R'^{201}$ represents a hydrogen atom, a cyclic group which may have a substituent, a chain-like alkyl group which may have a substituent, or a chain-like alkenyl group which may have a substituent.

Cyclic Group which May have Substituent:

The cyclic group is preferably a cyclic hydrocarbon group, and the cyclic hydrocarbon group may be an aromatic hydrocarbon group or an aliphatic hydrocarbon group. The aliphatic hydrocarbon group indicates a hydrocarbon group that has no aromaticity. The aliphatic hydrocarbon group may be saturated or unsaturated, but in general, the aliphatic hydrocarbon group is preferably saturated.

The aromatic hydrocarbon group of $R'^{201}$ is a hydrocarbon group having an aromatic ring. The aromatic hydrocarbon ring preferably has 3 to 30 carbon atoms, more preferably 5 to 30, still more preferably 5 to 20, particularly preferably 6 to 15, and most preferably 6 to 10. Here, the number of carbon atoms in a substituent is not included in the number of carbon atoms.

Specific examples of the aromatic ring contained in the aromatic hydrocarbon group of $R'^{201}$ include benzene, fluorene, naphthalene, anthracene, phenanthrene, biphenyl, or an aromatic hetero ring in which some carbon atoms constituting any of these aromatic rings have been substituted with hetero atoms. Examples of the hetero atom in the aromatic hetero rings include an oxygen atom, a sulfur atom, and a nitrogen atom.

Specific examples of the aromatic hydrocarbon group of $R'^{201}$ include a group in which one hydrogen atom has been removed from the above-described aromatic ring (an aryl group such as a phenyl group or a naphthyl group), and a group in which one hydrogen atom in the aromatic ring has been substituted with an alkylene group (an arylalkyl group such as a benzyl group, a phenethyl group, a 1-naphthylmethyl group, a 2-naphthylmethyl group, 1-naphthylethyl group, or a 2-naphthylethyl group). The alkylene group (an alkyl chain in the arylalkyl group) preferably has 1 to 4 carbon atom, more preferably 1 or 2 carbon atoms, and particularly preferably 1 carbon atom.

Examples of the cyclic aliphatic hydrocarbon group of $R'^{201}$ include aliphatic hydrocarbon groups containing a ring in the structure thereof.

Examples of the hydrocarbon group containing a ring in the structure thereof include an alicyclic hydrocarbon group (a group in which one hydrogen atom has been removed from an aliphatic hydrocarbon ring), a group in which the alicyclic hydrocarbon group is bonded to the terminal of a linear or branched aliphatic hydrocarbon group, and a group in which the alicyclic hydrocarbon group is interposed in a linear or branched aliphatic hydrocarbon group.

The alicyclic hydrocarbon group preferably has 3 to 20 carbon atoms and more preferably 3 to 12 carbon atoms.

The alicyclic hydrocarbon group may be a polycyclic group or a monocyclic group. As the monocyclic alicyclic hydrocarbon group, a group in which one or more hydrogen atoms have been removed from a monocycloalkane is preferable. The monocycloalkane preferably has 3 to 6 carbon atoms, and specific examples thereof include cyclopentane and cyclohexane. As the polycyclic alicyclic hydrocarbon group, a group in which one or more hydrogen atoms have been removed from a polycycloalkane is preferable, and the number of carbon atoms of the polycycloalkane is preferably in a range of 7 to 30. Among polycycloalkanes, a polycycloalkane having a bridged ring polycyclic skeleton, such as adamantane, norbornane, isobornane, tricyclodecane, or tetracyclododecane, and a polycycloalkane having a fused ring polycyclic skeleton, such as a cyclic group having a steroid skeleton are preferable.

Among these examples, as the cyclic aliphatic hydrocarbon group of $R'^{201}$, a group in which one or more hydrogen atoms have been removed from a monocycloalkane or a polycycloalkane is preferable, a group in which one hydrogen atom has been removed from a polycycloalkane is more preferable, an adamantyl group or a norbornyl group is particularly preferable, and an adamantyl group is most preferable.

The linear or branched aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and particularly preferably 1 to 3 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$-] and a pentamethylene group [—$(CH_2)_5$—].

As the branched aliphatic hydrocarbon group, branched alkylene groups are preferable, and specific examples thereof include various alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$— and —$CH_2CH(CH_3)CH_2$—; and alkyltetramethylene groups such as —$CH(CH_3)CH_2CH_2CH_2$— and —$CH_2CH(CH_3)CH_2CH_2$—. As the alkyl group in the alkylalkylene group, a linear alkyl group having 1 to 5 carbon atoms is preferable.

The cyclic hydrocarbon group of $R'^{201}$ may contain a hetero atom such as a hetero ring. Specific examples thereof include lactone-containing cyclic groups represented by Formulae (a2-r-1) to (a2-r-7), the —$SO_2$-containing cyclic group represented by Formulae (a5-r-1) to (a5-r-4), and other heterocyclic groups represented by Chemical Formulae (r-hr-1) to (r-hr-16).

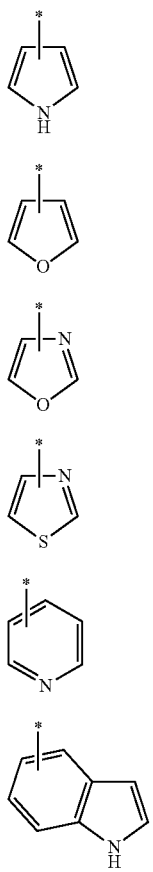
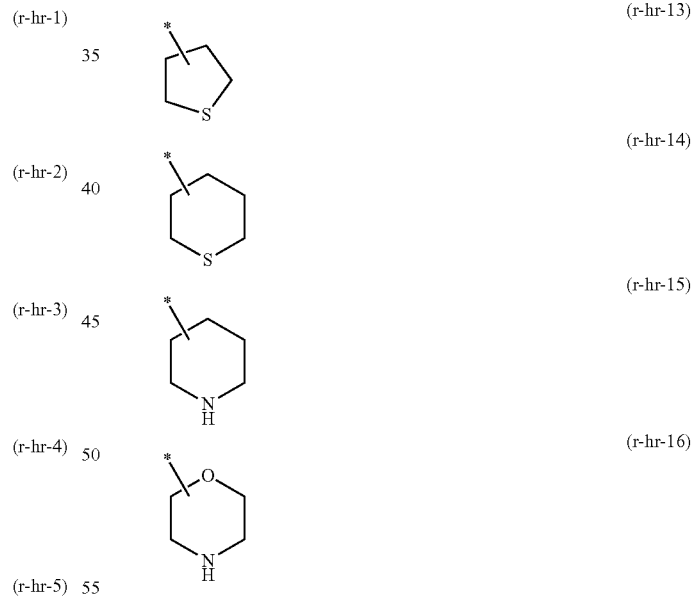

Examples of the substituent for the cyclic group of $R'^{201}$ include an alkyl group, an alkoxy group, a halogen atom, a halogenated alkyl group, a hydroxyl group, a carbonyl group, and a nitro group.

The alkyl group serving as the substituent is preferably an alkyl group having 1 to 5 carbon atoms, and a methyl group, an ethyl group, a propyl group, an n-butyl group, or a tert-butyl group is most preferable.

The alkoxy group serving as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for the substituent include a fluorine atom, a chlorine atom, a bromine atom, and an iodine atom, and a fluorine atom is preferable.

Examples of the above-described halogenated alkyl group serving as the substituent includes a group in which some or all hydrogen atoms in an alkyl group having 1 to 5 carbon atoms such as a methyl group, an ethyl group, a propyl group, an n-butyl group, or a tert-butyl group have been substituted with the above-described halogen atoms.

The carbonyl group serving as the substituent is a group that substitutes a methylene group ($—CH_2—$) constituting the cyclic hydrocarbon group.

Chain-like alkyl group which may have substituent:

The chain-like alkyl group of $R'^{201}$ may be linear or branched.

The linear alkyl group preferably has 1 to 20 carbon atoms, more preferably 1 to 15 carbon atoms, and most preferably 1 to 10 carbon atoms. Specific examples thereof include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group, and a docosyl group.

The branched alkyl group preferably has 3 to 20 carbon atoms, more preferably 3 to 15, and most preferably 3 to 10. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain-Like Alkenyl Group which May have Substituent:

Such a chain-like alkenyl group of $R'^{201}$ may be linear or branched, and the number of carbon atoms thereof is preferably in a range of 2 to 10, more preferably in a range of 2 to 5, still more preferably in a range of 2 to 4, and particularly preferably 3. Examples of the linear alkenyl group include a vinyl group, a propenyl group (an allyl group), and a butynyl group. Examples of the branched alkenyl group include a 1-methylvinyl group, a 2-methylvinyl group, a 1-methylpropenyl group, and a 2-methylpropenyl group.

Among the examples, as the chain-like alkenyl group, a linear alkenyl group is preferable, a vinyl group or a propenyl group is more preferable, and a vinyl group is particularly preferable.

As the substituent for the chain-like alkyl group or alkenyl group of $R'^{201}$, an alkoxy group, a halogen atom, a halogenated alkyl group, a hydroxyl group, a carbonyl group, a nitro group, an amino group, a cyclic group of $R'^{201}$ or the like can be used.

Examples of the cyclic group which may have a substituent, the chain-like alkyl group which may have a substituent, and the chain-like alkenyl group which may have a substituent of $R'^{201}$ are the same as those exemplified as the acid dissociable group represented by Formula (a1-r-2) as a cyclic group which may have a substituent or a chain-like alkyl group which may have a substituent, in addition to the above-described groups.

Among the examples, as $R'^{201}$, a cyclic group which may have a substituent is preferable, and a cyclic hydrocarbon group which may have a substituent is more preferable. More specific preferred examples thereof include a phenyl group, a naphthyl group, a group in which one or more hydrogen atoms have been removed from a polycycloalkane, a lactone-containing cyclic group represented by any of Formulae (a2-r-1) to (a2-r-7), and a $—SO_2$-containing cyclic group represented by any of Formulae (a5-r-1) to (a5-r-4).

In a case where $R^{201}$ to $R^{203}$, $R^{206}$, $R^{207}$, $R^{211}$, and $R^{212}$ are bonded to one another to form a ring with a sulfur atom in the formula, these groups may be bonded via a hetero atom such as a sulfur atom, an oxygen atom or a nitrogen atom, or a functional group such as a carbonyl group, $—SO—$, $—SO_2—$, $—SO_3—$, $—COO—$, $—CONH—$ or $—N(R_N)—$ (here, $R_N$ represents an alkyl group having 1 to 5 carbon atoms). As a ring to be formed, a ring containing the sulfur atom in the formula in the skeleton thereof is preferably a 3- to 10-membered ring and most preferably a 5- to 7-membered ring including the sulfur atom. Specific examples of the ring to be formed include a thiophene ring, a thiazole ring, a benzothiophene ring, a thianthrene ring, a dibenzothiophene ring, a 9H-thioxanthene ring, a thioxanthone ring, a phenoxathiin ring, a tetrahydrothiophenium ring, and a tetrahydrothiopyranium ring.

$R^{208}$ and $R^{209}$ each independently represent a hydrogen atom or an alkyl group having 1 to 5 carbon atoms and preferably a hydrogen atom or an alkyl group having 1 to 3 carbon atoms. In a case where $R^{208}$ and $R^{209}$ each represent an alkyl group, $R^{208}$ and $R^{209}$ may be bonded to each other to form a ring.

$R^{210}$ represents an aryl group which may have a substituent, an alkyl group which may have a substituent, an alkenyl group which may have a substituent, or a $—SO_2$-containing cyclic group which may have a substituent.

Examples of the aryl group of $R^{210}$ include an unsubstituted aryl group having 6 to 20 carbon atoms, and a phenyl group or a naphthyl group is preferable.

As the alkyl group of $R^{210}$, a chain-like or cyclic alkyl group having 1 to 30 carbon atoms is preferable.

The alkenyl group of $R^{210}$ preferably has 2 to 10 carbon atoms.

As the $—SO_2$-containing cyclic group of $R^{210}$ which may have a substituent, the same groups as the $—SO_2$-containing cyclic group represented by Formulae (a5-r-1) to (a5-r-4) are exemplified. Among these, a "$—SO_2$-containing polycyclic group" is preferable, and a group represented by Formula (a5-r-1) is more preferable.

In Formulae (ca-4) and (ca-5), each $Y^{201}$ independently represents an arylene group, an alkylene group, or an alkenylene group.

Examples of the arylene group of $Y^{201}$ include groups in which one hydrogen atom has been removed from an aryl group exemplified as the aromatic hydrocarbon group represented by $R'^{201}$ described above.

Examples of the alkylene group and alkenylene group of $Y^{201}$ include groups in which one hydrogen atom has been removed from the chain-like alkyl group or the chain-like alkenyl group of $R'^{201}$.

In Formulae (ca-4) and (ca-5), x represents 1 or 2.

$W^{201}$ represents an (x+1)-valent linking group, that is, a divalent or trivalent linking group.

As the divalent linking group represented by $W^{201}$, a divalent hydrocarbon group which may have a substituent is preferable, and as examples thereof, the same hydrocarbon groups which may have a substituent as those described above represented by $Ya^{21}$ in Formula (a2-1) can be exemplified. The divalent linking group of $W^{201}$ may be linear, branched or cyclic, and cyclic is more preferable. Among these, an arylene group having two carbonyl groups, each bonded to the terminal thereof is preferable. Examples of the arylene group include a phenylene group and a naphthylene group, and a phenylene group is particularly preferable.

As the trivalent linking group of $W^{201}$, a group in which one hydrogen atom has been removed from the above-described divalent linking group of $W^{201}$ and a group in which the divalent linking group has been bonded to another divalent linking group can be exemplified. The trivalent linking group of $W^{201}$ is preferably a group in which two carbonyl groups are bonded to an arylene group.

Specific suitable examples of the cation represented by Formula (ca-1) include cations represented by Formulae (ca-1-1) to (ca-1-129) shown below.

(ca-1-1)
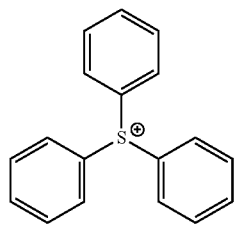

(ca-1-2)
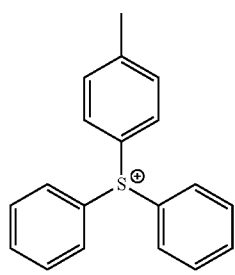

(ca-1-3)
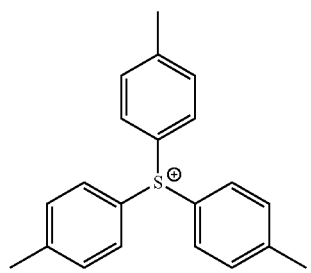

(ca-1-4)
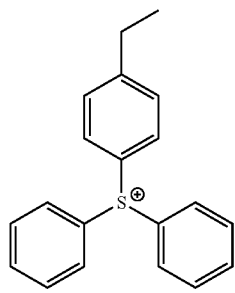

(ca-1-5)
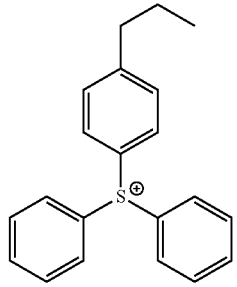

(ca-1-6)
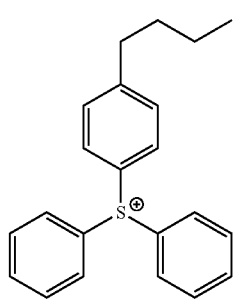

(ca-1-7)
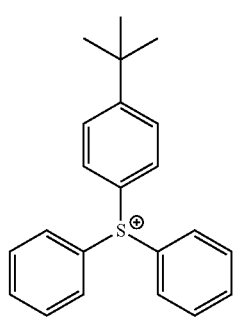

(ca-1-8)
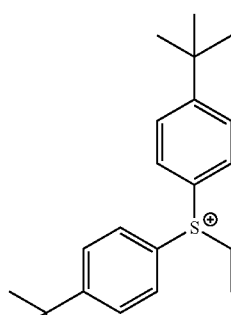

(ca-1-9)
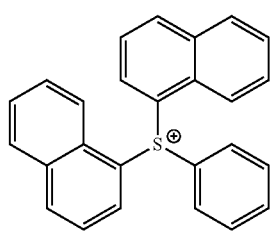

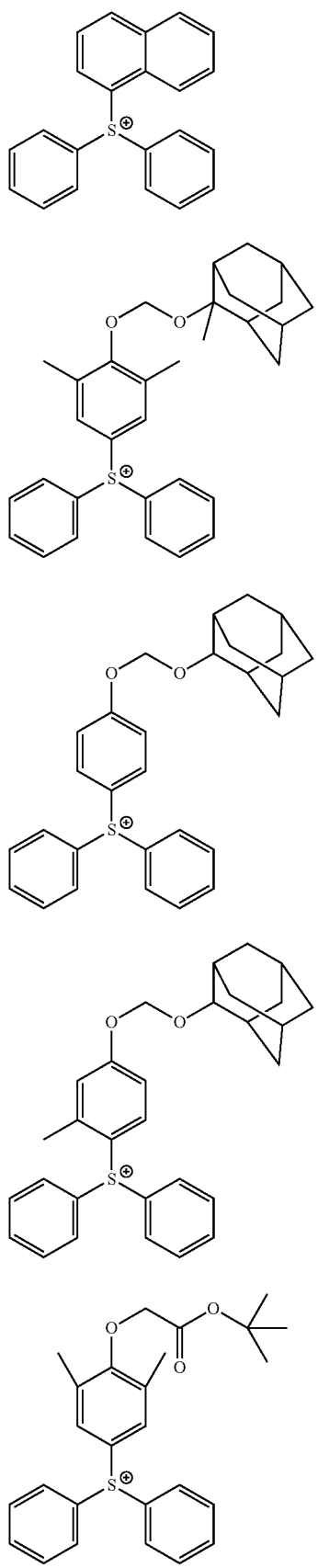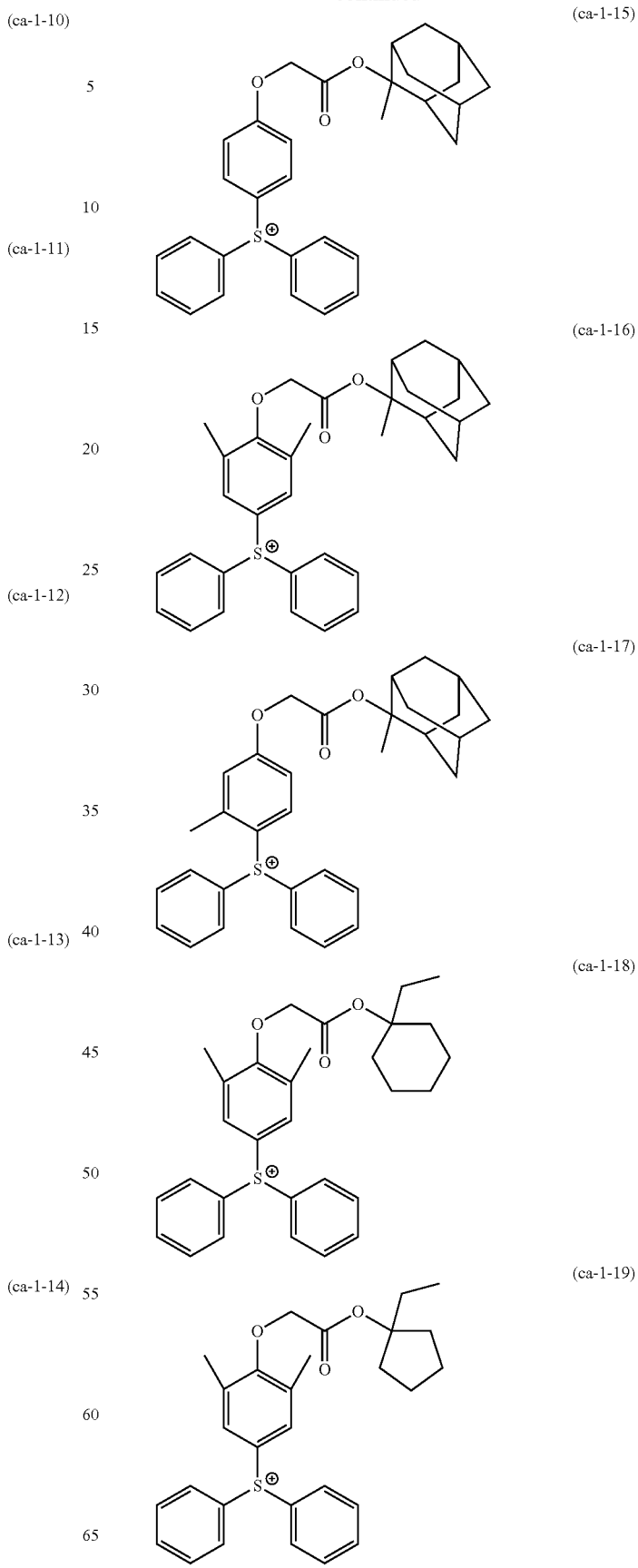

(ca-1-20)
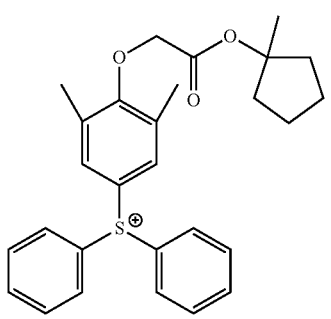
(ca-1-21)
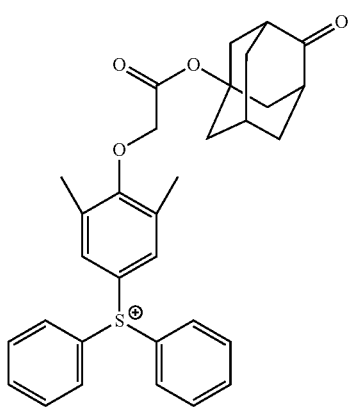
(ca-1-22)
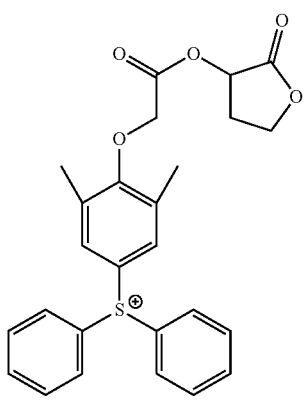
(ca-1-23)
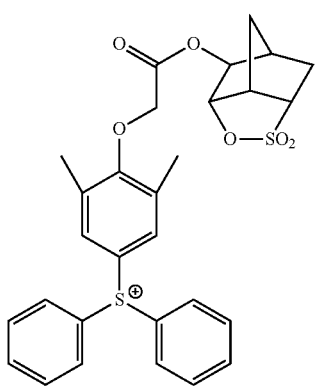
(ca-1-24)
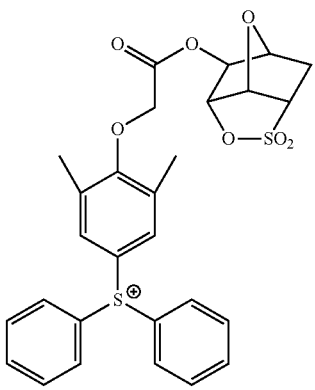
(ca-1-25)
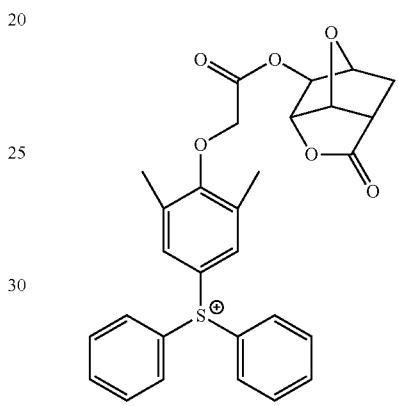
(ca-1-26)
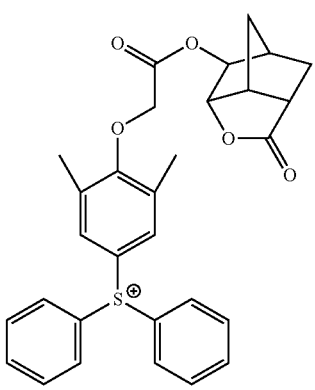
(ca-1-27)
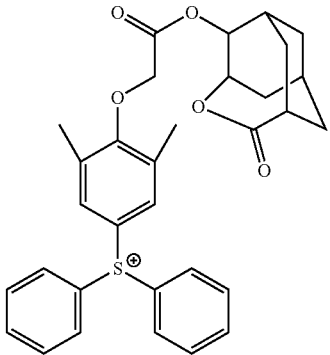

-continued
(ca-1-28)
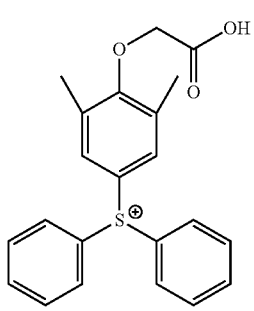
(ca-1-29)
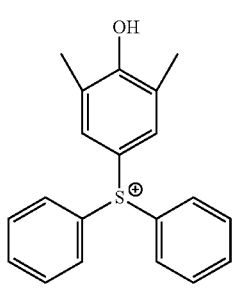
(ca-1-30)
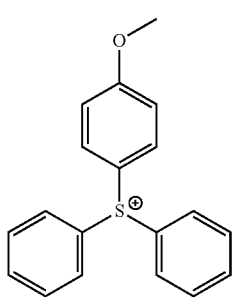
(ca-1-31)
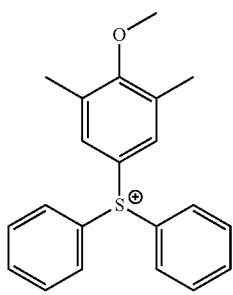
(ca-1-32)
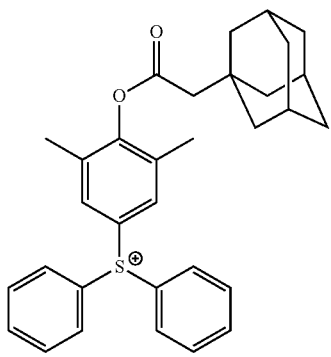
-continued
(ca-1-33)
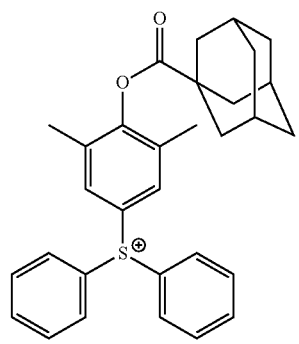
(ca-1-34)
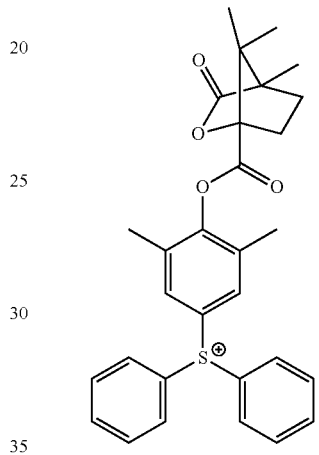
(ca-1-35)
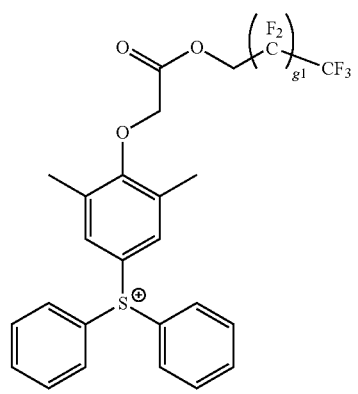
(ca-1-36)
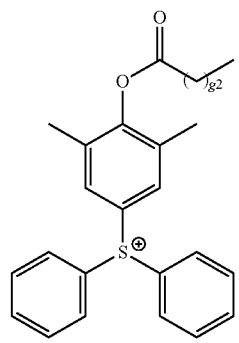

(ca-1-37) 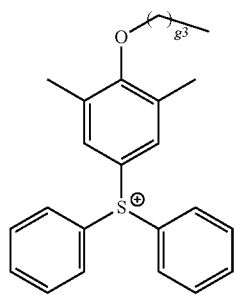
(ca-1-38) 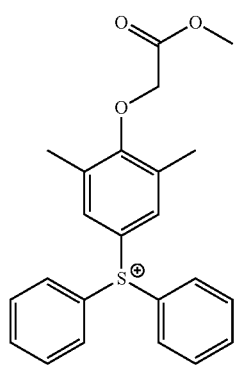
(ca-1-39) 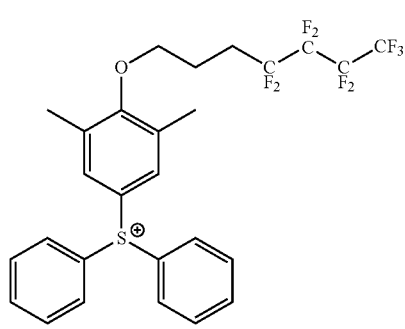
(ca-1-40) 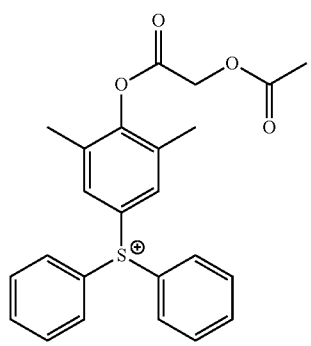
(ca-1-41) 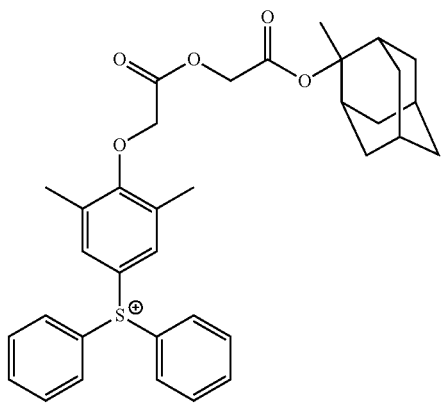
(ca-1-42) 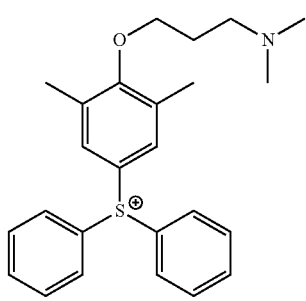
(ca-1-43) 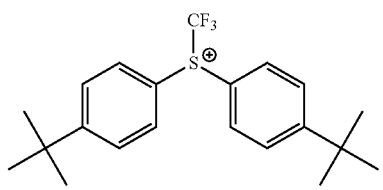
(ca-1-44) 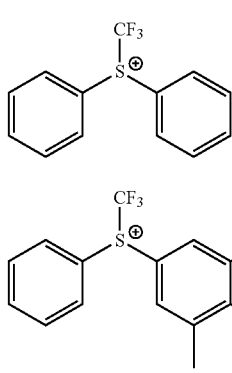
(ca-1-45) 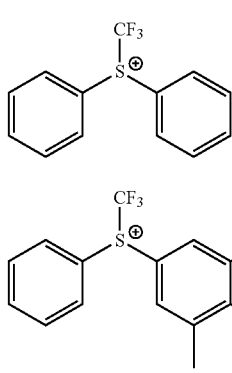
(ca-1-46) 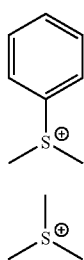
(ca-1-47) 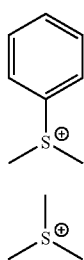

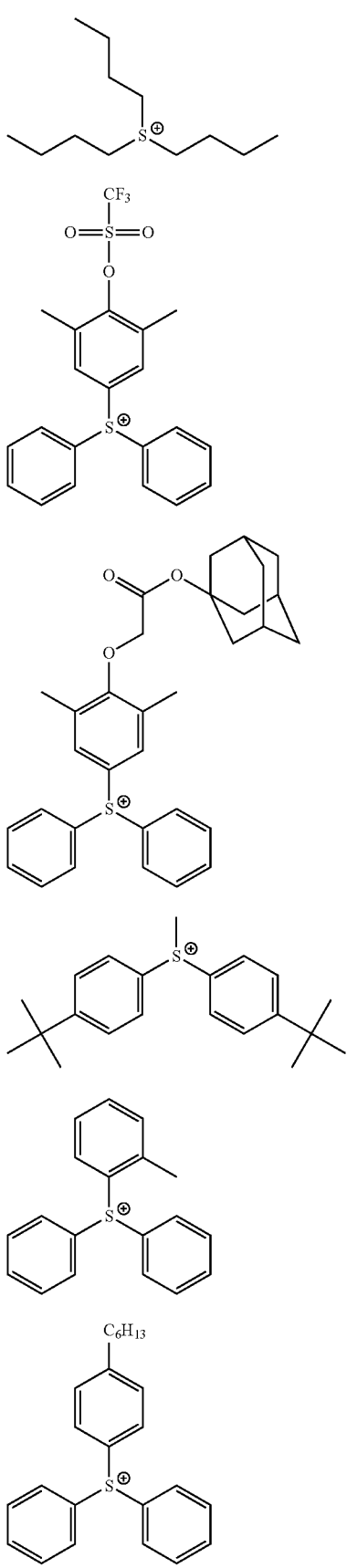
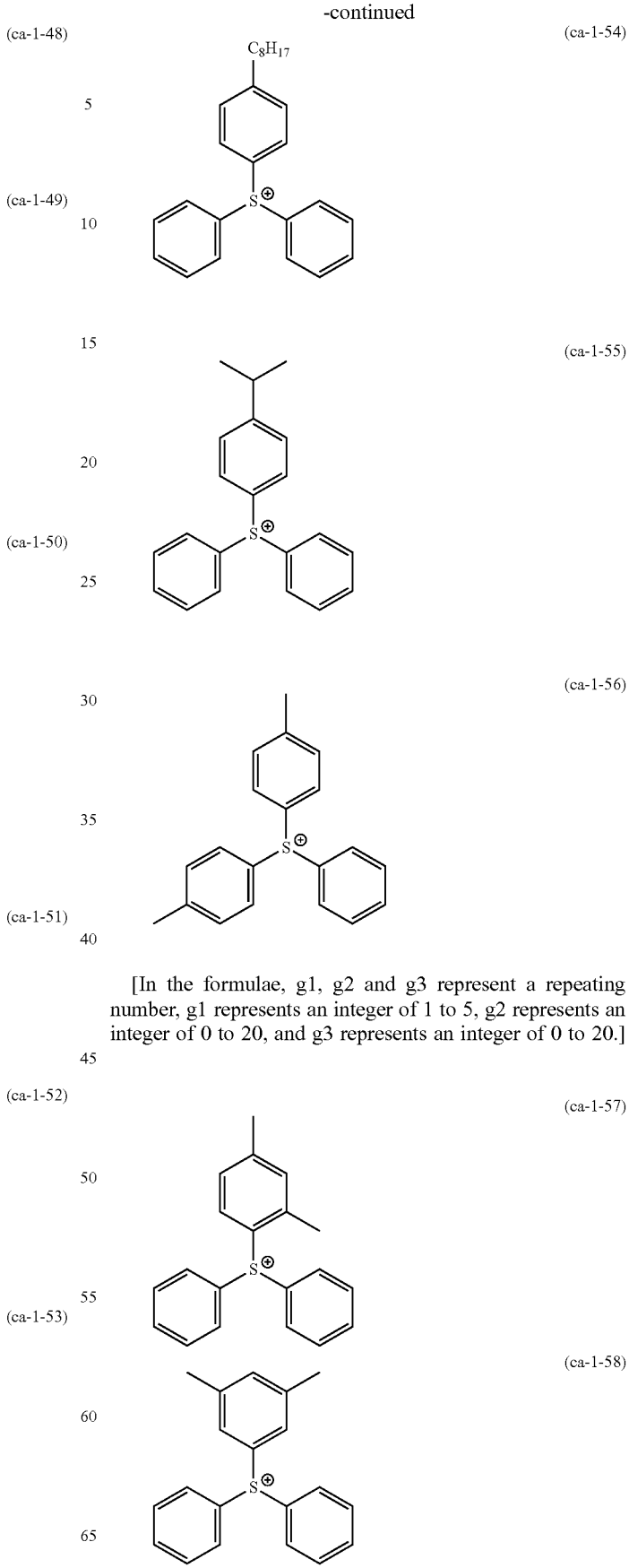
[In the formulae, g1, g2 and g3 represent a repeating number, g1 represents an integer of 1 to 5, g2 represents an integer of 0 to 20, and g3 represents an integer of 0 to 20.]

(ca-1-59)
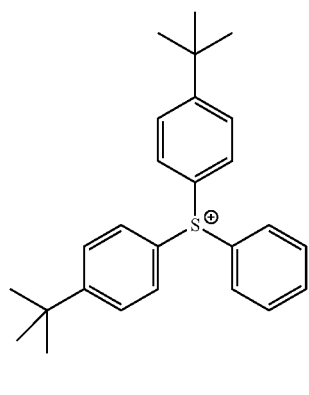
(ca-1-64)
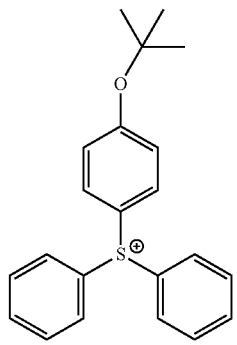
(ca-1-60)
(ca-1-65)
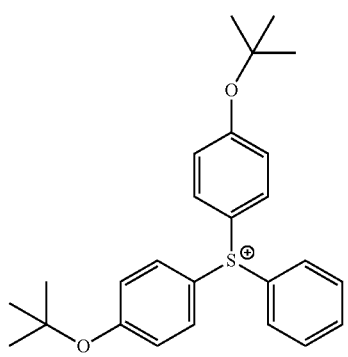
(ca-1-61)
(ca-1-66)
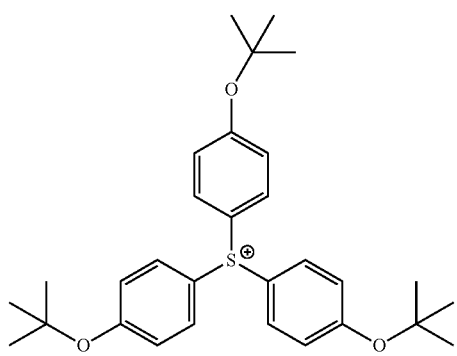
(ca-1-62)
(ca-1-63)
(ca-1-67)
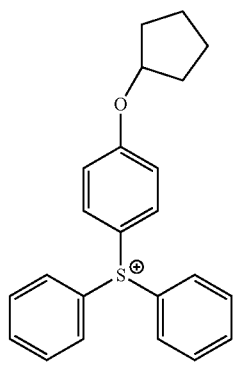
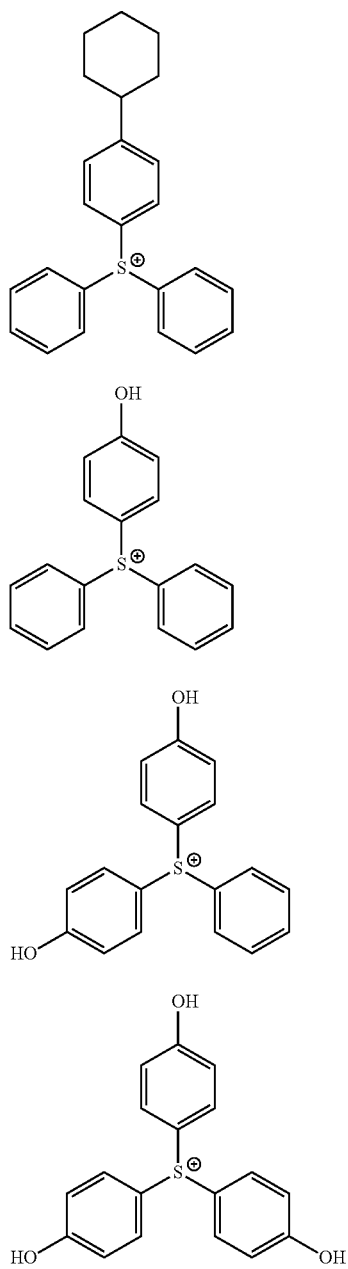

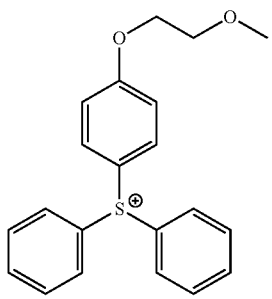 (ca-1-68)
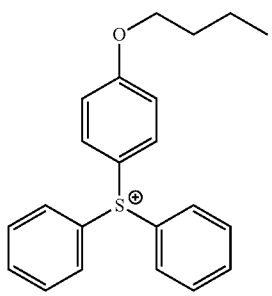 (ca-1-69)
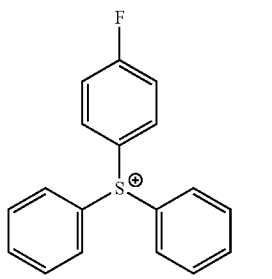 (ca-1-70)
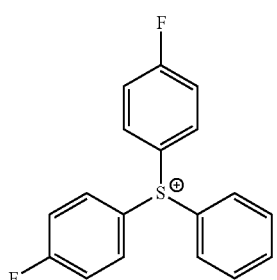 (ca-1-71)
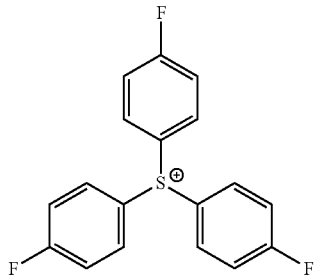 (ca-1-72)
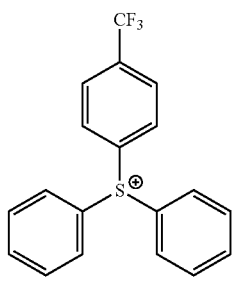 (ca-1-73)
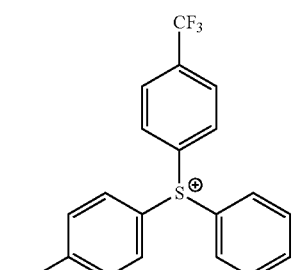 (ca-1-74)
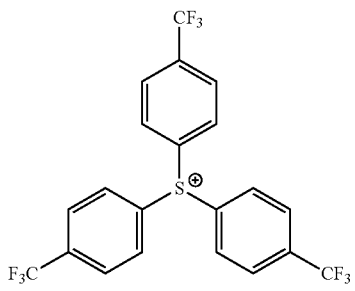 (ca-1-75)
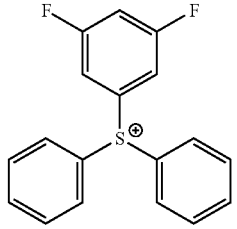 (ca-1-76)
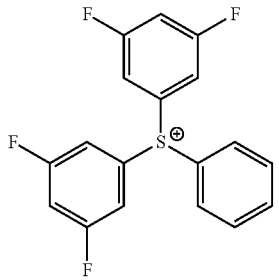 (ca-1-77)

-continued
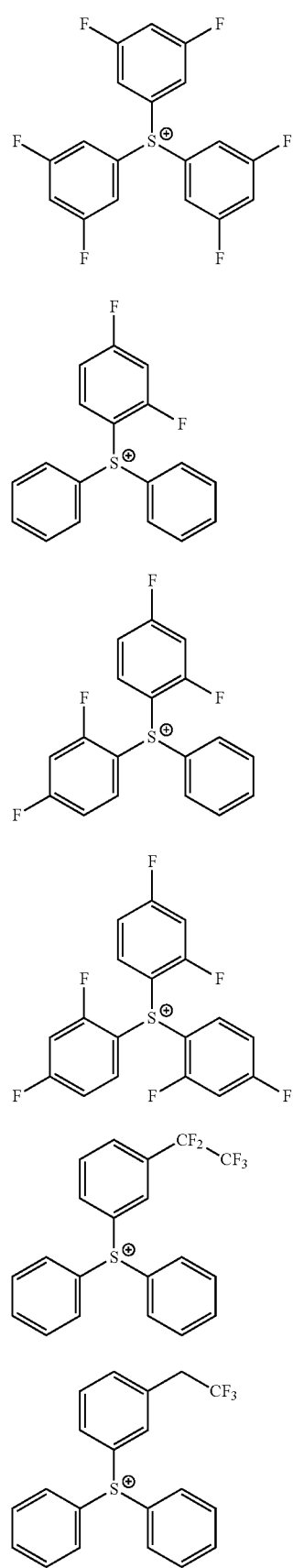
(ca-1-78)
(ca-1-79)
(ca-1-80)
(ca-1-81)
(ca-1-82)
(ca-1-83)
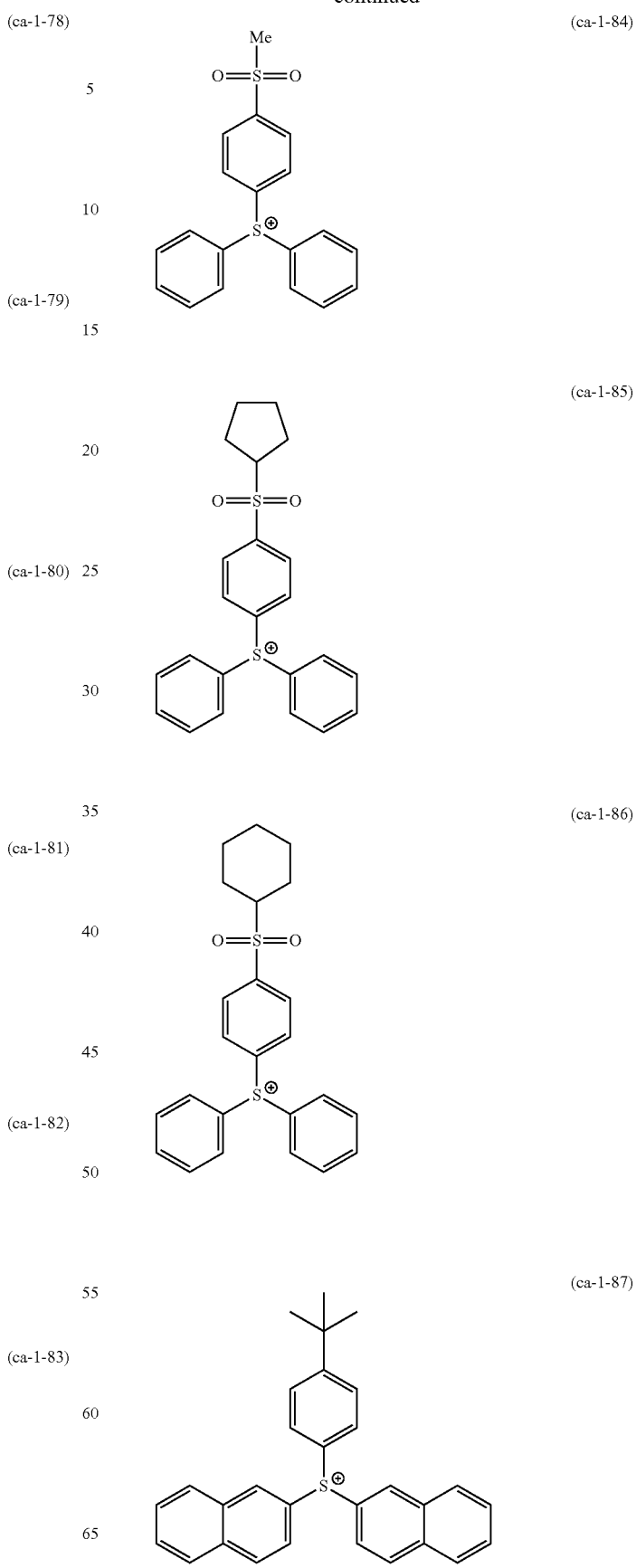
(ca-1-84)
(ca-1-85)
(ca-1-86)
(ca-1-87)

(ca-1-88)
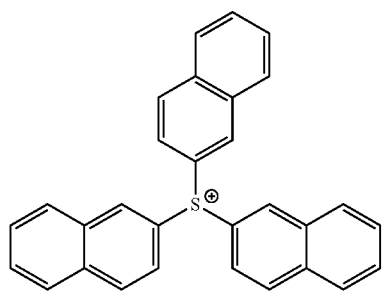
(ca-1-89)
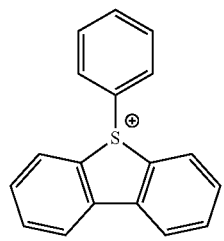
(ca-1-90)
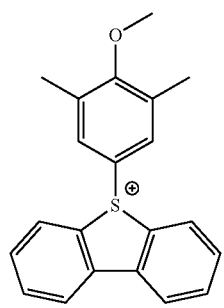
(ca-1-91)
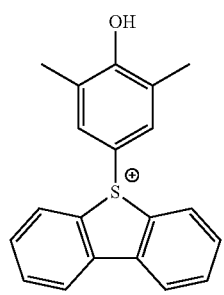
(ca-1-92)
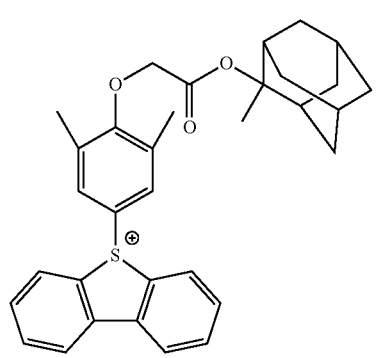
(ca-1-93)
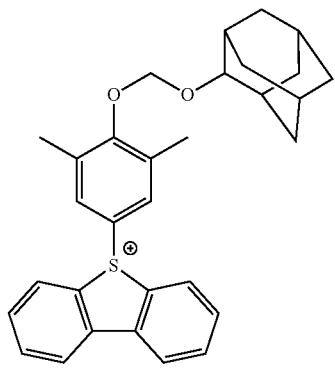
(ca-1-94)
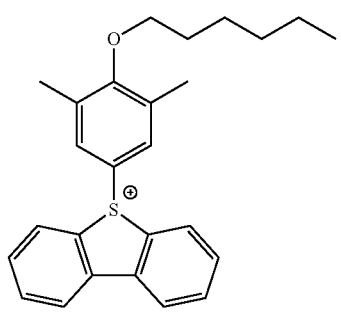
(ca-1-95)
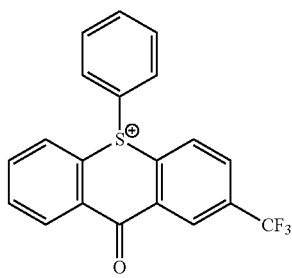
(ca-1-96)
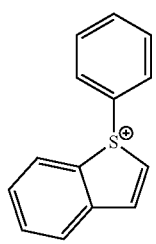
(ca-1-97)
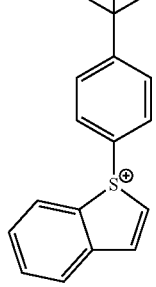

(ca-1-98)
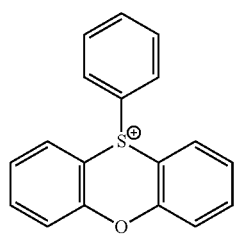
(ca-1-99)
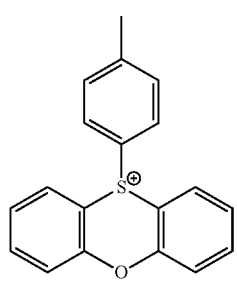
(ca-1-100)
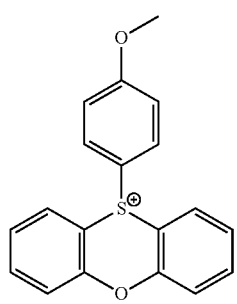
(ca-1-101)
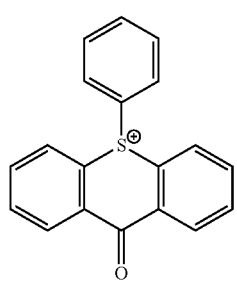
(ca-1-102)
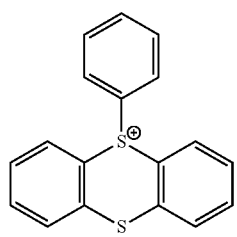
(ca-1-103)
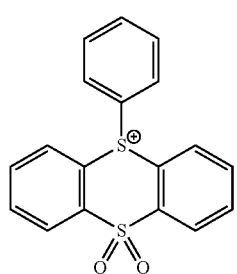
(ca-1-104)
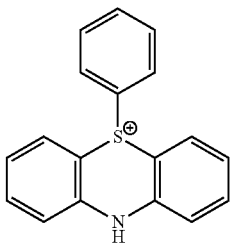
(ca-1-105)
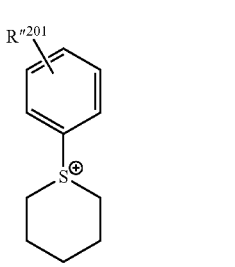
(ca-1-106)
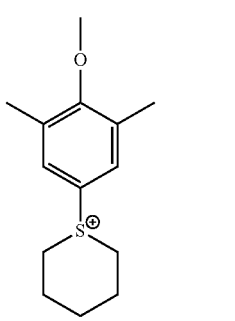
(ca-1-107)
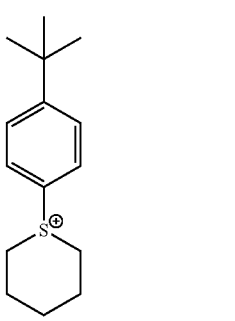
(ca-1-108)
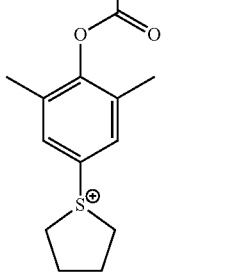

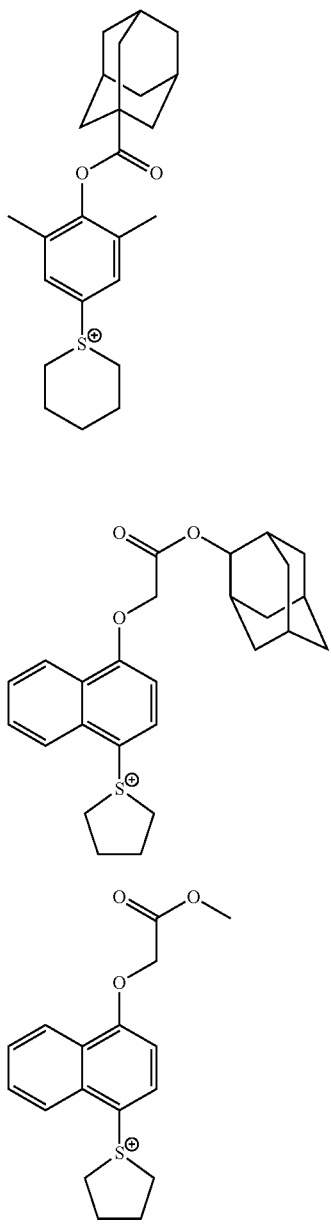
(ca-1-109)
(ca-1-110)
(ca-1-111)
[In the formulae, R"²⁰¹ represents a hydrogen atom or a substituent, and as the substituent, the same groups as those described above for substituting $R^{201}$ to $R^{207}$ and $R^{210}$ to $R^{212}$ can be exemplified.]
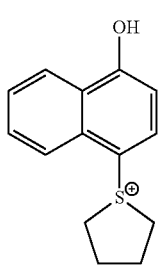
(ca-1-112)
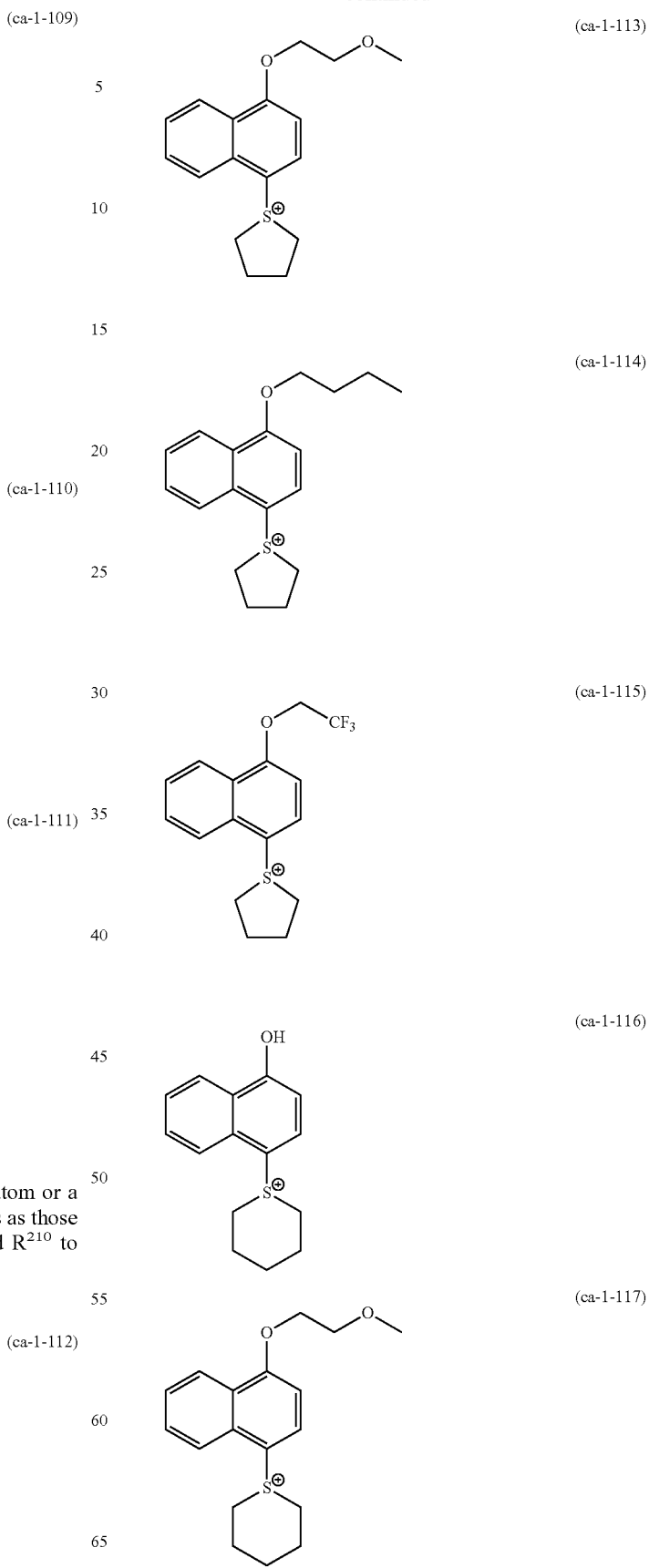
(ca-1-113)
(ca-1-114)
(ca-1-115)
(ca-1-116)
(ca-1-117)

(ca-1-118)
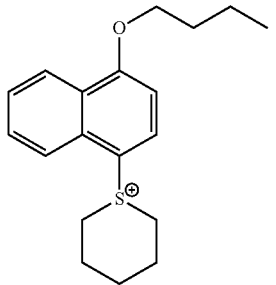
(ca-1-123)
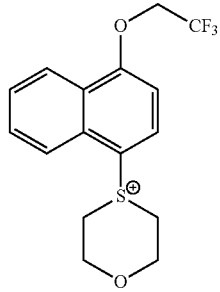
(ca-1-119)
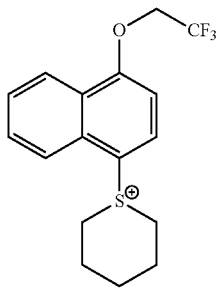
(ca-1-124)
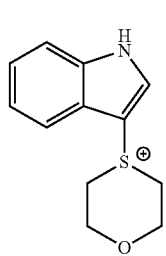
(ca-1-120)
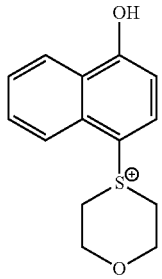
(ca-1-125)
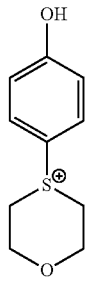
(ca-1-121)
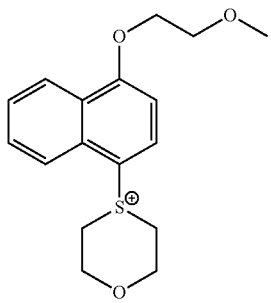
(ca-1-126)
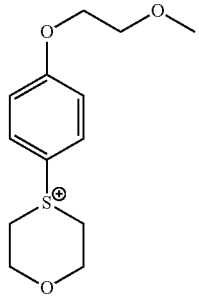
(ca-1-122)
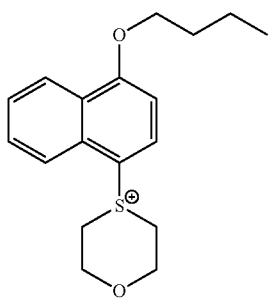
(ca-1-127)
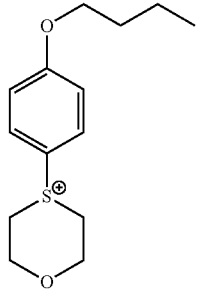

(ca-1-128)

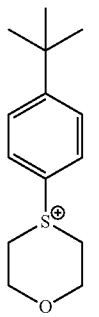

(ca-1-129)

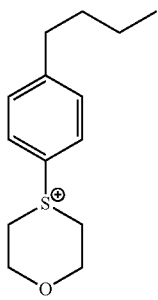

Specific examples of suitable cations represented by Formula (ca-2) include a dihphenyliodonium cation and a bis(4-tert-butylphenyl)iodonium cation.

Specific examples of suitable cations represented by Formula (ca-3) include cations represented by Formulae (ca-3-1) to (ca-3-6) shown below.

(ca-3-1)

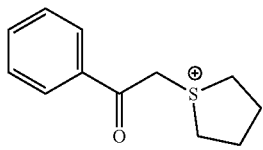

(ca-3-2)

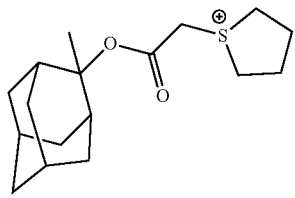

(ca-3-3)

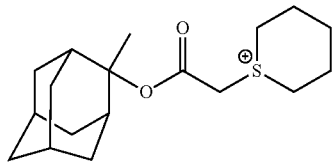

(ca-3-4)

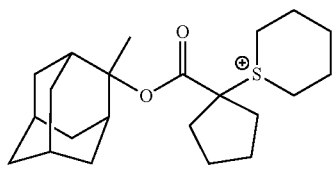

(ca-3-5)

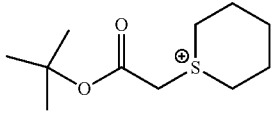

(ca-3-6)

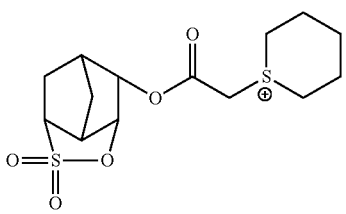

Specific examples of suitable cations represented by Formula (ca-4) include cations represented by Formulae (ca-4-1) and (ca-4-2) shown below.

(ca-4-1)

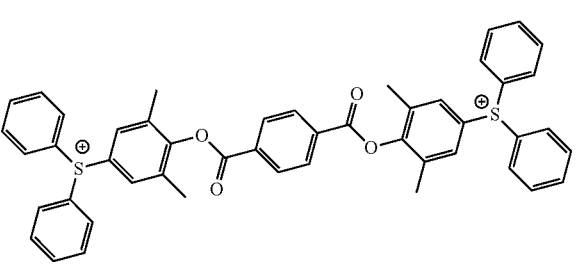

(ca-4-2)

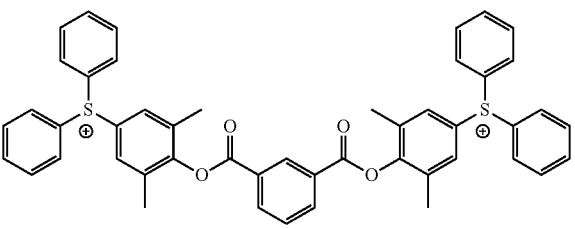

Further, as the cation represented by Formula (ca-5), cations represented by Formulae (ca-5-1) to (ca-5-3) are also preferable.

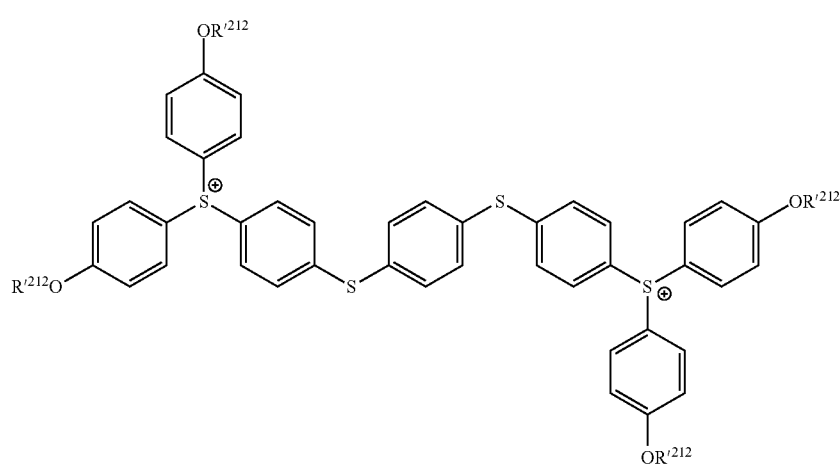
(ca-5-1)
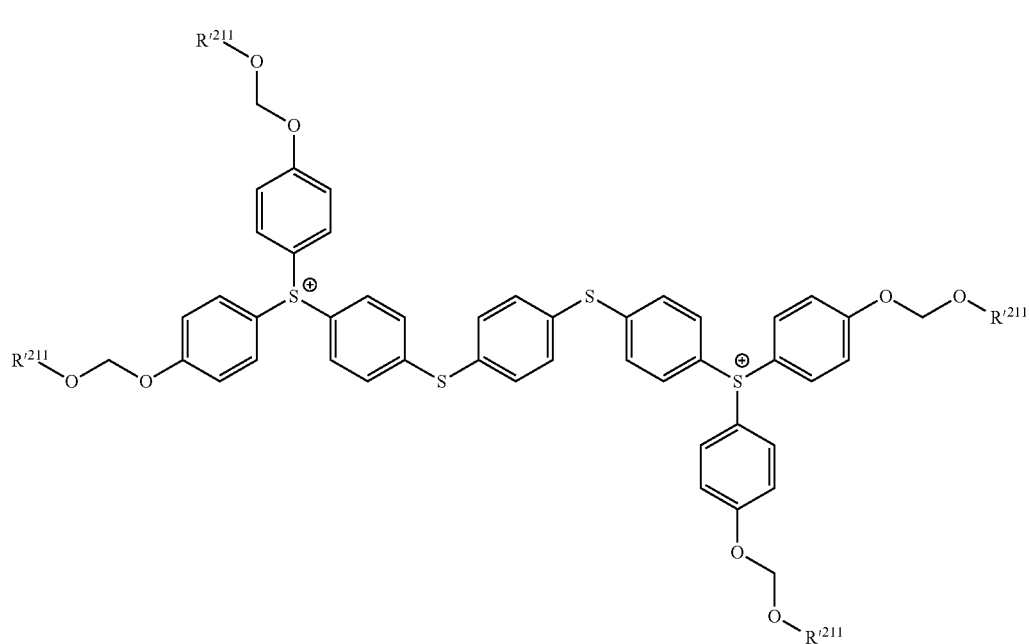
(ca-5-2)
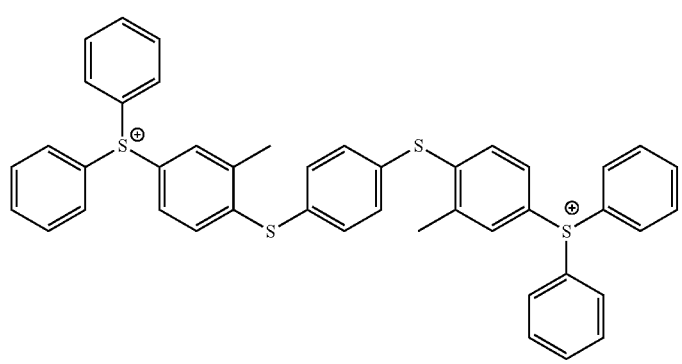
(ca-5-3)

Among the examples, as the cation moiety $[(M^{m+})_{1/m}]$, a cation represented by Formula (ca-1) is preferable, and a cation represented by any of Formulae (ca-1-1) to (ca-1-129) is more preferable.

Preferred examples of the component (B1) include a compound represented by Formula (b1-1).

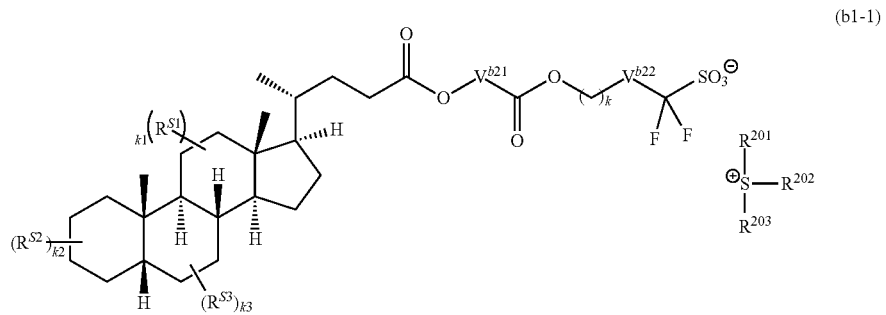

(b1-1)

[In the formula, $R^{S1}$ to $R^{S3}$, $V^{b21}$, $V^{b22}$, k1 to k3, k, and $R^{201}$ to $R^{203}$ each have the same definition as described above.]

Specific suitable examples of the component (B1) are shown below.

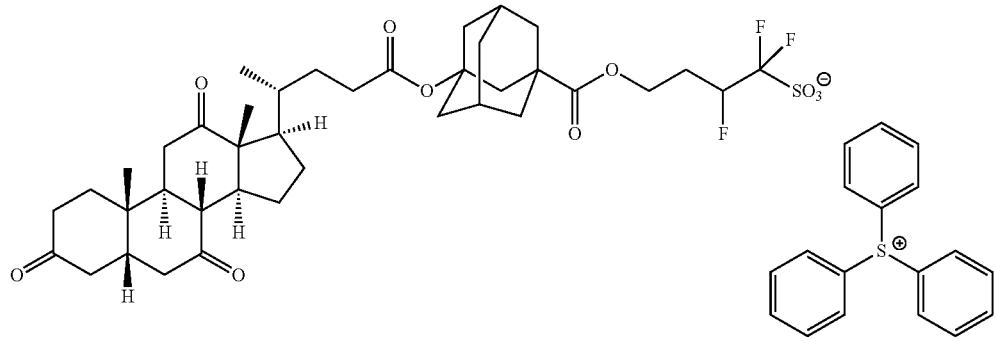

(B1-1)

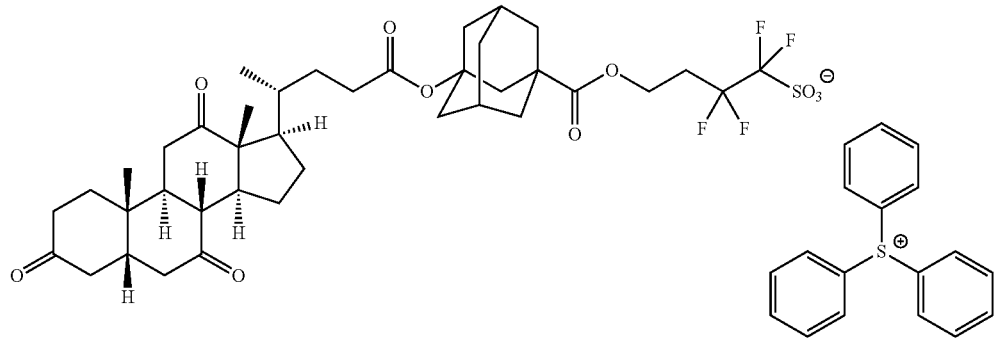

(B1-2)

-continued

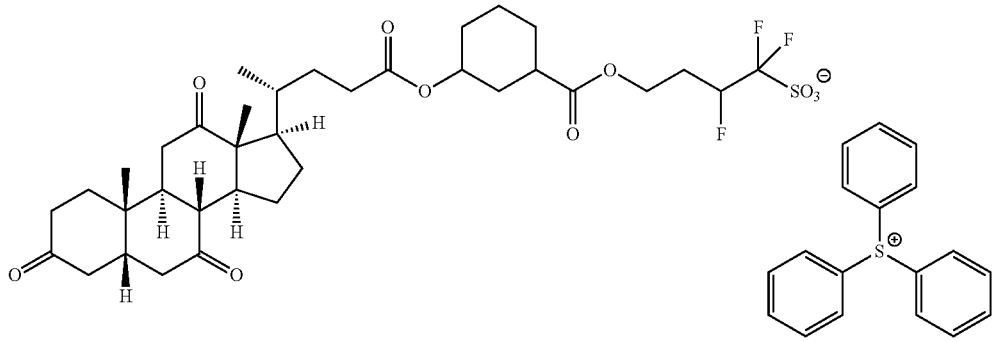

(B1-3)

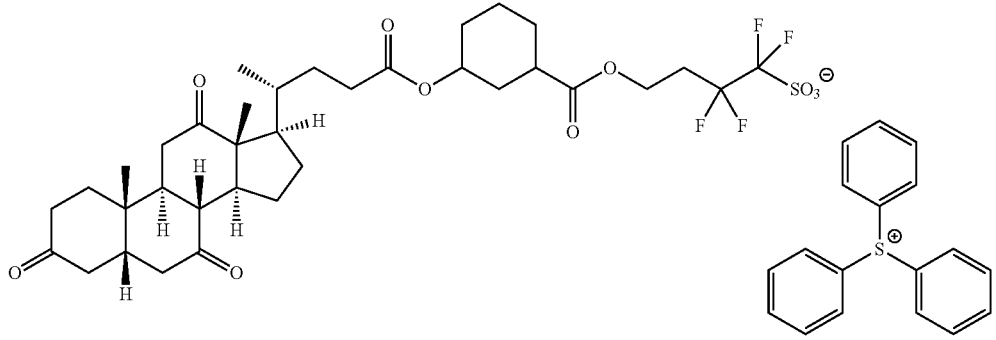

(B1-4)

In the resist composition of the present embodiment, the component (B1) may be used alone or in a combination of two or more kinds thereof.

The content of the component (B1) in the resist composition of the present embodiment is preferably in a range of 10 to 35 parts by mass, more preferably in a range of 10 to 25 parts by mass, and still more preferably in a range of 10 to 20 parts by mass with respect to 100 parts by mass of the component (A).

In a case where the content of the component (B1) is greater than or equal to the lower limit of the above-described preferable range, lithography characteristics such as CDU and DOF are further improved at the time of forming a resist pattern. Meanwhile, in a case where the content thereof is less than or equal to the upper limit of the above-described preferable range, a uniform solution is easily obtained and the storage stability of a resist composition is further increased at the time of dissolving each component of the resist composition in an organic solvent.

<<Component (B2)>>

The resist composition of the present embodiment may further contain an acid generator component (hereinafter, referred to as a "component (B2)") other than the component (B1) in a range not damaging the effects of the present invention, in addition to the component (B1).

The component (B2) is not particularly limited, and those which have been proposed as an acid generator for a chemically amplified resist in the related art can be used.

Examples of these acid generators are numerous and include onium salt acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As the onium salt acid generator, a compound represented by Formula (b-1) (hereinafter, also referred to as a "component (b-1)"), a compound represented by Formula (b-2) (hereinafter, also referred to as a "component (b-2)") or a compound represented by Formula (b-3) (hereinafter, also referred to as a "component (b-3)") can be used. Further, the component (b-1) does not contain a compound corresponding to the above-described component (B1).

$$R^{101}-Y^{101}-V^{101}\begin{matrix}R^{102}\\|\\-C-\\|\\F\end{matrix}SO_3^- \quad (M^{m+})_{1/m} \tag{b-1}$$

$$\begin{matrix}R^{104}-L^{101}-V^{102}-SO_2\\ \diagdown\\ N^-\\ \diagup\\ R^{105}-L^{102}-V^{103}-SO_2\end{matrix}(M^{m+})_{1/m} \tag{b-2}$$

$$\begin{matrix}R^{106}-L^{103}\\ \diagdown\\ R^{107}-L^{104}-C^-\\ \diagup\\ R^{108}-L^{105}\end{matrix}(M^{m+})_{1/m} \tag{b-3}$$

[In the formulae, $R^{101}$ and $R^{104}$ to $R^{108}$ each independently represent a cyclic group which may have a substituent, a chain-like alkyl group which may have a substituent, or a chain-like alkenyl group which may have a substituent, provided that $R^{104}$ and $R^{105}$ may be bonded to each other to form a ring.

$R^{102}$ represents a fluorine atom or a fluorinated alkyl group having 1 to 5 carbon atoms. $Y^{101}$ represents a single bond or a divalent linking group containing an oxygen atom. $V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO— or —SO$_2$—. m represents an integer of 1 or greater, and $M'^{m+}$ represents an m-valent onium cation.]

{Anion Moiety}

Anion Moiety of Component (b-1)

In Formula (b-1), $R^{101}$ represents a cyclic group which may have a substituent, a chain-like alkyl group which may have a substituent, or a chain-like alkenyl group which may have a substituent. The description for $R^{101}$ is the same as the description for the cyclic group which may have a substituent, the chain-like alkyl group which may have a substituent, or the chain-like alkenyl group which may have a substituent as $R'^{201}$ in formulae (ca-r-1) to (ca-r-7).

Among the examples, as $R^{101}$, a cyclic group which may have a substituent is preferable, and a cyclic hydrocarbon group which may have a substituent is more preferable. More specific preferred examples thereof include a phenyl group, a naphthyl group, a group in which one or more hydrogen atoms have been removed from a polycycloalkane, a lactone-containing cyclic group represented by any of Formulae (a2-r-1) and (a2-r-3) to (a2-r-7), and a —SO$_2$-containing cyclic group represented by any of Formulae (a5-r-1) to (a5-r-4).

In Formula (b-1), $Y^{101}$ represents a single bond or a divalent linking group containing an oxygen atom.

In a case where $Y^{101}$ represents a divalent linking group containing an oxygen atom, $Y^{101}$ may contain an atom other than an oxygen atom. Examples of atoms other than an oxygen atom include a carbon atom, a hydrogen atom, a sulfur atom, and a nitrogen atom.

Examples of the divalent linking group having an oxygen atom include linking groups represented by Formulae (y-a1-1) to (y-a1-8)

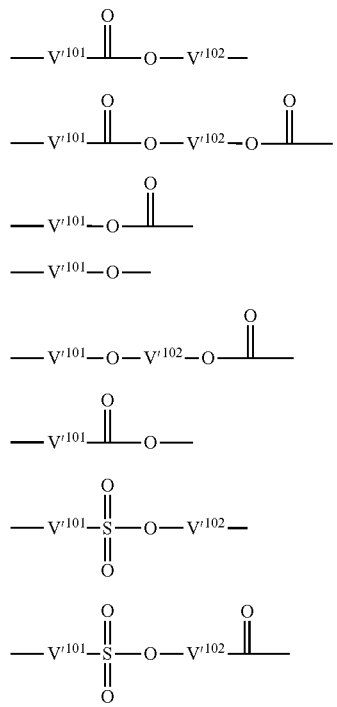

In Formula (b-1), $V^{101}$ represents a single bond, an alkylene group, or a fluorinated alkylene group. The alkylene group and the fluorinated alkylene group of $V^{101}$ preferably have 1 to 4 carbon atoms. Examples of the fluorinated alkylene group of $V^{101}$ include a group in which some or all hydrogen atoms in the alkylene group of $V^{101}$ have been substituted with fluorine atoms. Among these examples, as $V^{101}$, a single bond or a fluorinated alkylene group having 1 to 4 carbon atoms is preferable.

In Formula (b-1), $R^{102}$ represents a fluorine atom or a fluorinated alkyl group having 1 to 5 carbon atoms. $R^{102}$ preferably represents a fluorine atom or a perfluoroalkyl group having 1 to 5 carbon atoms and more preferably a fluorine atom.

As a specific example of the anion moiety for the component (b-1), in a case where $Y^{101}$ represents a single bond, a fluorinated alkylsulfonate anion such as a trifluoromethanesulfonate anion or a perfluorobutanesulfonate anion can be exemplified; and in a case where $Y^{101}$ represents a divalent linking group containing an oxygen atom, anions represented by Formulae (an-1) to (an-3) shown below can be exemplified.

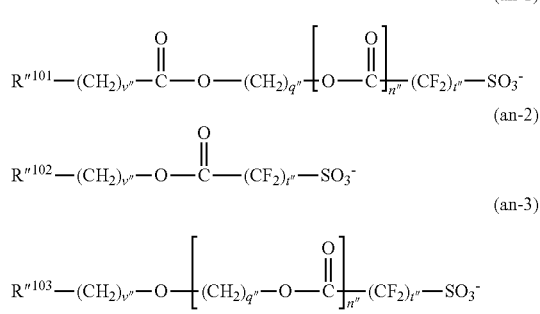

[In the formulae, $R'''^{101}$ represents an aliphatic cyclic group which may have a substituent, a group represented by any of Formulae (r-hr-1) to (r-hr-6), or a chain-like alkyl group which may have a substituent; $R'''^{102}$ represents an aliphatic cyclic group which may have a substituent, a lactone-containing cyclic group represented by any of Formulae (a2-r-1) and (a2-r-3) to (a2-r-7), or a —SO$_2$-containing cyclic group represented by any of Formulae (a5-r-1) to (a5-r-4); $R'''^{103}$ represents an aromatic cyclic group which may have a substituent, an aliphatic cyclic group which may have a substituent, or a chain-like alkenyl group which may have a substituent; each v" independently represents an integer of 0 to 3; each q" independently represents an integer of 1 to 20; t" represents an integer of 1 to 3; and n" represents 0 or 1.]

As the aliphatic cyclic group of $R'''^{101}$, $R'''^{102}$, and $R'''^{103}$ which may have a substituent, the same groups as the cyclic aliphatic hydrocarbon group of $R'^{201}$ described above are preferable. As the substituent, the same groups as the substituents which may substitute the cyclic aliphatic hydrocarbon group of $R'^{201}$ can be exemplified.

As the aromatic cyclic group of $R'''^{103}$ which may have a substituent, the same groups as the aromatic hydrocarbon group for the cyclic hydrocarbon group represented by $R'^{201}$ described above are preferable.

As the substituent, the same groups as the substituents which may substitute the aromatic hydrocarbon group of $R'^{201}$ can be exemplified.

As the chain-like alkyl group of $R'''^{101}$ which may have a substituent, the same groups exemplified as the chain-like alkyl groups represented by $R'^{201}$ are preferable. As the chain-like alkenyl group of $R''^{103}$ which may have a substituent, the same groups exemplified as the chain-like alkenyl groups represented by $R'^{201}$ are preferable.

Anion Moiety of Component (b-2)

In Formula (b-2), $R^{104}$ and $R^{105}$ each independently represent a cyclic group which may have a substituent, a chain-like alkyl group which may have a substituent or a chain-like alkenyl group which may have a substituent, and each have the same definition as that for $R'^{201}$. Here, $R^{104}$ and $R^{105}$ may be bonded to each other to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. It is preferable that the number of carbon atoms in the chain-like alkyl group of $R^{104}$ and $R^{105}$ be small because the solubility in a solvent for a resist is also excellent in such a range of the number of carbon atoms. Further, in the chain-like alkyl group of $R^{104}$ and $R^{105}$, it is preferable that the number of hydrogen atoms substituted with fluorine atoms be as large as possible because the acid strength increases and the transparency to high energy radiation of 200 nm or less or electron beams is improved.

The proportion of fluorine atoms in the chain-like alkyl group, that is, the fluorination ratio is preferably in a range of 70% to 100% and more preferably in a range of 90% to 100%, and it is most preferable that the chain-like alkyl group be a perfluoroalkyl group in which all hydrogen atoms are substituted with fluorine atoms.

In Formula (b-2), $V^{102}$ and $V^{103}$ each independently represent a single bond, an alkylene group, or a fluorinated alkylene group, and have the same definition as that for $V^{101}$ in Formula (b-1).

In Formula (b-2), $L^{101}$ and $L^{102}$ each independently represent a single bond or an oxygen atom.

Anion Moiety of Component (b-3)

In Formula (b-3), $R^{106}$ to $R^{108}$ each independently represent a cyclic group which may have a substituent, a chain-like alkyl group which may have a substituent, or a chain-like alkenyl group which may have a substituent, and have the same definition as that for $R'^{201}$.

$L^{103}$ to $L^{105}$ each independently represent a single bond, —CO—, or —SO$_2$—.

{Cation Moiety}

In Formulae (b-1), (b-2), and (b-3), m represents an integer of 1 or greater, $M^{m+}$ represents an m-valent onium cation and preferably a sulfonium cation or an iodonium cation. Further, an organic cation represented by any of Formulae (ca-1) to (ca-5) is particularly preferable.

Specific suitable examples of the cation represented by Formula (ca-1) include cations represented by Formulae (ca-1-1) to (ca-1-129).

Specific suitable examples of the cation represented by Formula (ca-2) include a diphenyliodonium cation and a bis(4-tert-butylphenyl)iodonium cation.

Specific suitable examples of the cation represented by Formula (ca-3) include cations represented by Formulae (ca-3-1) to (ca-3-6).

Specific suitable examples of the cation represented by Formula (ca-4) include cations represented by Formulae (ca-4-1) and (ca-4-2).

Specific suitable examples of the cation represented by Formula (ca-5) include cations represented by Formulae (ca-5-1) to (ca-5-3).

Among the examples, as the cation moiety $[(M^{m+})_{1/m}]$, a cation represented by Formula (ca-1) is preferable, and a cation represented by any of Formulae (ca-1-1) to (ca-1-129) is more preferable.

In the resist composition of the present embodiment, the component (B2) may be used alone or in a combination of two or more kinds thereof.

If the resist composition contains the component (B2), the content of the component (B2) in the resist composition is preferably 50 parts by mass or less, more preferably in a range of 1 to 40 parts by mass, and still more preferably in a range of 5 to 30 parts by mass with respect to 100 parts by mass of the component (A).

By setting the content of the component (B2) to be in the above-described range, pattern formation is sufficiently performed. Further, since a uniform solvent is easily obtained and the storage stability of the resist composition becomes excellent at the time of dissolving each component of the resist composition in an organic solvent, it is preferable that the content of the component (B2) be in the above-described range.

<Other Components>

The resist composition of the present embodiment may further contain components in addition to the component (A) and the component (B).

As other components, a component (D), a component (E), a component (F), and a component (S) described below are exemplified.

<<Component (D): Acid Diffusion Control Agent Component>>

The resist composition of the present embodiment may further contain an acid diffusion control agent component (hereinafter, referred to as a "component (D)") in addition to the component (A) or the component (A) and the component (B). The component (D) acts as a quencher (an acid diffusion control agent) which traps the acid generated in the resist composition upon exposure.

The component (D) may be a photodecomposable base (D1) (hereinafter, referred to as a "component (D1)") which is decomposed upon exposure and then loses the acid diffusion controllability or a nitrogen-containing organic compound (D2) (hereinafter, referred to as a "component (D2)") which does not correspond to the component (D1).

In Regard to Component (D1)

In a case where a resist composition containing the component (D1) is obtained, the contrast between exposed portions and unexposed portions of the resist film can be further improved at the time of formation of a resist pattern.

The component (D1) is not particularly limited as long as decomposition occurs upon exposure so that the acid diffusion controllability is lost, and one or more compounds selected from the group consisting of a compound represented by Formula (d1-1) (hereinafter, referred to as a "component (d1-1)"), a compound represented by Formula (d1-2) (hereinafter, referred to as a "component (d1-2)"), and a compound represented by Formula (d1-3) (hereinafter, referred to as a "component (d1-3)") are preferable.

At exposed portions of the resist film, the components (d1-1) to (d1-3) are decomposed and then lose the acid diffusion controllability (basicity), and therefore the components (d1-1) to (d1-3) cannot act as a quencher, whereas at unexposed portions of the resist film, the components (d1-1) to (d1-3) act as a quencher.

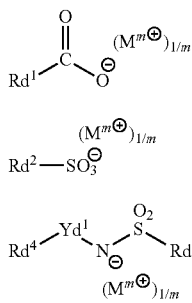

(d1-1)

(d1-2)

(d1-3)

[In the formulae, $Rd^1$ to $Rd^4$ represent a cyclic group which may have a substituent, a chain-like alkyl group which may have a substituent or a chain-like alkenyl group which may have a substituent, provided that the carbon atom adjacent to the sulfur atom in the $Rd^2$ in Formula (d1-2) has no fluorine atom bonded thereto; $Yd^1$ represents a single bond or a divalent linking group; m represents an integer of 1 or greater; and each $M^{m+}$ independently represents an m-valent organic cation.]

{Component (d1-1)}
Anion Moiety

In Formula (d1-1), $Rd^1$ represents a cyclic group which may have a substituent, a chain-like alkyl group which may have a substituent or a chain-like alkenyl group which may have a substituent, and examples thereof are the same as those described above as $R'^{201}$.

Among these, as the group of $Rd^1$, an aromatic hydrocarbon group which may have a substituent, an aliphatic cyclic group which may have a substituent and a chain-like alkyl group which may have a substituent are preferable. Examples of the substituent for these groups include a hydroxyl group, an oxo group, an alkyl group, an aryl group, a fluorine atom, a fluorinated alkyl group, a lactone-containing cyclic group represented by any of Formulae (a2-r-1) to (a2-r-7), an ether bond, an ester bond, and a combination thereof. In a case where an ether bond or an ester bond is included as the substituent, the substituent may be bonded via an alkylene group, and a linking group represented by any of Formulae (y-a1-1) to (y-a1-5) is preferable as the substituent.

Suitable examples of the aromatic hydrocarbon group include a phenyl group, a naphthyl group, and a polycyclic structure (a polycyclic structure formed of a bicyclooctane skeleton and a ring structure other than the bicyclooctane skeleton) containing a bicyclooctane skeleton.

Examples of the aliphatic cyclic group include groups in which one or more hydrogen atoms have been removed from a polycycloalkane such as adamantane, norbornane, isobornane, tricyclodecane or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl group, or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, or a 4-methylpentyl group.

In a case where the chain-like alkyl group is a fluorinated alkyl group having a fluorine atom or a fluorinated alkyl group serving as a substituent, the fluorinated alkyl group preferably has 1 to 11 carbon atoms, more preferably 1 to 8 carbon atoms, and still more preferably 1 to 4 carbon atoms. The fluorinated alkyl group may contain an atom other than fluorine. Examples of the atom other than fluorine include an oxygen atom, a sulfur atom, and a nitrogen atom.

As $Rd^1$, a fluorinated alkyl group in which some or all hydrogen atoms constituting a linear alkyl group have been substituted with fluorine atoms is preferable, and a fluorinated alkyl group in which all of the hydrogen atoms constituting a linear alkyl group have been substituted with fluorine atoms (a linear perfluoroalkyl group) is particularly preferable.

Specific examples of preferable anion moieties for the component (d1-1) are shown below.

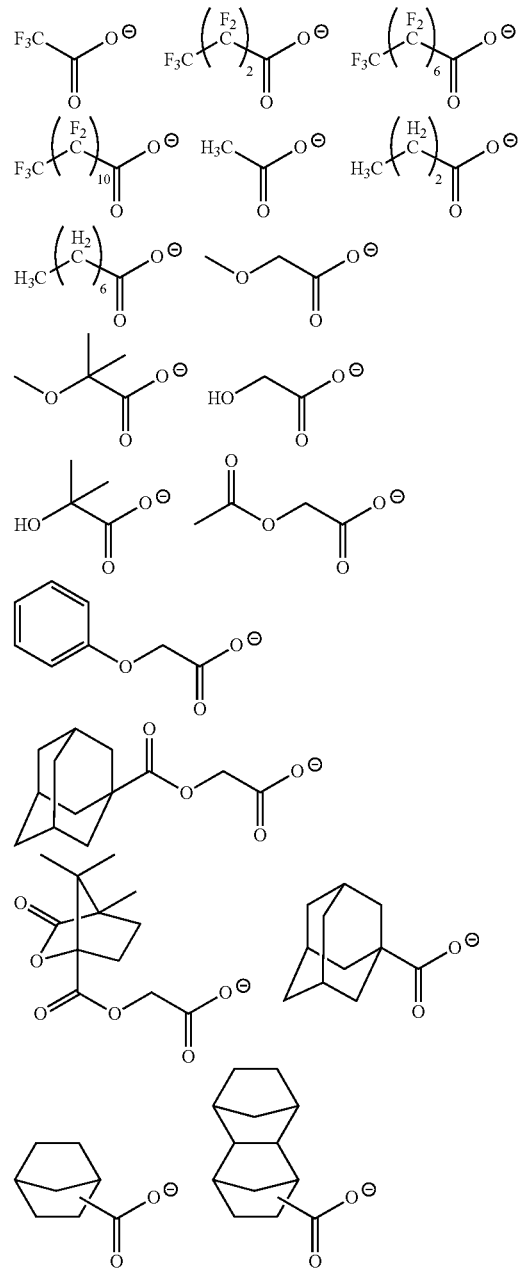

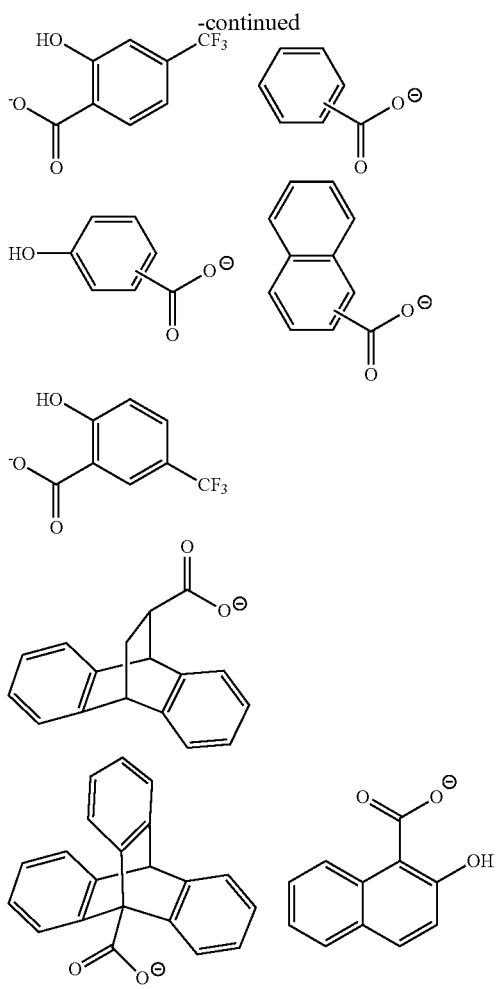

Cation Moiety

In Formula (d1-1), $M^{m+}$ represents an m-valent organic cation.

As the organic cation as $M^{m+}$, the same cations as those represented by Formulae (ca-1) to (ca-5) are suitably exemplified, a cation represented by the above-described Formulae (ca-1) is more preferable, and cations represented Formulae (ca-1-1) to (ca-1-129) are still more preferable.

The component (d1-1) may be used alone or in a combination of two or more kinds thereof.

{Component (d1-2)}

Anion Moiety

In Formula (d1-2), $Rd^2$ represents a cyclic group which may have a substituent, a chain-like alkyl group which may have a substituent, or a chain-like alkenyl group which may have a substituent, and the same groups as those described above as $R'^{201}$ are exemplified.

Here, the carbon atom adjacent to the S atom in $Rd^2$ has no fluorine atom bonded thereto (the carbon atom adjacent to the sulfur atom in $Rd^2$ is not substituted with a fluorine atom). As a result, the anion of the component (d1-2) becomes an appropriately weak acid anion, thereby improving the quenching ability of the component (D).

As $Rd^2$, a chain-like alkyl group which may have a substituent or an aliphatic cyclic group which may have a substituent is preferable. The chain-like alkyl group preferably has 1 to 10 carbon atoms and more preferably 3 to 10 carbon atoms. As the aliphatic cyclic group, a group in which one or more hydrogen atoms have been removed from adamantane, norbornane, isobornane, tricyclodecane, or tetracyclododecane (which may have a substituent) and a group in which one or more hydrogen atoms have been removed from camphor are more preferable.

The hydrocarbon group of $Rd^2$ may have a substituent. As the substituent, the same groups as the substituents which may be included in the hydrocarbon group (such as an aromatic hydrocarbon group, an aliphatic cyclic group, or a chain-like alkyl group) of $Rd^1$ in Formula (d1-1) can be exemplified.

Specific examples of preferable anion moieties for the component (d1-2) are shown below.

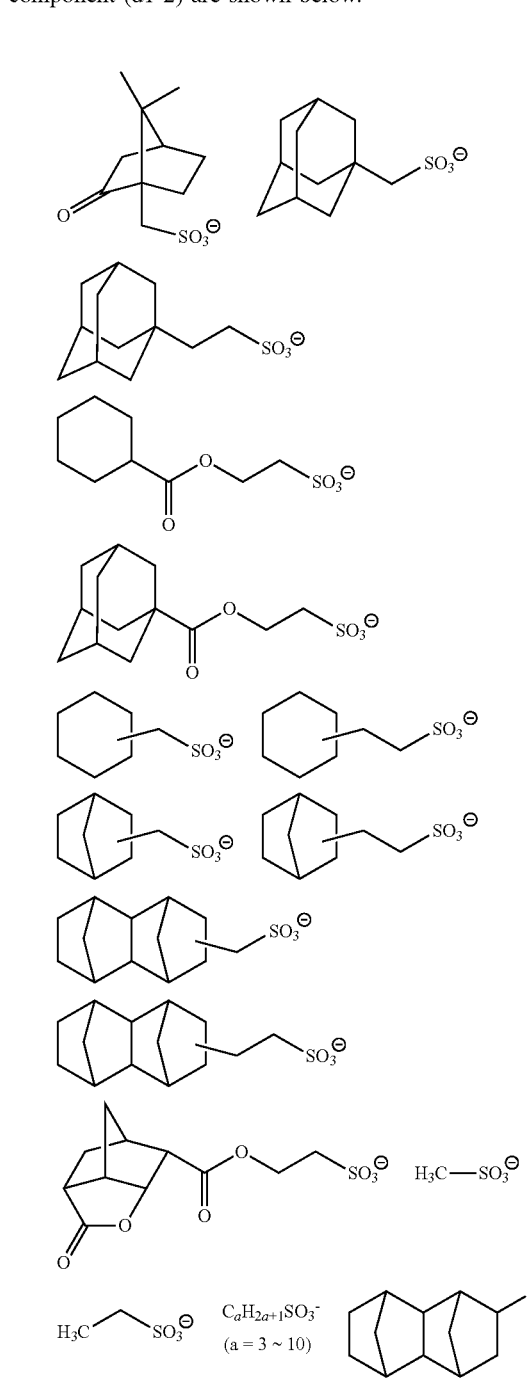

-continued

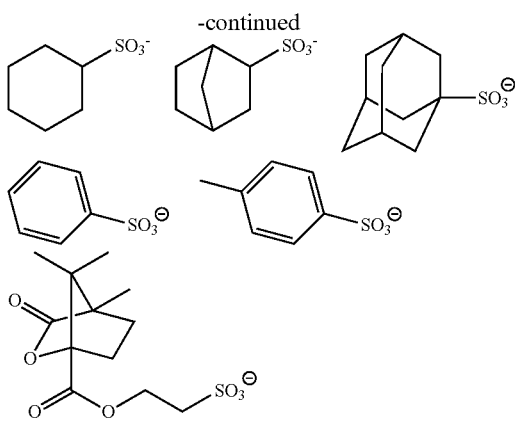

Cation Moiety

In Formula (d1-2), $M^{m+}$ represents an m-valent organic cation, and has the same definition as that for $M^{m+}$ in the above-described Formula (d1-1).

The component (d1-2) may be used alone or in a combination of two or more kinds thereof.

{Component (d1-3)}
Anion Moiety

In Formula (d1-3), $Rd^3$ represents a cyclic group which may have a substituent, a chain-like alkyl group which may have a substituent, or a chain-like alkenyl group which may have a substituent, and the same groups as those described above as $R'^{201}$ are exemplified, and a cyclic group containing a fluorine atom, a chain-like alkyl group, or a chain-like alkenyl group is preferable. Among these, a fluorinated alkyl group is preferable, and the same fluorinated alkyl groups as those described above as $Rd^1$ are more preferable.

In Formula (d1-3), $Rd^4$ represents a cyclic group which may have a substituent, a chain-like alkyl group which may have a substituent or a chain-like alkenyl group which may have a substituent, and the same groups as those described above as $R'^{201}$ are exemplified.

Among these, an alkyl group which may have substituent, an alkoxy group which may have substituent, an alkenyl group which may have substituent, or a cyclic group which may have substituent is preferable.

The alkyl group of $Rd^4$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. Some hydrogen atoms in the alkyl group of $Rd^4$ may be substituted with a hydroxyl group, a cyano group, or the like.

The alkoxy group of $Rd^4$ is preferably an alkoxy group having 1 to 5 carbon atoms, and specific examples thereof include a methoxy group, an ethoxy group, an n-propoxy group, an iso-propoxy group, an n-butoxy group, and a tert-butoxy group. Among these, a methoxy group and an ethoxy group are preferable.

Examples of the alkenyl group of $Rd^4$ are the same as those exemplified as the alkenyl group represented by $R'^{201}$, and a vinyl group, a propenyl group (an allyl group), a 1-methylpropenyl group, and a 2-methylpropenyl group are preferable. These groups may have an alkyl group having 1 to 5 carbon atoms or a halogenated alkyl group having 1 to 5 carbon atoms as a substituent.

As the cyclic group of $Rd^4$, the same groups as those described above as $R'^{201}$ can be exemplified. Among these, as the cyclic group, an alicyclic group in which one or more hydrogen atoms have been removed from a cycloalkane such as cyclopentane, cyclohexane, adamantane, norbornane, isobornane, tricyclodecane or tetracyclododecane or an aromatic group such as a phenyl group or a naphthyl group is preferable. In a case where $Rd^4$ represents an alicyclic group, the resist composition can be satisfactorily dissolved in an organic solvent, thereby improving the lithography characteristics. Further, in a case where $Rd^4$ represents an aromatic group, the resist composition exhibits excellent photoabsorption efficiency in a lithography process using EUV or the like as the exposure light source, thereby resulting in the improvement of the sensitivity and the lithography characteristics.

In Formula (d1-3), $Yd^1$ represents a single bond or a divalent linking group.

The divalent linking group of $Yd^1$ is not particularly limited, and examples thereof include a divalent hydrocarbon group (an aliphatic hydrocarbon group or an aromatic hydrocarbon group) which may have a substituent and a divalent linking group containing a hetero atom. The divalent linking groups are the same as described above as the divalent hydrocarbon group which may have a substituent and the divalent linking group containing a hetero atom explained above as the divalent linking group of $Ya^{21}$ in Formula (a2-1).

As $Yd^1$, a carbonyl group, an ester bond, an amide bond, an alkylene group, or a combination of these is preferable. As the alkylene group, a linear or branched alkylene group is more preferable, and a methylene group or an ethylene group is still more preferable.

Specific examples of preferable anion moieties for the component (d1-3) are shown below.

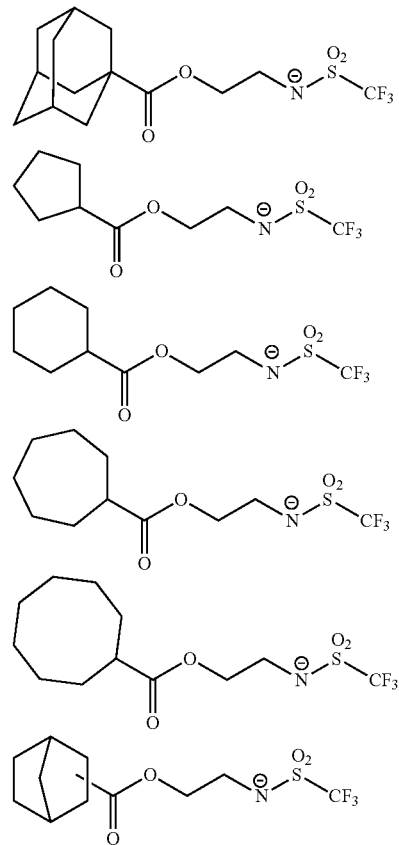

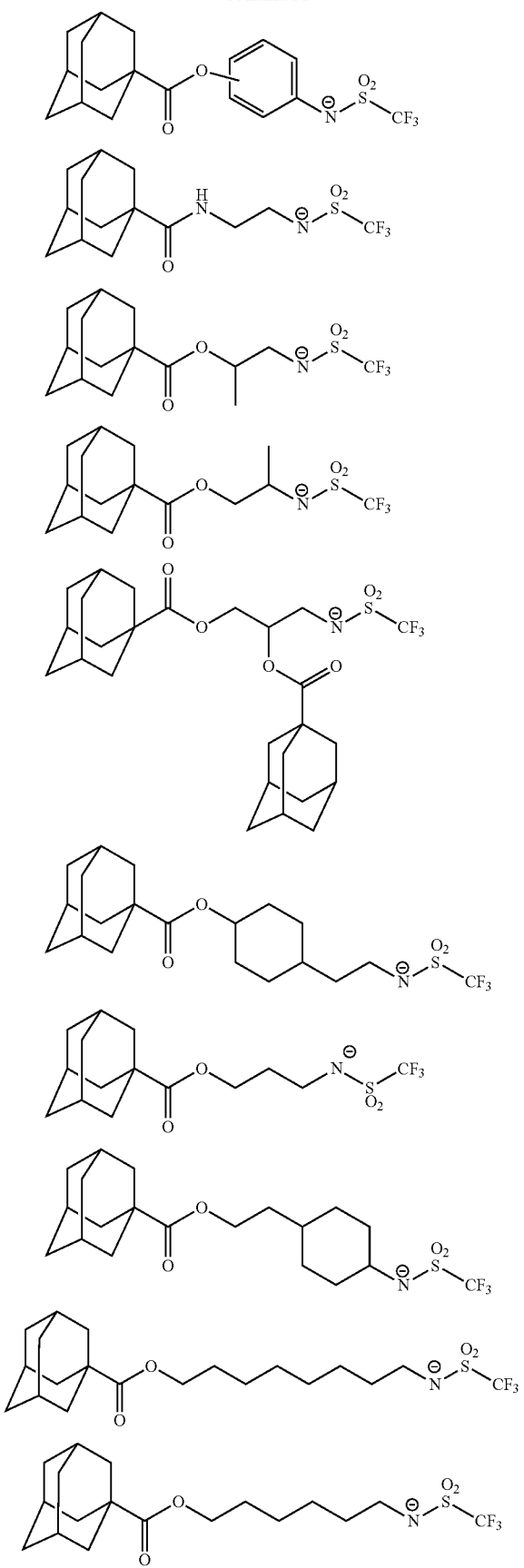
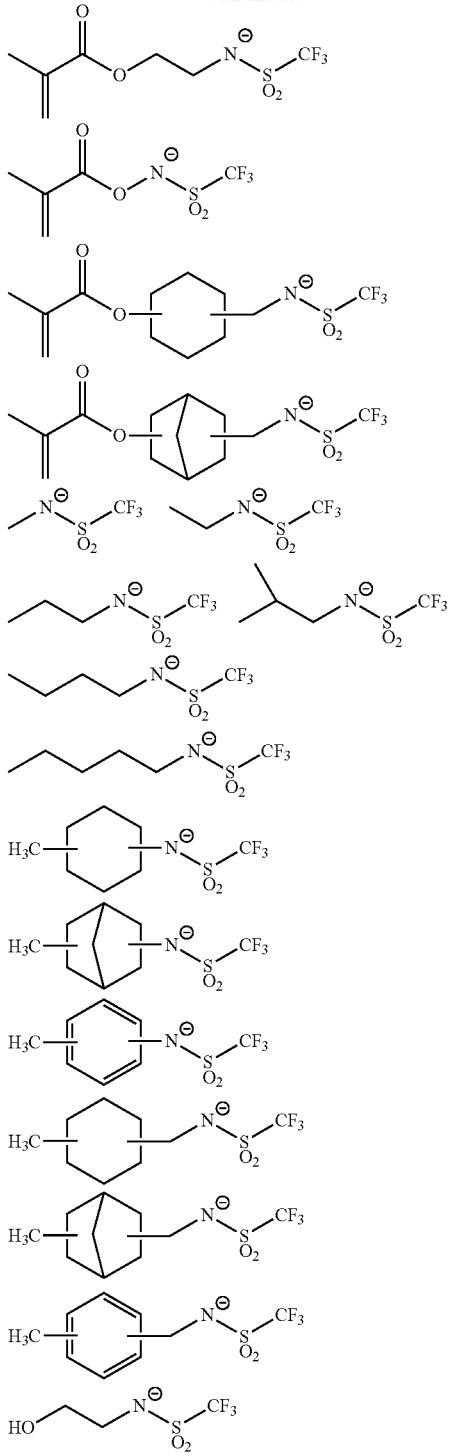
Cation Moiety
In Formula (d1-3), $M^{m+}$ represents an m-valent organic cation, and has the same definition as that for $M^{m+}$ in Formula (d1-1).
The component (d1-3) may be used alone or in a combination of two or more kinds thereof.
As the component (D1), only one of the above-described components (d1-1) to (d1-3) or a combination of two or more kinds thereof may be used. Suitable examples of the component (D1) include a combination of the component (d1-1) and the component (d1-2).

In a case where the resist composition contains the component (D1), the content of the component (D1) in the resist composition is preferably in a range of 0.5 to 20 parts by mass, more preferably in a range of 1 to 15 parts by mass, and still more preferably in a range of 5 to 10 parts by mass with respect to 100 parts by mass of the component (A).

In a case where the content of the component (D1) is greater than or equal to the preferable lower limit, the lithography characteristics such as CDU and DOF become excellent. Meanwhile, in a case where the content thereof is less than or equal to the upper limit thereof, the sensitivity can be maintained satisfactorily, and through-put also becomes excellent.

Method of Producing Component (D1):

The production methods of the components (d1-1) and (d1-2) are not particularly limited, and the components (d1-1) and (d1-2) can be produced by known methods.

Further, the method of producing the component (d1-3) is not particularly limited, and the component (d1-3) can be produced in the same manner as disclosed in United States Patent Application, Publication No. 2012-0149916.

Component (D2)

The resist composition may contain a nitrogen-containing organic compound component (hereinafter, referred to as a "component (D2)") that does not correspond to the component (D1) as the acid diffusion control agent component.

The component (D2) is not particularly limited, as long as it acts as an acid diffusion control agent and does not correspond to the component (D1). As the component (D2), any of the conventionally known compounds may be optionally used. Among these, an aliphatic amine is preferable, and a secondary aliphatic amine or tertiary aliphatic amine is particularly preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group having 12 or fewer carbon atoms (alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include 4-dimethylaminopyridine, pyrrole, indole, pyrazole, imidazole and derivatives thereof as well as tribenzylamine, 2,6-diisopropylaniline and N-tert-butoxycarbonylpyrrolidine.

The component (D2) may be used alone or in a combination of two or more kinds thereof.

In a case where the resist composition contains the component (D2), the content of the component (D2) in the resist composition is typically in a range of 0.01 to 5 parts by mass with respect to 100 parts by mass of the component (A). In a case where the content thereof is in the above-described range, the shape of the resist pattern and the post exposure temporal stability are improved.

<<Compound (E): At Least One Compound Selected from Group Consisting of Organic Carboxylic Acids, Phosphorus Oxo Acids, and Derivatives Thereof>>

For the purpose of preventing any deterioration in sensitivity, and improving the resist pattern shape and the post exposure temporal stability, the resist composition of the present embodiment may contain at least one compound (E) (hereinafter referred to as the component (E)) selected from the group consisting of an organic carboxylic acid, or a phosphorus oxo acid and a derivative thereof.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid, and phosphinic acid. Among these, phosphonic acid is particularly preferable.

Examples of phosphorus oxo acid derivatives include esters in which a hydrogen atom in the above-described oxo acids is substituted with a hydrocarbon group. Examples of the hydrocarbon group include an alkyl group having 1 to 5 carbon atoms and an aryl group having 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate, and dibenzyl phosphonate.

Examples of phosphinic acid derivatives include phosphinic acid esters and phenylphosphinic acid.

In the resist composition of the present embodiment, the component (E) may be used alone or in a combination of two or more kinds thereof.

In a case where the resist composition contains the component (E), the content of the component (E) is typically in a range of 0.01 to 5 parts by mass, with respect to 100 parts by mass of the component (A).

<<Component (F): Fluorine Additive Component>>

In the present embodiment, the resist composition may further include a fluorine additive (hereinafter, referred to as a "component (F)") for imparting water repellency to the resist film.

As the component (F), fluorine-containing polymeric compounds described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be exemplified.

Specific examples of the component (F) include polymers having a constitutional unit (f1) represented by Formula (f1-1) shown below. As the polymer, a polymer (homopolymer) formed of only a constitutional unit (f1) represented by Formula (f1-1) shown below; a copolymer of the constitutional unit (f1) and the constitutional unit (a1); and a copolymer of the constitutional unit (f1), a constitutional unit derived from acrylic acid or methacrylic acid and the above-described constitutional unit (a1) are preferable. Examples of the constitutional unit (a1) to be copolymerized with the constitutional unit (f1) include a constitutional unit derived from 1-ethyl-1-cyclooctyl (meth)acrylate and a constitutional unit derived from 1-methyl-1-adamantyl (meth)acrylate.

Further, specific examples of the component (F) include a polymer having a constitutional unit represented by Formula (f1-2). As the polymer, a polymer (homopolymer) formed of only a constitutional unit (f2) represented by Formula (f1-2); or a copolymer of the constitutional unit (f2) and the constitutional unit (a4) is preferable. Here, as the constitutional unit (a4) to be copolymerized with the constitutional unit (f2), any of constitutional units represented by Formulae (a4-1) to (a4-7) is preferable, and a constitutional unit represented by Formula (a4-2) is more preferable.

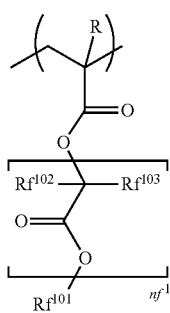

(f1-1)

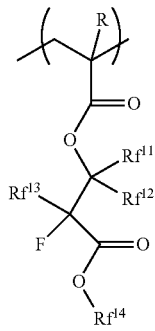

(f1-2)

[In the formulae, R has the same definition as described above. $Rf^{102}$ and $Rf^{103}$ each independently represent a hydrogen atom, a halogen atom, an alkyl group having 1 to 5 carbon atoms, or a halogenated alkyl group having 1 to 5 carbon atoms, and $Rf^{102}$ and $Rf^{103}$ may be the same as or different from each other. $nf^1$ represents an integer of 0 to 5, and $Rf^{101}$ represents an organic group containing a fluorine atom. $R^{f11}$ and $R^{f12}$ each independently represent a hydrogen atom, an alkyl group having 1 to 4 carbon atoms, or a fluorinated alkyl group having 1 to 4 carbon atoms. $R^{f13}$ represents a fluorine atom or a fluorinated alkyl group having 1 to 4 carbon atoms. $R^{f14}$ represents a linear or branched alkyl group having 1 to 4 carbon atoms or a linear fluorinated alkyl group having 1 to 4 carbon atoms.

In Formula (f1-1), R bonded to the carbon atom at the α-position has the same definition as described above. As R, a hydrogen atom or a methyl group is preferable.

In Formula (f1-1), examples of the halogen atom of $Rf^{102}$ and $Rf^{103}$ include a fluorine atom, a chlorine atom, a bromine atom, and an iodine atom, and a fluorine atom is particularly preferable. Examples of the alkyl group having 1 to 5 carbon atoms of $Rf^{102}$ and $Rf^{103}$ include those described above as the alkyl group having 1 to 5 carbon atoms of R, and a methyl group or an ethyl group is preferable. Specific examples of the halogenated alkyl group having 1 to 5 carbon atoms of $Rf^{102}$ and $Rf^{103}$ include groups in which some or all hydrogen atoms of the above-described alkyl groups of 1 to 5 carbon atoms have been substituted with halogen atoms.

Examples of the halogen atom include a fluorine atom, a chlorine atom, a bromine atom, and an iodine atom, and a fluorine atom is particularly preferable. Among these examples, as $Rf^{102}$ and $Rf^{103}$, a hydrogen atom, a fluorine atom, or an alkyl group having 1 to 5 carbon atoms is preferable, and a hydrogen atom, a fluorine atom, a methyl group, or an ethyl group is more preferable.

In Formula (f1-1), $nf^1$ represents an integer of 1 to 5, preferably an integer of 1 to 3, and more preferably an integer of 1 or 2.

In Formula (f1-1), $Rf^{101}$ represents an organic group containing a fluorine atom, and is preferably a hydrocarbon group containing a fluorine atom.

The hydrocarbon group containing a fluorine atom may be linear, branched, or cyclic, and preferably has 1 to 20 carbon atoms, more preferably 1 to 15 carbon atoms, and particularly preferably 1 to 10 carbon atoms.

It is preferable that the hydrocarbon group having a fluorine atom have 25% or more of the hydrogen atoms in the hydrocarbon group fluorinated, more preferably 50% or greater, and particularly preferably 60% or greater from the viewpoint of improving the hydrophobicity of the resist film during immersion exposure.

Among these, as $Rf^{101}$, a fluorinated hydrocarbon group having 1 to 6 carbon atoms is preferable, and a trifluoromethyl group, —$CH_2$—$CF_3$, —$CH_2$—$CF_2$—$CF_3$, —$CH(CF_3)_2$, —$CH_2$—$CH_2$—$CF_3$, and —$CH_2$—$CH_2$—$CF_2$—$CF_2$—$CF_2$—$CF_3$ are still more preferable, and —$CH_2$—$CF_3$ is particularly preferable.

In Formula (f1-2), R bonded to the carbon atom at the α-position has the same definition as described above. It is preferable that R represent a hydrogen atom or a methyl group.

In Formula (f1-2), $Rf^{11}$ and $Rf^{12}$ each independently represent a hydrogen atom, an alkyl group having 1 to 4 carbon atoms, or a fluorinated alkyl group having 1 to 4 carbon atoms.

The alkyl group having 1 to 4 carbon atoms of $Rf^{11}$ and $Rf^{12}$ may be linear, branched, or cyclic, and a linear or branched alkyl group is preferable. Specific examples thereof include a methyl group and an ethyl group. Among these, an ethyl group is particularly preferable.

The fluorinated alkyl group having 1 to 4 carbon atoms of $Rf^{11}$ and $Rf^{12}$ is a group in which some or all hydrogen atoms in the alkyl group having 1 to 4 carbon atoms have been substituted with fluorine atoms. In the fluorinated alkyl group, the alkyl group in which the substitution with fluorine atoms has not been performed may be linear, branched, or cyclic, and examples thereof are the same as those exemplified as the "alkyl group having 1 to 4 carbon atoms represented by $Rf^{11}$ and $Rf^{12}$".

Among these, it is preferable that $Rf^{11}$ and $Rf^{12}$ represent a hydrogen atom or an alkyl group having 1 to 4 carbon atoms and particularly preferable that one of $Rf^{11}$ and $Rf^{12}$ represent a hydrogen atom and the other represent an alkyl group having 1 to 4 carbon atoms.

In Formula (f1-2), $Rf^{13}$ represents a fluorine atom or a fluorinated alkyl group having 1 to 4 carbon atoms.

Examples of the fluorinated alkyl group having 1 to 4 carbon atoms of $Rf^{13}$ are the same as those exemplified as the "fluorinated alkyl group having 1 to 4 carbon atoms represented by $Rf^{11}$ and $Rf^{12}$", and the number of carbon atoms thereof is preferably in a range of 1 to 3 and more preferably 1 or 2.

In the fluorinated alkyl group of $Rf^{13}$, the ratio (fluorination ratio (%)) of the number of fluorine atoms to the total number of fluorine atoms and hydrogen atoms contained in the fluorinated alkyl group is preferably in a range of 30% to 100% and more preferably in a range of 50% to 100%. As the fluorination ratio is increased, the hydrophobicity of the resist film is increased.

In Formula (f1-2), $Rf^{14}$ represents a linear or branched alkyl group having 1 to 4 carbon atoms or a linear fluorinated alkyl group having 1 to 4 carbon atoms and preferably a linear alkyl group having 1 to 4 carbon atoms or a linear fluorinated alkyl group having 1 to 4 carbon atoms.

Specific examples of the alkyl group of $Rf^{14}$ include a methyl group, an ethyl group, a propyl group, an isopropyl group, an n-butyl group, an isobutyl group, and a tert-butyl group. Among these, a methyl group or an ethyl group is preferable, and a methyl group is most preferable.

Specific suitable examples of the fluorinated alkyl group of $Rf^{14}$ include —$CH_2$—$CF_3$, —$CH_2$—$CH_2$—$CF_3$, —$CH_2$—$CF_2$—$CF_3$, and —$CH_2$—$CF_2$—$CF_2$—$CF_3$. Among these, —$CH_2$—$CH_2$—$CF_3$ or —$CH_2$—$CF_3$ is particularly preferable.

The weight average molecular weight (Mw) (in terms of polystyrene determined by gel permeation chromatography) of the component (F) is preferably in a range of 1,000 to 50,000, more preferably in a range of 5,000 to 40,000, and most preferably in a range of 10,000 to 30,000. In a case where the weight average molecular weight is less than or equal to the upper limit of the above-described range, the resist composition exhibits satisfactory solubility in a solvent for a resist enough to be used as a resist. On the other hand, in a case where the weight average molecular weight is greater than or equal to the lower limit of the above-described range, dry etching resistance and the cross-sectional shape of the resist pattern become excellent.

Further, the dispersity (Mw/Mn) of the component (F) is preferably in a range of 1.0 to 5.0, more preferably in a range of 1.0 to 4.0, and most preferably in a range of 1.0 to 2.5.

In the resist composition of the present embodiment, the component (F) may be used alone or in a combination of two or more kinds thereof.

In a case where the resist composition contains the component (F), the content of the component (F) is typically in a range of 0.5 to 10 parts by mass, with respect to 100 parts by mass of the component (A).

<<Component (S): Organic Solvent Component>>

The resist composition of the present embodiment may be produced by dissolving the resist materials in an organic solvent (hereinafter, referred to as a "component (S)").

The component (S) may be any organic solvent which can dissolve the respective components to be used to obtain a uniform solution, and an optional organic solvent can be appropriately selected from those which are conventionally known as solvents for a chemically amplified resist composition and then used.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (such as monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

In the resist composition of the present embodiment, the component (S) may be used alone or in the form of a mixed solvent of two or more kinds thereof.

Among these, PGMEA, PGME, γ-butyrolactone, EL and cyclohexanone are preferable.

Further, among the mixed solvents, a mixed solvent obtained by mixing PGMEA with a polar solvent is preferable. The mixing ratio (mass ratio) of the mixed solvent can be appropriately determined in consideration of the compatibility of the PGMEA with the polar solvent, but is preferably in a range of 1:9 to 9:1 and more preferably in a range of 2:8 to 8:2.

More specifically, in a case where EL or cyclohexanone is mixed as the polar solvent, the PGMEA:EL or cyclohexanone mass ratio is preferably in a range of 1:9 to 9:1 and more preferably in a range of 2:8 to 8:2. Alternatively, in a case where PGME is mixed as the polar solvent, the PGMEA:PGME mass ratio is preferably in a range of 1:9 to 9:1, more preferably in a range of 2:8 to 8:2, and still more preferably in a range of 3:7 to 7:3. Furthermore, a mixed solvent of PGMEA, PGME and cyclohexanone is also preferable.

Further, as the component (S), a mixed solvent of at least one of PGMEA and EL with γ-butyrolactone is also preferable. The mixing ratio (former:latter) of such a mixed solvent is preferably in a range of 70:30 to 95:5.

The amount of the component (S) is not particularly limited, and is appropriately adjusted to a concentration which enables coating of a coating solution on a substrate. In general, the component (S) is used in an amount such that the solid content of the resist composition comes within a range of 1% to 20% by mass and preferably within a range of 2% to 15% by mass.

As desired, other miscible additives can also be added to the resist composition of the present invention. The resist composition may contain miscible additives such as additive resins, dissolution inhibitors, plasticizers, stabilizers, colorants, halation prevention agents, and dyes for improving the performance of the resist film, as appropriate.

The resist composition of the present embodiment has excellent lithography characteristics such as CDU and DOF. The reason why such effects are obtained is not clear, but can be assumed as follows.

Further, in the resist composition of the present embodiment, the component (B) contains a component (B1) formed of a compound represented by Formula (b1). The anion moiety of the component (B1) contains a cyclic aliphatic hydrocarbon group in addition to the steroid skeleton so that the component (B) has a bulkier structure than that of the anion moiety having a steroid skeleton of the related art. Therefore, it is assumed that the diffusion in the resist film is appropriately controlled due to the component (B1).

It is assumed that the lithography characteristics such as CDU and DOF become excellent because of the effects of the component (B).

(Method of Forming a Resist Pattern)

The method of forming a resist pattern according to the present embodiment includes a step of forming a resist film on a support using the resist composition of the embodiment; a step of exposing the resist film; and a step of developing the exposed resist film to form a resist pattern.

According to the embodiment of the method of forming a resist pattern, a method for forming a resist pattern by performing the processes described below is exemplified.

First, a resist composition of the according to the embodiment is applied to a support using a spinner or the like, and a bake treatment (post applied bake (PAB)) is conducted at a temperature of 80 to 150° C. for 40 to 120 seconds and preferably 60 to 90 seconds, to form a resist film.

Following selective exposure of the thus formed resist film, by exposure through a mask having a predetermined pattern formed thereon (mask pattern) using an exposure apparatus such as an electron beam lithography apparatus or an EUV exposure apparatus, or by patterning via direct irradiation with an electron beam without using a mask pattern, baking treatment (post exposure baking (PEB)) is conducted under temperature conditions of 80 to 150° C. for 40 to 120 seconds, and preferably 60 to 90 seconds.

Next, the resist film is subjected to a developing treatment. The developing treatment is conducted using an alkali developing solution in a case of an alkali developing process, and a developing solution containing an organic solvent (organic developing solution) in a case of a solvent developing process. The method of forming a resist pattern of the present embodiment is particularly useful in a case of the solvent developing process.

After the developing treatment, it is preferable to conduct a rinse treatment. The rinse treatment is preferably conducted using pure water in a case of an alkali developing process, and a rinse solution containing an organic solvent in a case of a solvent developing process.

In a case of a solvent developing process, after the developing treatment or the rinsing, the developing solution or the rinse liquid remaining on the pattern can be removed by a treatment using a supercritical fluid.

After the developing treatment or the rinse treatment, drying is conducted. As desired, bake treatment (post bake) can be conducted following the developing.

In this manner, a resist pattern can be formed.

The support is not specifically limited and a conventionally known support can be used. For example, substrates for electronic components, and such substrates having wiring patterns formed thereon can be used. Specific examples of the material of the substrate include metals such as a silicon wafer, copper, chromium, iron and aluminum; and glass. Suitable materials for the wiring pattern include copper, aluminum, nickel, and gold.

Further, as the support, any one of the above-described supports provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is a method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as to enable a pattern to be formed with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film is formed (triple-layer resist method).

The wavelength to be used for exposure is not particularly limited and the exposure can be conducted using radiation such as an ArF excimer laser, a KrF excimer laser, an F2 excimer laser, extreme ultraviolet rays (EUV), vacuum ultraviolet rays (VUV), electron beams (EB), X-rays, and soft X-rays. The resist composition of the present invention is useful for a KrF excimer laser, an ArF excimer laser, EB, and EUV and more useful for an ArF excimer laser, EB, and EUV.

The exposure of the resist film can be general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has refractive index larger than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-described requirements.

Examples of this immersion medium which exhibits a refractive index that is larger than the refractive index of air but smaller than the refractive index of the resist film include water, fluorine-based inert liquids, silicon-based solvents, and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, and the boiling point is preferably in a range of 70° C. to 180° C. and more preferably in a range of 80° C. to 160° C. A fluorine-based inert liquid having a boiling point in the above-described range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly preferable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point of 102° C.), and an example of a suitable perfluoroalkylamine compound is perfluorotributylamine (boiling point of 174° C.).

As the immersion medium, water is preferable in terms of cost, safety, environment and versatility.

As an example of the alkali developing solution used in an alkali developing process, a 0.1 to 10 mass % aqueous solution of tetramethylammonium hydroxide (TMAH) can be exemplified.

As the organic solvent contained in the organic developing solution used in a solvent developing process, any of the conventional organic solvents which are capable of dissolving the component (A) (prior to exposure) can be used. Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C in the structure thereof. An ester solvent is an organic solvent containing C—C(=O)—O—C in the structure thereof. An alcohol solvent is an organic solvent containing an alcoholic hydroxyl group in the structure thereof. An "alcoholic hydroxyl group" indicates a hydroxyl group bonded to a carbon atom of an aliphatic hydrocarbon group. A nitrile solvent is an organic solvent containing a nitrile group in the structure thereof. An amide solvent is an organic solvent containing an amide group in the structure thereof. An ether solvent is an organic solvent containing C—O—C in the structure thereof.

Some organic solvents have a plurality of the functional groups which characterize the above-described solvents in the structure thereof. In such a case, the organic solvent can be classified as any type of solvent having the characteristic functional group. For example, diethylene glycol monomethylether can be classified as an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

As the organic solvent contained in the organic developing solution, among these, a polar solvent is preferable, and ketone solvents, ester solvents, and nitrile solvents are preferable.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone). Among these examples, as a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxYbutyl acetate, 3-methoxYbutyl acetate, 4-methoxYbutyl acetate, 3-methyl-3-methoxYbutyl acetate, 3-ethyl-3-methoxYbutyl acetate, propylene glycol monomethyl ether acetate, propylene glycol monoethyl ether acetate, propylene glycol monopropyl ether acetate, 2-ethoxYbutyl acetate, 4-ethoxYbutyl acetate, 4-propoxYbutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate, and propyl-3-methoxypropionate. Among these examples, as an ester solvent, butyl acetate is preferable.

Examples of nitrile solvents include acetonitrile, propionitrile, valeronitrile, butyronitrile and the like.

As desired, the organic developing solution may have a conventional additive blended. Examples of the additive include surfactants. The surfactant is not particularly limited, and for example, an ionic or non-ionic fluorine and/or silicon surfactant can be used.

As the surfactant, a non-ionic surfactant is preferable, and a non-ionic fluorine surfactant or a non-ionic silicon surfactant is more preferable.

In a case where a surfactant is added, the amount thereof based on the total amount of the organic developing solution is generally 0.001% to 5% by mass, preferably 0.005% to 2% by mass, and more preferably 0.01% to 0.5% by mass.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in a case of a solvent developing process, any of the above-described organic solvents contained in the organic developing solution that does not easily dissolve the resist pattern can be used. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents is more preferable, and ester solvents, and an alcohol solvent is particularly preferable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol, and benzyl alcohol. Among these, 1-hexanol, 2-heptanol and 2-hexanol are preferable, and 1-hexanol and 2-hexanol are more preferable.

As the organic solvent, one kind of solvent may be used alone, or two or more kinds of solvents may be used in combination. Further, an organic solvent other than the above-described examples or water may be mixed together. However, in consideration of the development characteristics, the amount of water in the rinse liquid based on the total amount of the rinse liquid is preferably 30% by mass or less, more preferably 10% by mass or less, still more preferably 5% by mass or less, and most preferably 3% by mass or less.

As desired, the rinse solution may have a conventional additive blended. Examples of the additive include surfactants. Examples of the additive include surfactants. As the surfactant, the same surfactants as those described above can be exemplified, a non-ionic surfactant is preferable, and a non-ionic fluorine surfactant or a non-ionic silicon surfactant is more preferable.

In a case where a surfactant is added, the amount thereof based on the total amount of the rinse liquid is generally 0.001% to 5% by mass, preferably 0.005% to 2% by mass, and more preferably 0.01% to 0.5% by mass.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

(Compound)
A third aspect of the present invention is a compound represented by Formula (b1).

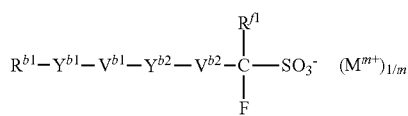

[In the formula, $R^{b1}$ represents a monovalent hydrocarbon group which has a steroid skeleton and 17 to 50 carbon atoms, where the hydrocarbon group may have a hetero atom. $Y^{b1}$ and $Y^{b2}$ each independently represent a divalent linking group having a hetero atom. $V^{b1}$ represents a divalent linking group containing a cyclic aliphatic hydrocarbon group. $V^{b2}$ represents an alkylene group, a fluorinated alkylene group, or a single bond. $R^{f1}$ represents a hydrogen atom, a fluorine atom, or a fluorinated alkyl group having 1 to 5 carbon atoms. m represents an integer of 1 or greater, and $M^{m+}$ represents an m-valent organic cation.]

In the compound of the present embodiment, the description of the compound represented by Formula (b1) is the same as the description of the compound (B1) represented by Formula (b1) in the resist composition according to the first aspect of the present invention.

<<Method of Producing Compound>>

A method of producing the compound of the present invention will be described. A method of producing the compound (B1) is not particularly limited, and known methods can be used.

For example, the compound (B1) can be produced according to a production method including a first step of reacting a compound (1-1) represented by Formula (1-1) with a compound (1-2) represented by Formula (1-2) to synthesize a compound (1) represented by Formula (1); and a second step of exchanging the salt of the compound (1) to obtain the compound (B1).

[First step]

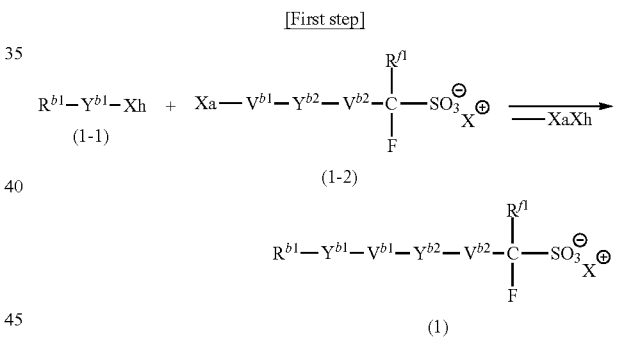

[Second step]

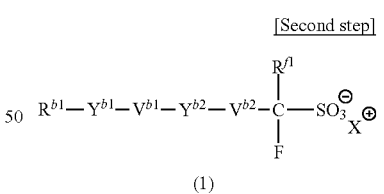

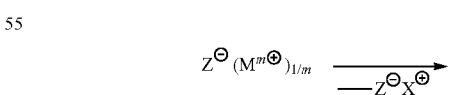

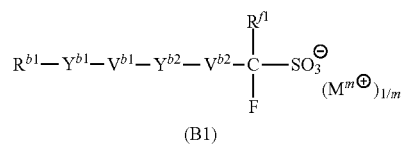

In the reaction formulae shown above, $R^{b1}$, $Y^{b1}$, $V^{b1}$, $Y^{b2}$, $V^{b2}$, $R^{f1}$, M, and m have the same definitions as those represented by Formula (b1). Xh represents a halogen atom and preferably a chlorine atom. Xa represents a functional group and preferably a hydroxy group. $X^+$ represents a monovalent cation and preferably a metal cation or a nitrogen atom-containing cation.

$Z^-$ represents a non-nucleophilic base. Examples of $Z^-$ include a halogen atom such as a bromine ion or a chlorine ion; an ion which may become an acid with a lower acidity than that of a precursor (Bpre), $BF_4^-$, $AsF_6^-$, $SbF_6^-$, $PF_6^-$, and $ClO_4^-$.

As the compounds represented by Formula (1-1) and (1-2), commercially available products or compounds synthesized by known production methods may be used.

The solvent used in the first step is not particularly limited as long as the solvent can dissolve and does not react with the compounds (1-1) and (1-2), and examples of the solvent include dichloromethane, dichloroethane, chloroform, tetrahydrofuran, N,N-dimethylformamide, acetonitrile, and propionitrile.

In the second step, the compound (B1) can be derived by exchanging the salt of the compound (1) with a desired cation. As the cation, a cation represented by Formula (ca-1) is particularly preferable.

After the reaction is completed, the compound in the reaction solution may be isolated and purified. Known methods of the related art can be used for the isolation and the purification. Examples thereof include concentration, solvent extraction, distillation, crystallization, recrystallization, and chromatography, and these methods may be used alone or in a combination of two or more kinds thereof.

The structure of the compound obtained in the above-described manner can be confirmed using typical organic analysis methods such as $^1$H-nuclear magnetic resonance (NMR) spectroscopy, $^{13}$C-NMR spectroscopy, $^{19}$F-NMR spectroscopy, infrared absorption (IR) spectroscopy, a mass spectrometry (MS) method, an element analysis method, and an X-ray crystal diffraction method.

EXAMPLES

Hereinafter, the present invention will be described in detail based on the following examples, but the present invention is not limited to these examples.

Production Examples

Oxalyl chloride (7.1 g) and N,N-dimethylformamide (27 mg) were added dropwise to a mixed solution of dehydrocholic acid (15 g) and dichloromethane (135 g), and the solution was stirred at room temperature for 4 hours. The obtained reaction solution was concentrated, thereby obtaining a compound (17 g) represented by Formula (A).

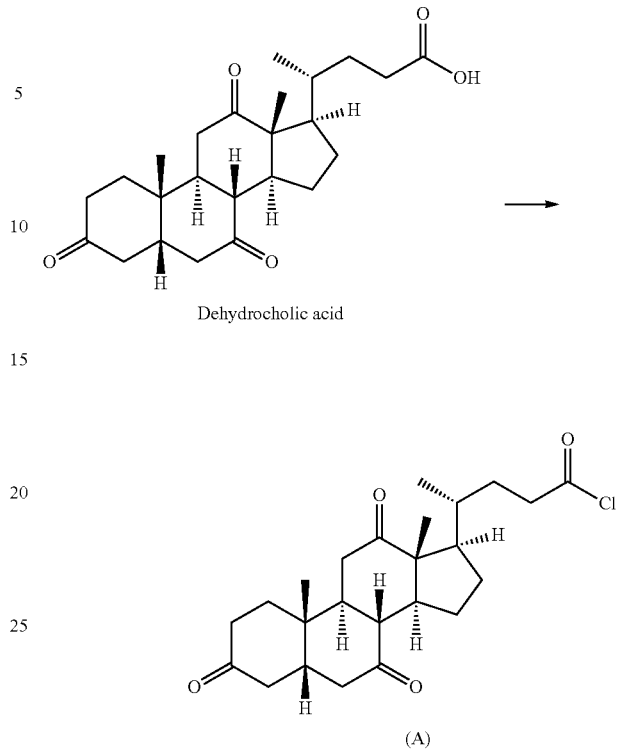

Dehydrocholic acid (A)

<<First Step>>

The compound (15.7 g) represented by Formula (A) and acetonitrile (152 g) were mixed with each other, an acetonitrile (152 g) solution containing a salt (29.9 g) represented by Formula (B) and pyridine (5.9 g) were added to the mixture, and the solution was stirred at 80° C. for 7 hours. The obtained reaction solution was concentrated to obtain a residue (63 g). The residue was allowed to be dissolved in dichloromethane (150 g), a 0.5% sodium hydroxide aqueous solution (100 g) was added thereto, the resulting solution was stirred at room temperature for 30 minutes, and the lower phase was separated. This operation was repeated once. Water (200 g) was added to the recovered organic phase, the solution was stirred at room temperature for 30 minutes, and liquid separation was carried out to recover the organic phase. This washing operation was repeatedly performed four times. The recovered organic phase was concentrated, thereby obtaining a salt (31.27 g) represented by Formula (C).

The results obtained from $^1$H NMR and $^{19}$F NMR measurement performed on the salt represented by Formula (C) are shown below.

$^1$H NMR (400 MHz, DMSO-d6) δ (ppm)=7.53 (m, 5H), 4.99 (m, 1H), 4.52 (s, 2H), 4.30-4.05 (m, 2H), 3.09-2.97 (m, 2H), 3.02 (s, 9H), 2.84 (t, 1H), 2.46-1.40 (m, 33H), 1.40-1.10 (m, 4H), 1.33 (s, 3H), 1.03 (s, 3H), 0.78 (d, 3H).

$^{19}$F NMR (376 MHz, DMSO-d6) δ (ppm)=−112.3 (ddd, 1F), −121.7 (ddd, 1F), −203.3 (m, 1F).

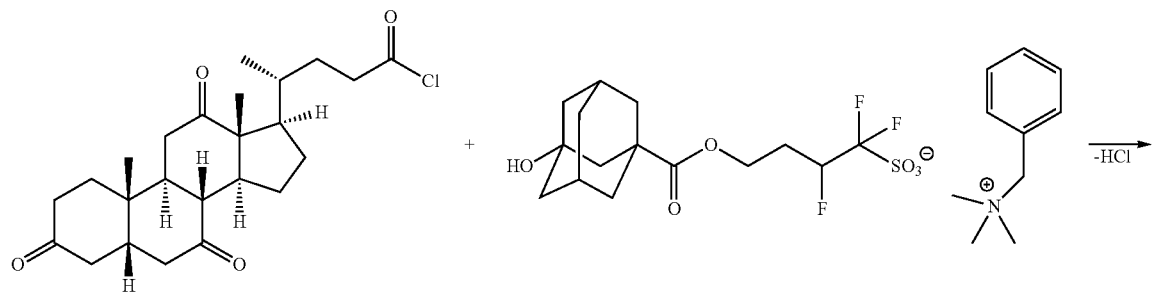

(A)          (B)

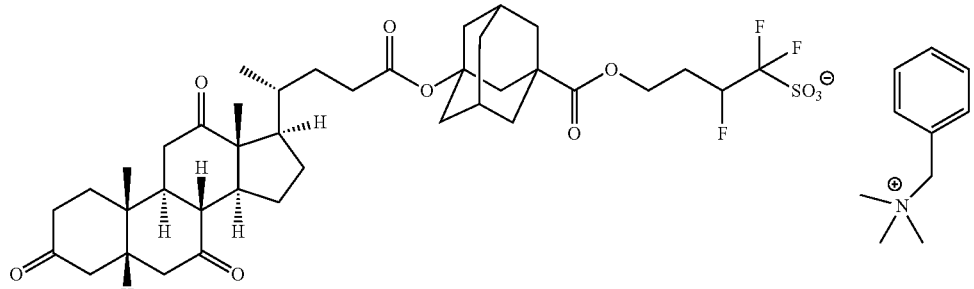

(C)

<<Second Step>>

A salt (19 g) represented by Formula (C), a salt (11.7 g) represented by Formula (D), dichloromethane (200 g), and ion exchange water (112 g) were mixed, the solution was stirred at room temperature for 30 minutes, and the organic phase was separated. Ion exchange water (112 g) was added to the separated organic phase, the solution was stirred at room temperature for 30 minutes, and the organic phase was separated. This washing operation was repeated ten times. The obtained organic layer was concentrated, thereby obtaining 22.0 g of a compound (B1-1).

The results obtained from $^1$H NMR and $^{19}$F NMR measurement performed on the compound (B1-1) are shown below.

$^1$H NMR (400 MHz, DMSO-d6) δ (ppm)=7.93-7.69 (m, 15H), 4.97 (m, 1H), 4.30-4.05 (m, 2H), 3.06 (t, 1H), 2.99 (dd, 1H), 2.84 (t, 1H), 2.46-1.40 (m, 33H), 1.40-1.10 (m, 4H), 1.33 (s, 3H), 1.00 (s, 3H), 0.76 (d, 3H).

$^{19}$F NMR (376 MHz, DMSO-d6) δ (ppm)=−112.8 (ddd, 1F), −121.9 (ddd, 1F), −203.0 (m, 1F).

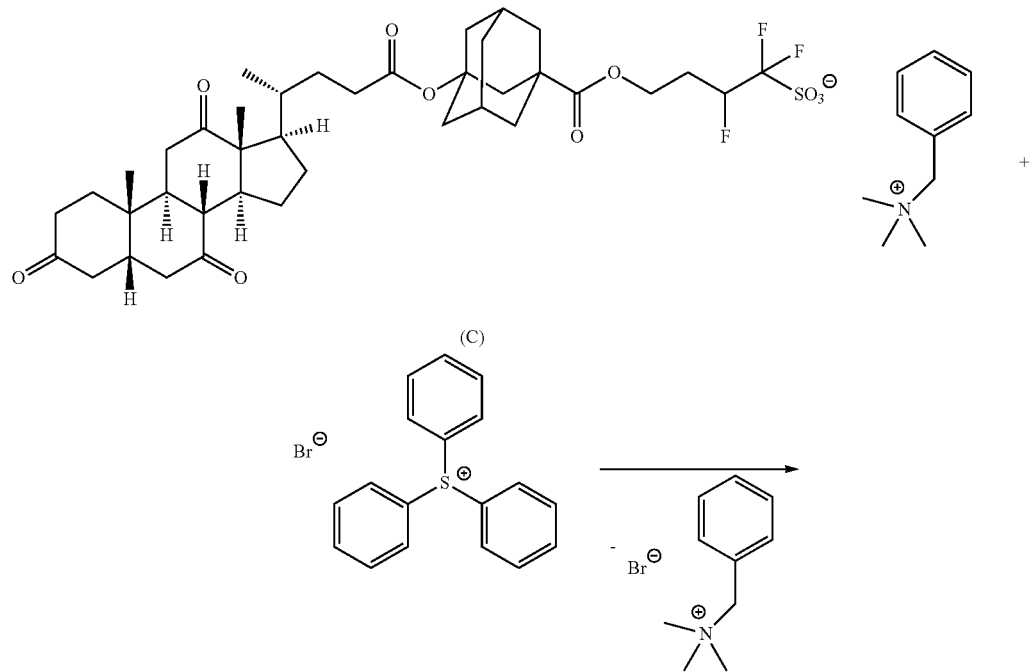

(C)

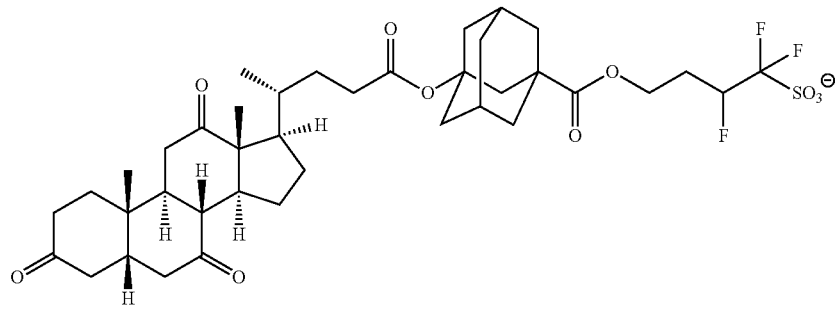

<Preparation of Resist Composition: Example 1 and Comparative Examples 1 and 2>

Respective components listed in Table 1 were mixed so as to be dissolved, thereby preparing resist compositions (a solid content concentration of approximately 3% by mass) of each example.

TABLE 1

| | Component (A) | Component (B) | Component (D) | | Component (F) | Component (S) |
|---|---|---|---|---|---|---|
| Example 1 | (A)-1 [100] | (B)-1 [11.3] | (D)-1 [4.2] | (D)-2 [2.9] | (F)-1 [3.0] | (S)-1 [3650] |
| Comparative Example 1 | (A)-1 [100] | (B)-2 [9.5] | (D)-1 [4.2] | (D)-2 [2.9] | (F)-1 [3.0] | (S)-1 [3650] |
| Example 2 | (A)-1 [100] | (B)-1 [11.3] | (D)-2 [1.5] | (D)-3 [2.2] | (F)-1 [3.0] | (S)-1 [3650] |
| Comparative Example 2 | (A)-1 [100] | (B)-3 [8.4] | (D)-2 [1.5] | (D)-3 [2.2] | (F)-1 [3.0] | (S)-1 [3650] |

The abbreviations in Table 1 have the following meanings. The numerical values in the parentheses are blending amounts (parts by mass).

(A)-1: A polymer compound represented by Chemical Formula (A)-1. This polymer compound (A-1) was obtained by performing radical polymerization on a monomer from which a constitutional unit constituting the polymer compound (A-1) was derived based on a predetermined molar ratio. The weight average molecular weight (Mw) of this polymer compound (A-1) in terms of standard polystyrene acquired by performing GPC measurement was 8,300, and the molecular weight dispersity (Mw/Mn) thereof was 1.66. The copolymerization compositional ratio (the ratio (molar ratio) of each constitutional unit in the structural formula) (1/m/n) acquired by $^{13}$C-NMR was 30:20:50.

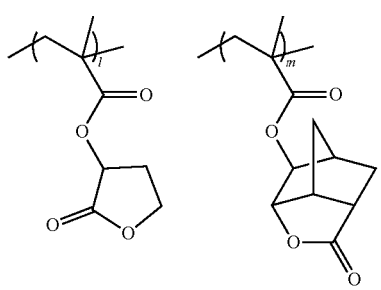

(A)-1

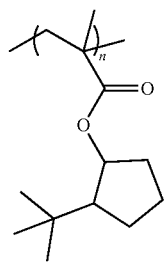

(B)-1: acid generator formed of compound (B1-1) described above (B)-2: acid generator formed of compound (B2-1) described above (B)-3 acid generator formed of compound (B2-2) described above

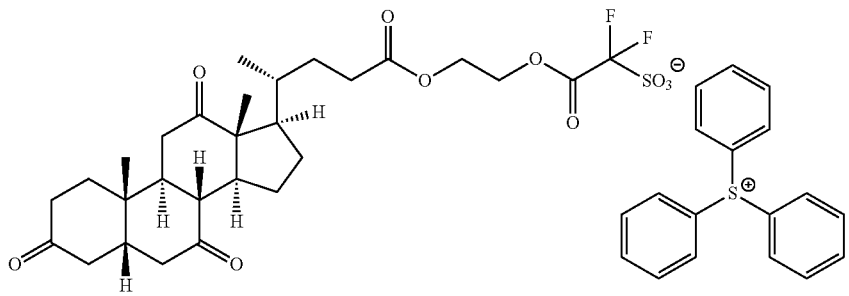
(B2-1)

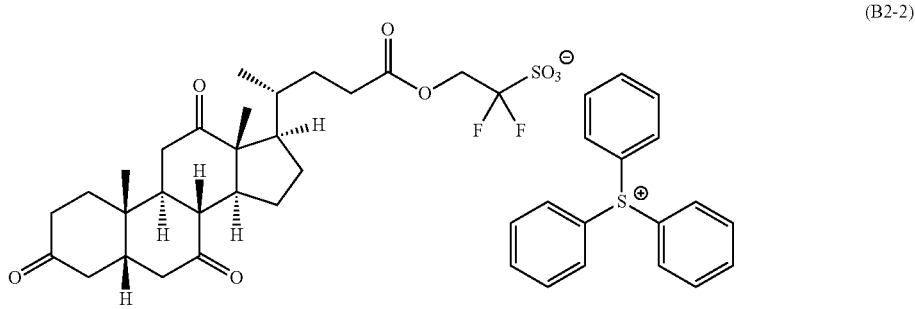
(B2-2)

(D)-1: acid diffusion control agent formed of compound (D1-1) described below (D)-2: acid diffusion control agent formed of compound (D1-2) described below (D)-3: acid diffusion control agent formed of compound (D1-3) described below (F)-1: fluorine-containing polymer compound represented by Chemical Formula (F-1). This fluorine-based polymer compound (F-1) was obtained by performing radical polymerization on a monomer from which a constitutional unit constituting the fluorine-based polymer compound was derived based on a predetermined molar ratio. The weight average molecular weight (Mw) of this fluorine-containing polymer compound (F-1) in terms of standard polystyrene acquired by performing GPC measurement was 15600, and the molecular weight dispersity (Mw/Mn) thereof was 1.66. The copolymerization compositional ratio (the ratio (molar ratio) of each constitutional unit in the structural formula) (1/m) acquired by $^{13}$C-NMR was 50:50.

(S)-1: mixed solution obtained by mixing propylene glycol monomethyl ether acetate, propylene glycol monomethyl ether, and cyclohexanone at mass ratio of 45:30:25.

-continued

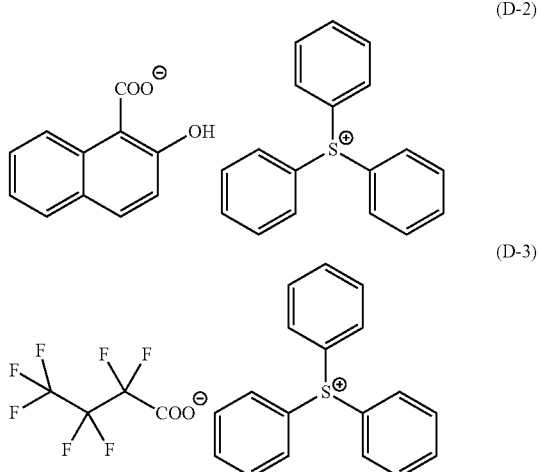
(D-2)

(D-3)

(F-1)

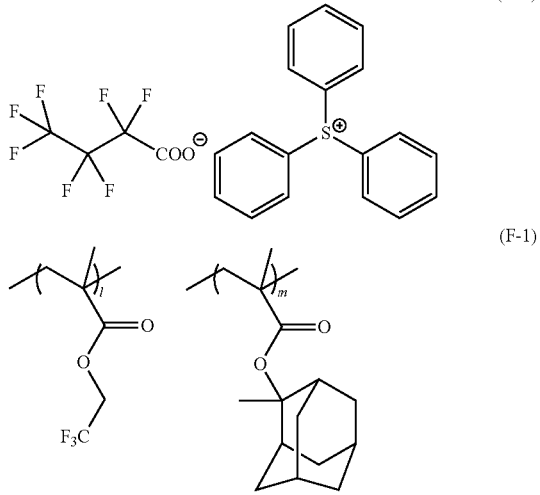

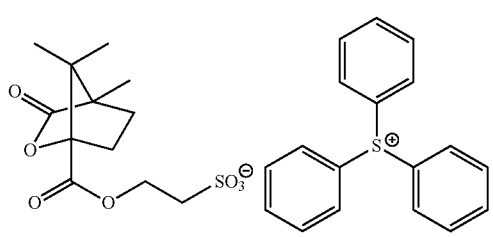
(D-1)

[Formation of Resist Pattern]

A silicon substrate was coated with each resist composition of Examples 1 and 2 and Comparative Examples 1 and 2 using a spinner, and a prebake (PAB) treatment was performed thereon on a hot plate at a temperature of 110° C. for 60 seconds so that the composition was dried to form a resist film having a film thickness of 90 nm.

Next, the resist film was selectively irradiated with an ArF excimer laser (193 nm) using an ArF liquid immersion exposure device NSR-S610C (manufactured by Nikon Corporation; NA 1.30, Crosspole, 0.98/0.78).

Thereafter, the resist film was subjected to a post exposure bake (PEB) treatment at 95° C. for 60 seconds.

Next, solvent development was performed using butyl acetate at 23° C. for 30 seconds, and then a rinse treatment was performed.

As the result, a contact hole pattern (hereinafter, referred to as a "CH pattern") having a hole diameter of 47 nm and a pitch of 86 nm (mask size of 63 nm) was formed.

[Evaluation of Optimum Exposure Amount (Eop)]

An optimum exposure amount Eop (mJ/cm$^2$) at which a target resist pattern was formed was acquired by forming the CH pattern described above. The results are listed in Table 2 in the columns of "Eop (mJ/cm$^2$)".

[Evaluation of in-Plane Uniformity of Pattern Dimension (CDU)]

The CH pattern was observed from above using a length measurement SEM (scanning electron microscope, acceleration voltage of 300 V, trade name: S-9380, manufactured by Hitachi High-Technologies Corporation), and hole diameters (nm) of 100 holes in the CH pattern were measured.

Three times (3σ) (unit: nm) the standard deviation (a) calculated from the measurement results was acquired. The results thereof are listed in Table 2 in the columns of "CDU (nm)".

[Evaluation of Depth of Focus (DOF) Characteristics]

In the formation of a resist pattern, a resist pattern was formed in the same manner as the formation of the resist pattern described above by appropriately shifting the focus in the vertical direction based on the Eop described above. At this time, the depth of focus (DOF, unit: μm) in a range where a space portion was able to be formed was acquired. The results are listed in Table 2 in the columns of "DOF (μm)".

"DOF" indicates a range of the depth of focus where a resist pattern having a predetermined shape can be formed at the time of exposure by shifting the focus in the vertical direction with the same exposure amount, in other words, a range where a resist pattern according to a mask pattern can be obtained. As this range is increased (the value is increased), this means that the process margin is increased.

TABLE 2

|  | Eop (mJ/cm$^2$) | CDU (nm) | DOF (μm) |
| --- | --- | --- | --- |
| Example 1 | 45.4 | 5.04 | 120 |
| Comparative Example 1 | 44.1 | 5.42 | 120 |
| Example 2 | 48.8 | 5.19 | 140 |
| Comparative Example 2 | 46.8 | 5.46 | 120 |

Based on the results listed in Table 2, it was confirmed that the resist compositions of Examples 1 and 2 to which the present invention had been applied had excellent lithography characteristics compared to the resist compositions of Comparative Examples 1 and 2.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates an acid upon exposure and whose solubility in a developing solution is changed due to an action of the acid, the resist composition comprising:

a base material component (A) whose solubility in a developing solution is changed due to the action of an acid; and an acid generator component (B) which generates an acid upon exposure, wherein the acid generator component (B) contains a compound (B1) is represented by Formula (b1);

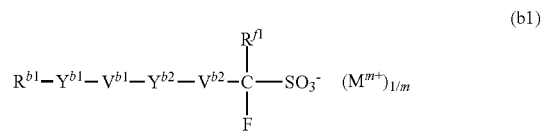

wherein R$^{b1}$ represents a monovalent hydrocarbon group which has a steroid skeleton and 17 to 50 carbon atoms, where the hydrocarbon group may have a hetero atom; Y$^{b1}$ and Y$^{b2}$ each independently represent a divalent linking group having a hetero atom; V$^{b1}$ represents a divalent linking group containing a cyclic aliphatic hydrocarbon group; V$^{b2}$ represents an alkylene group, a fluorinated alkylene group, or a single bond; R$^{f1}$ represents a hydrogen atom, a fluorine atom, or a fluorinated alkyl group having 1 to 5 carbon atoms; m represents an integer of 1 or greater; and M$^{m+}$ represents an m-valent organic cation.

2. The resist composition according to claim 1, wherein V$^{b1}$ in Formula (b1) represents a divalent linking group containing a polycyclic aliphatic hydrocarbon group.

3. The resist composition according to claim 1, wherein the anion moiety in the component (B1) is represented by Formula (b1-an1):

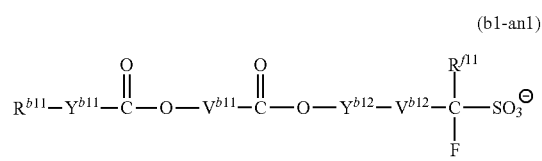

wherein R$^{b11}$ represents a monovalent hydrocarbon group which has a steroid skeleton and 17 to 50 carbon atoms, where the hydrocarbon group may have a hetero atom; Y$^{b11}$ and Y$^{b12}$ each independently represent an alkylene group or a single bond; V$^{b11}$ represents a divalent linking group containing a cyclic aliphatic hydrocarbon group; V$^{b12}$ represents a fluorinated alkylene group or a single bond; and R$^{f11}$ represents a hydrogen atom, a fluorine atom, or a fluorinated alkyl group having 1 to 5 carbon atoms.

4. The resist composition according to claim 2, wherein V$^{b11}$ in Formula (b1-an1) represents a divalent linking group containing a polycyclic aliphatic hydrocarbon group.

5. The resist composition according to claim 1, wherein the base material component (A) contains a polymer compound (A1) having a constitutional unit (a1) that contains an acid decomposable group whose polarity is increased due to the action of an acid.

6. A method of forming a resist pattern, comprising:
forming a resist film on a support using the resist composition according to claim 1;
exposing the resist film; and
developing the exposed resist film to form a resist pattern.

7. A compound represented by Formula (b1):

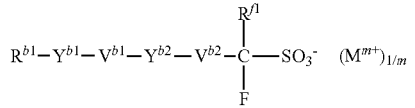

(b1)

wherein $R^{b1}$ represents a monovalent hydrocarbon group which has a steroid skeleton and 17 to 50 carbon atoms, where the hydrocarbon group may have a hetero atom; $Y^{b1}$ and $Y^{b2}$ each independently represent a divalent linking group having a hetero atom; $V^{b1}$ represents a divalent linking group containing a cyclic aliphatic hydrocarbon group; $V^{b2}$ represents an alkylene group, a fluorinated alkylene group, or a single bond, $R^{f1}$ represents a hydrogen atom, a fluorine atom, or a fluorinated alkyl group having 1 to 5 carbon atoms; m represents an integer of 1 or greater; and $M^{m+}$ represents an m-valent organic cation.

8. The compound according to claim 7, wherein $V^{b1}$ in Formula (b1) represents a divalent linking group containing a polyvalent aliphatic hydrocarbon group.

9. The compound according to claim 7, wherein the anion moiety of the compound is represented by Formula (b1-an1):

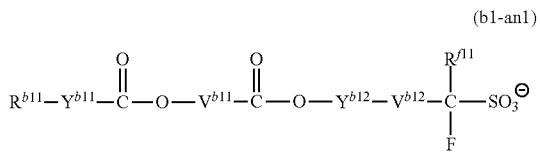

(b1-an1)

wherein $R^{b11}$ represents a monovalent hydrocarbon group which has a steroid skeleton and 17 to 50 carbon atoms, where the hydrocarbon group may have a hetero atom; $Y^{b11}$ and $Y^{b12}$ each independently represent an alkylene group or a single bond; $V^{b11}$ represents a divalent linking group containing a cyclic aliphatic hydrocarbon group; $V^{b12}$ represents a fluorinated alkylene group or a single bond; and $R^{f11}$ represents a hydrogen atom, a fluorine atom, or a fluorinated alkyl group having 1 to 5 carbon atoms.

10. The compound according to claim 9, wherein $V^{b11}$ in Formula (b1-an1) represents a divalent linking group containing a polyvalent aliphatic hydrocarbon group.

* * * * *

UNITED STATES PATENT AND TRADEMARK OFFICE
CERTIFICATE OF CORRECTION

PATENT NO. : 11,036,131 B2
APPLICATION NO. : 16/225290
DATED : June 15, 2021
INVENTOR(S) : Takashi Nagamine, Tsuyoshi Nakamura and Kazuishi Tanno It is certified that error appears in the above-identified patent and that said Letters Patent is hereby corrected as shown below:

In the Specification

In Column 4, Line 55, delete "ester"." and insert -- ester. --.
In Column 9, Line 62, delete "—SO2-containing" and insert -- —SO$_2$-containing --.
In Column 13, Line 54 (approx.), delete "(r-pm-m1)" and insert -- (r-pr-m1) --.
In Column 13, Line 60 (approx.), delete "(r-pm-m2)" and insert -- (r-pr-m2) --.
In Column 14, Line 2 (approx.), delete "(r-pm-m3)" and insert -- (r-pr-m3) --.
In Column 14, Line 9 (approx.), delete "(r-pm-m4)" and insert -- (r-pr-m4) --.
In Column 14, Line 15 (approx.), delete "(r-pm-m5)" and insert -- (r-pr-m5) --.
In Column 14, Line 22 (approx.), delete "(r-pm-m6)" and insert -- (r-pr-m6) --.
In Column 14, Line 27 (approx.), delete "(r-pm-m7)" and insert -- (r-pr-m7) --.
In Column 14, Line 33 (approx.), delete "(r-pm-m8)" and insert -- (r-pr-m8) --.
In Column 14, Line 38 (approx.), delete "(r-pm-m9)" and insert -- (r-pr-m9) --.
In Column 14, Line 44 (approx.), delete "(r-pm-m10)" and insert -- (r-pr-m10) --.
In Column 14, Line 50 (approx.), delete "(r-pm-m11)" and insert -- (r-pr-m11) --.
In Column 14, Line 56 (approx.), delete "(r-pm-m12)" and insert -- (r-pr-m12) --.
In Column 14, Line 61 (approx.), delete "(r-pm-m13)" and insert -- (r-pr-m13) --.
In Column 15, Line 2 (approx.), delete "(r-pm-m14)" and insert -- (r-pr-m14) --.
In Column 15, Line 8 (approx.), delete "(r-pm-m15)" and insert -- (r-pr-m15) --.
In Column 15, Line 15 (approx.), delete "(r-pm-m16)" and insert -- (r-pr-m16) --.
In Column 15, Line 20 (approx.), delete "(r-pm-m17)" and insert -- (r-pr-m17) --.
In Column 52, Line 2 (approx.), delete "[Y$^{21}$"" and insert -- —[Y$^{21}$ --.
In Column 55, Line 11 (approx.), delete "1" and insert -- l --.
In Column 59, Line 2, delete "SO$_3$—)]" and insert -- SO$_3^-$)] --.
In Column 59, Line 66, delete "Ya$^{1}$" and insert -- Ya$^{21}$ --.
In Column 60, Line 52, delete "Yb101" and insert -- Y$^{b101}$ --.
In Column 62, Line 9, delete "Y$^{b21}$" and insert -- Y$^{b201}$ --.
In Column 62, Line 67, delete "Y$^{b11}$" and insert -- Y$^{b11}$, --.
In Column 105, Line 30, delete "dihphenyliodonium" and insert -- diphenyliodonium --.
In Column 113, Lines 35-36, delete "(y-a1-1) to (y-a1-8)" and insert -- (y-al-1) to (y-al-8). --.

Signed and Sealed this
Nineteenth Day of October, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,036,131 B2

In Column 114, Line 1, before "In Formula (b-1)," insert -- [In the formulae, $V'^{101}$ ...... Formulae (y-a1-1) to (y-al-6). --.
In Column 117, Line 44, delete "(y-a1-1) to (y-a1-5)" and insert -- (y-al-1) to (y-al-5) --.
In Column 128, Line 8, delete "$R^{f11}$ and $R^{f12}$" and insert -- $Rf^{11}$ and $Rf^{12}$ --.
In Column 128, Line 10, delete "$R^{f13}$" and insert -- $Rf^{13}$ --.
In Column 128, Line 12, delete "$R^{f14}$" and insert -- $Rf^{14}$ --.
In Column 134, Line 22, delete "methoxYbutyl" and insert -- methoxybutyl --.
In Column 134, Line 22, delete "methoxYbutyl" and insert -- methoxybutyl --.
In Column 134, Line 23, delete "methoxYbutyl" and insert -- methoxybutyl --.
In Column 134, Line 23, delete "methoxYbutyl" and insert -- methoxybutyl --.
In Column 134, Line 24, delete "methoxYbutyl" and insert -- methoxybutyl --.
In Column 134, Line 27, delete "ethoxYbutyl" and insert -- ethoxybutyl --.
In Column 134, Line 27, delete "ethoxYbutyl" and insert -- ethoxybutyl --.
In Column 134, Lines 27-28, delete "propoxYbutyl" and insert -- propoxybutyl --.